United States Patent
Cheng et al.

(10) Patent No.: US 9,893,300 B1
(45) Date of Patent: Feb. 13, 2018

(54) PHENANTHROIMIDAZOLE COMPOUND AND ORGANIC LIGHT-EMITTING DIODE INCLUDING THE SAME

(71) Applicant: National Tsing Hua University, Hsinchu (TW)

(72) Inventors: Chien-Hong Cheng, Hsinchu (TW); Ssu-Yu Liao, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/594,496

(22) Filed: May 12, 2017

(30) Foreign Application Priority Data

Mar. 8, 2017 (TW) .............................. 106107471 A

(51) Int. Cl.
*H01L 29/08* (2006.01)
*H01L 35/24* (2006.01)
(Continued)

(52) U.S. Cl.
CPC ........ *H01L 51/0072* (2013.01); *C07D 235/02* (2013.01); *C07D 401/04* (2013.01);
(Continued)

(58) Field of Classification Search
CPC ............. H01L 51/0072; H01L 51/0058; H01L 51/0067; H01L 51/006; H01L 51/0061; H01L 51/0052; H01L 51/5096; H01L 51/5092; H01L 51/5072; H01L 51/5056; C07D 401/14; C07D 401/04;
(Continued)

(56) References Cited

U.S. PATENT DOCUMENTS 7,291,404 B2  11/2007  Aziz et al.
8,114,315 B2  2/2012  Wei et al.
(Continued)

FOREIGN PATENT DOCUMENTS

CN  102190627  9/2011
CN  103865526  6/2014
(Continued)

*Primary Examiner* — Victor A Mandala
(74) *Attorney, Agent, or Firm* — J.C. PATENTS

(57) ABSTRACT

A phenanthroimidazole compound represented by chemical formula 1 and an organic light-emitting diode including the same are provided.

[Chemical formula 1]

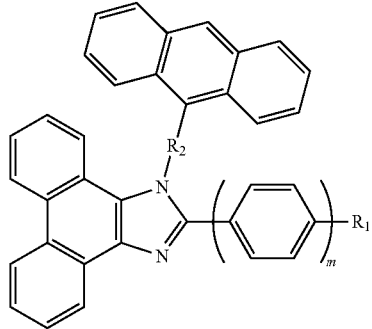

In chemical formula 1, $R_1$, $R_2$, and m are the same as described in the specification.

12 Claims, 4 Drawing Sheets

(51) Int. Cl.
*H01L 51/00* (2006.01)
*C07D 403/10* (2006.01)
*C09K 11/06* (2006.01)
*C07D 235/02* (2006.01)
*C07D 401/10* (2006.01)
*C07D 401/14* (2006.01)
*C07D 403/14* (2006.01)
*C07D 471/04* (2006.01)
*C07D 401/04* (2006.01)
*C07D 403/04* (2006.01)
*H01L 51/50* (2006.01)

(52) U.S. Cl.
CPC ......... *C07D 401/10* (2013.01); *C07D 401/14* (2013.01); *C07D 403/04* (2013.01); *C07D 403/10* (2013.01); *C07D 403/14* (2013.01); *C07D 471/04* (2013.01); *C09K 11/06* (2013.01); *H01L 51/006* (2013.01); *H01L 51/0052* (2013.01); *H01L 51/0058* (2013.01); *H01L 51/0061* (2013.01); *H01L 51/0067* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *H01L 51/5056* (2013.01); *H01L 51/5072* (2013.01); *H01L 51/5092* (2013.01); *H01L 51/5096* (2013.01)

(58) Field of Classification Search
CPC .. C07D 471/04; C07D 403/14; C07D 403/04; C07D 401/10; C07D 235/02; C07D 403/10; C09K 11/06; C09K 2211/1014; C09K 2211/1007; C09K 2211/1029; C09K 2211/1044; C09K 2211/1011
See application file for complete search history.

(56) References Cited

U.S. PATENT DOCUMENTS

| | | | |
|---|---|---|---|
| 2007/0247063 A1* | 10/2007 | Murase | C07D 209/86 313/504 |
| 2009/0309068 A1* | 12/2009 | Schafer | C08G 61/02 252/301.35 |
| 2010/0249349 A1* | 9/2010 | Chebotareva | C08G 61/00 526/259 |

FOREIGN PATENT DOCUMENTS

| | | |
|---|---|---|
| CN | 104099084 | 10/2014 |
| CN | 105602550 | 5/2016 |
| CN | 105647522 | 6/2016 |
| CN | 102617477 | 10/2016 |
| TW | I406851 | 9/2013 |

* cited by examiner

PHENANTHROIMIDAZOLE COMPOUND AND ORGANIC LIGHT-EMITTING DIODE INCLUDING THE SAME

CROSS-REFERENCE TO RELATED APPLICATION

This application claims the priority benefit of Taiwan application serial no. 106107471, filed on Mar. 8, 2017. The entirety of the above-mentioned patent application is hereby incorporated by reference herein and made a part of this specification.

BACKGROUND OF THE INVENTION

Field of the Invention

The invention relates to a compound, and more particularly, to a phenanthroimidazole compound and an organic light-emitting diode containing the same.

Description of Related Art

An organic light-emitting diode (OLED) flat panel display has advantages such as wider viewing angle, faster reaction time, and smaller size in comparison to a liquid crystal display, and is currently applied in large area, high brightness, and full color display.

To develop a full color flat panel display, the development of a stable light-emitting material (red, green, blue) having high luminous efficiency is the main object of current OLED research. However, in comparison to a red light-emitting material and a green light-emitting material, the development of a blue light-emitting material in luminous efficiency is slower, and therefore the development of a novel blue light-emitting material having high luminous efficiency and low driving voltage is an important current object.

SUMMARY OF THE INVENTION

The invention provides a phenanthroimidazole compound that can achieve an organic light-emitting diode having high luminous efficiency.

The invention provides a phenanthroimidazole compound represented by the following chemical formula 1:

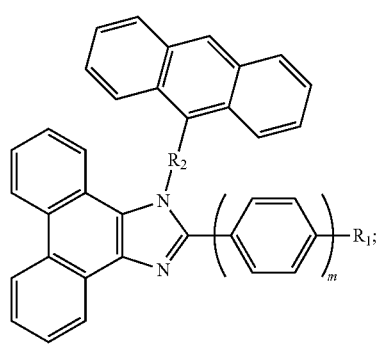

[Chemical formula 1]

in chemical formula 1,
m is an integer of 0 or 1;
when m is 0, $R_1$ is a substituted or unsubstituted carbazolyl group;
when m is 1, $R_1$ is a substituted or unsubstituted carbazolyl group, a substituted or unsubstituted amine group, a substituted or unsubstituted anthryl group, a substituted or unsubstituted pyrenyl group, or a substituted or unsubstituted

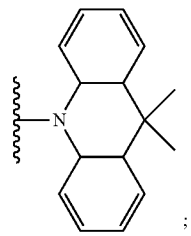 [SMILES: *N1C2C=CC=CC2C(C)(C)C2C=CC=CC21]

;

and
$R_2$ is a substituted or unsubstituted arylene group or a substituted or unsubstituted nitrogen-containing heteroarylene group.

In an embodiment of the invention, when m is 0, $R_1$ is, for instance, a carbazole group substituted by an aryl group or a heteroaryl group.

In an embodiment of the invention, when m is 0, $R_1$ is, for instance, any one selected from the following structures:

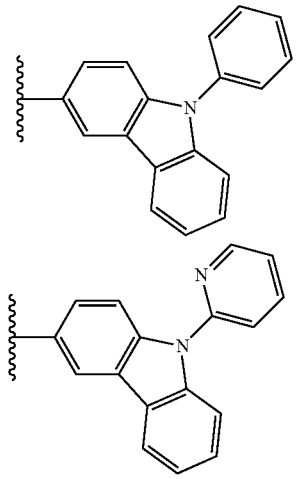

In an embodiment of the invention, when m is 1, $R_1$ is, for instance, a carbazole group, a carbazole group substituted by an alkyl group, an aryl group, or an alkoxy group, or an amine group substituted by an aryl group, anthryl group, pyrenyl group, or

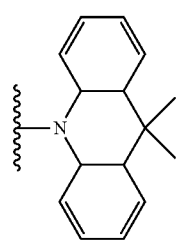

In an embodiment of the invention, when m is 1, $R_1$ is, for instance, any one selected from the following structures:

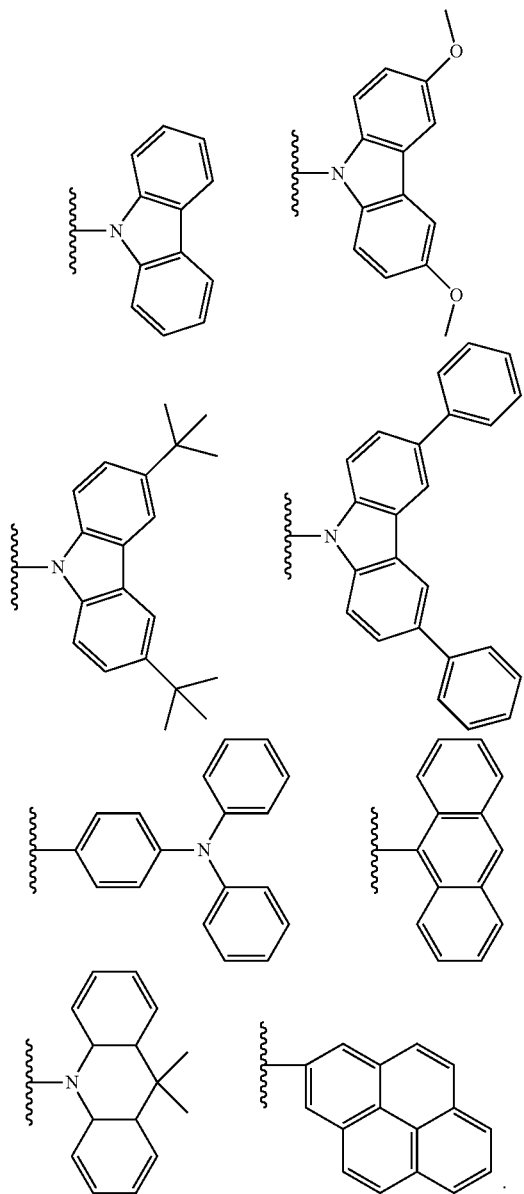
In an embodiment of the invention, $R_2$ is, for instance, any one selected from the following structures:
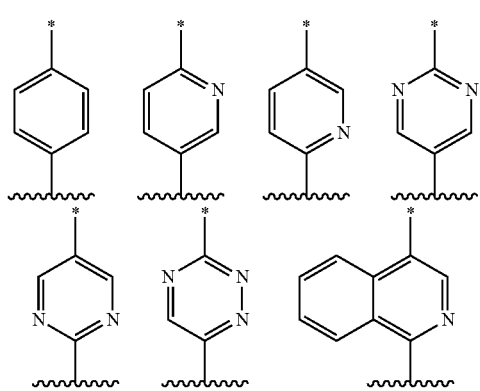
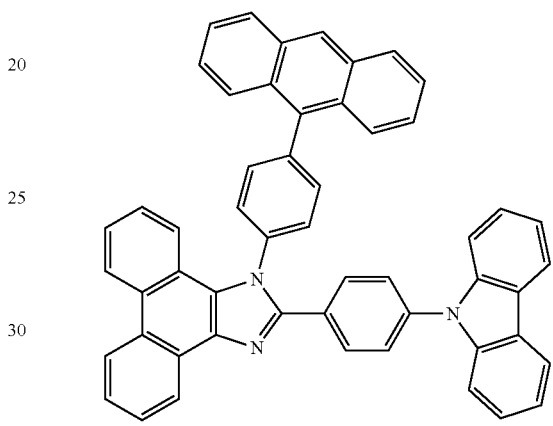
wherein * represents a bonding location with an anthryl group.
In an embodiment of the invention, the phenanthroimidazole compound represented by chemical formula 1 is any one selected from the following structures:
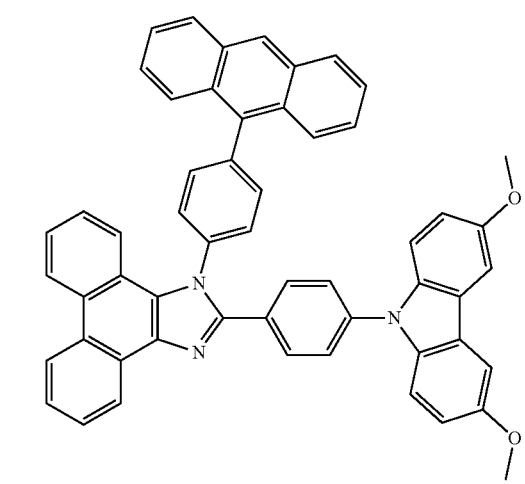

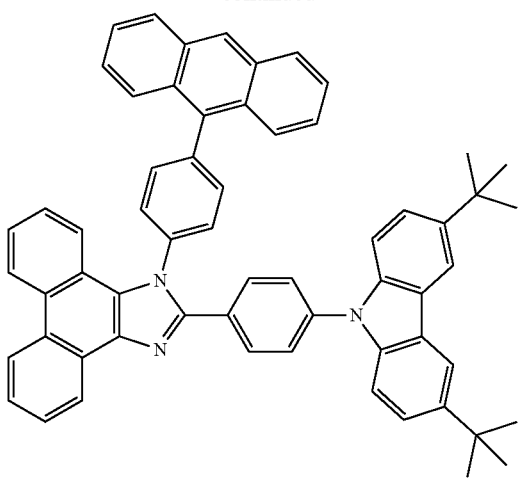
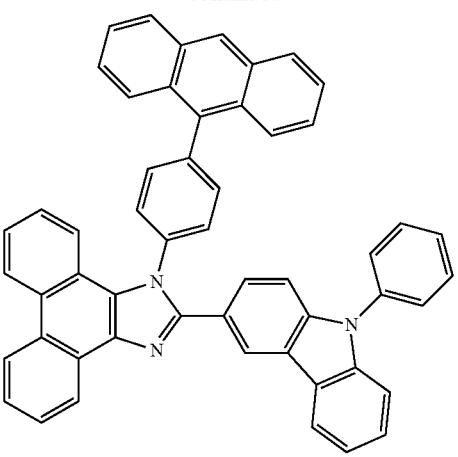
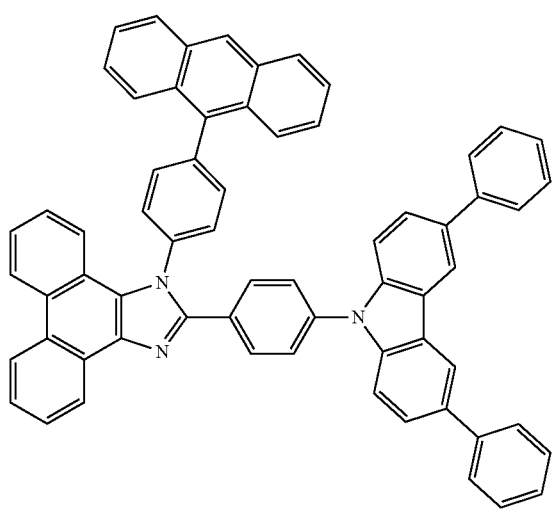
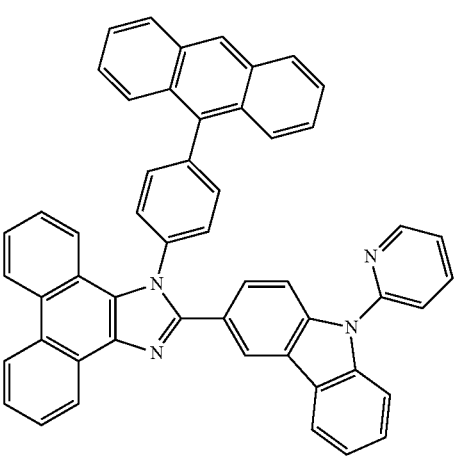
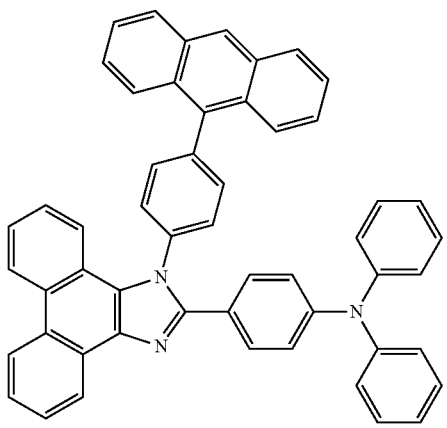
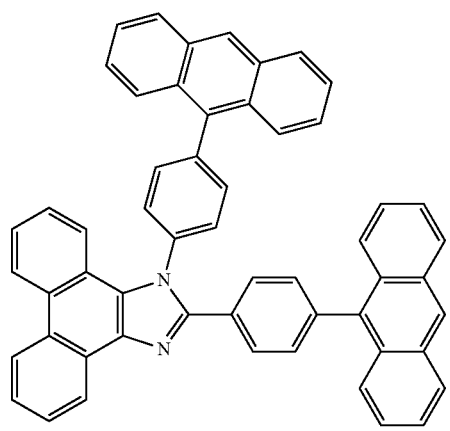

-continued
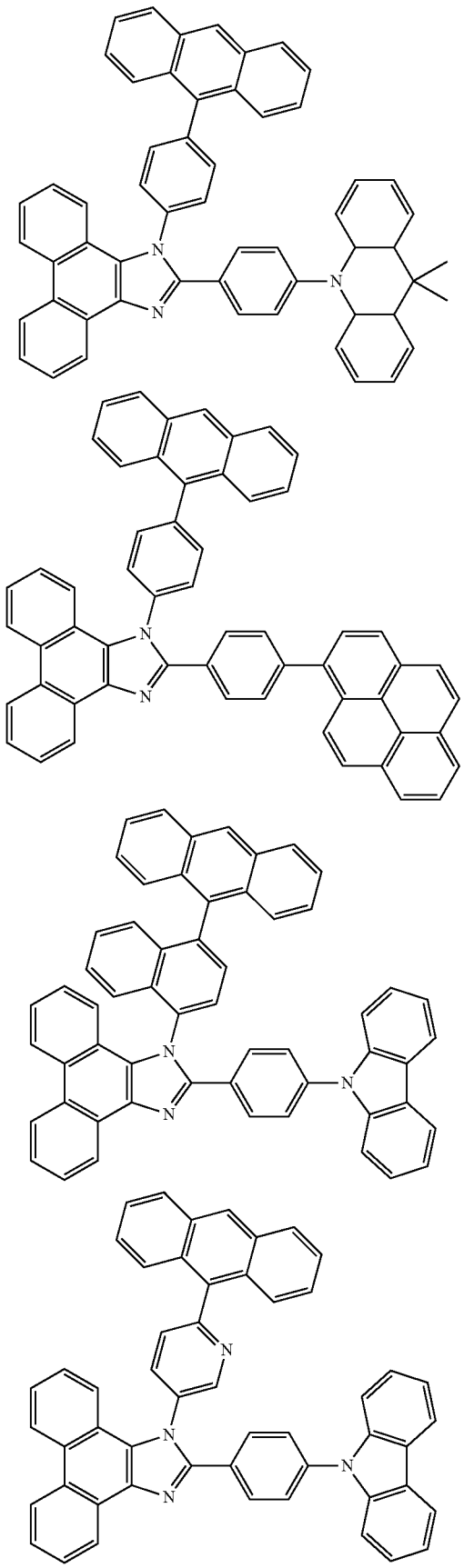
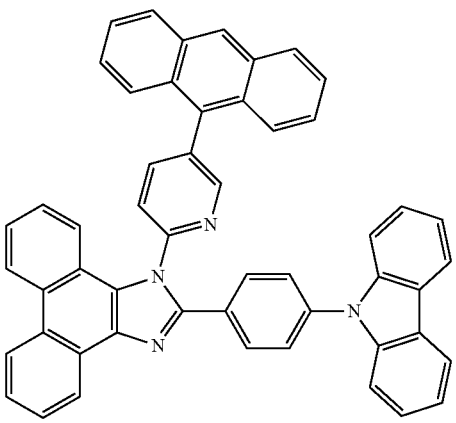
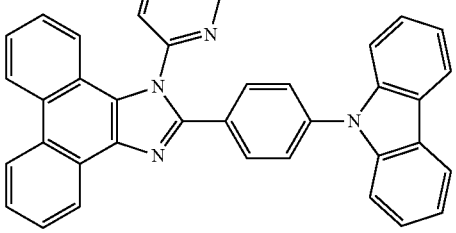
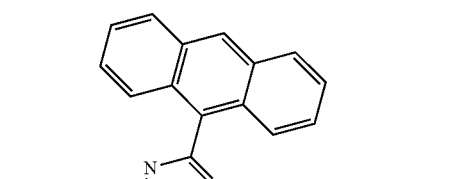
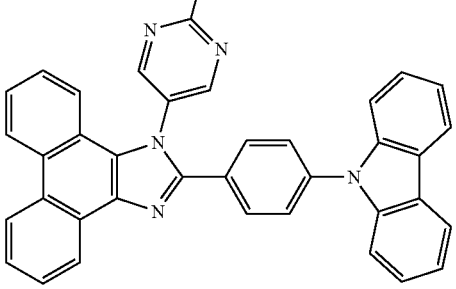
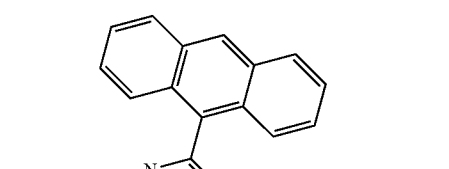
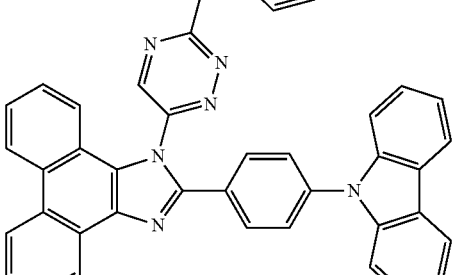
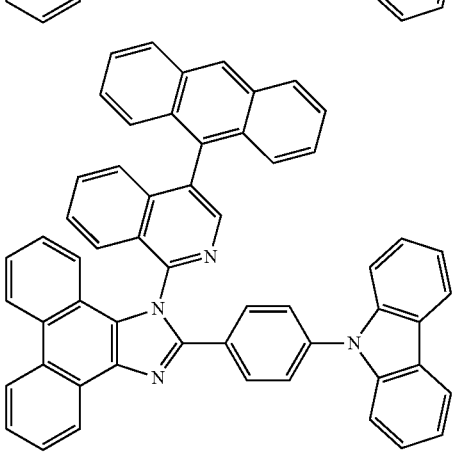

-continued
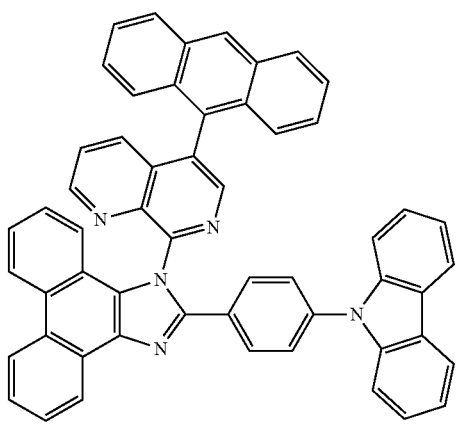
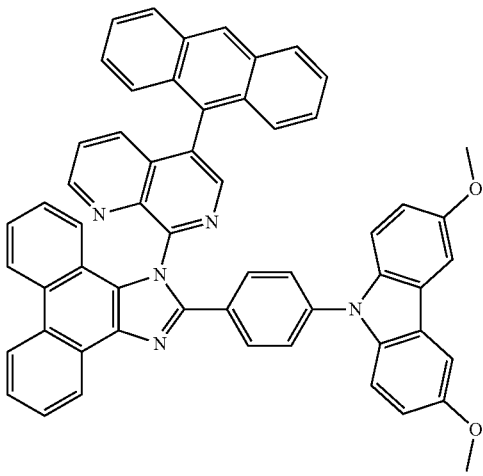
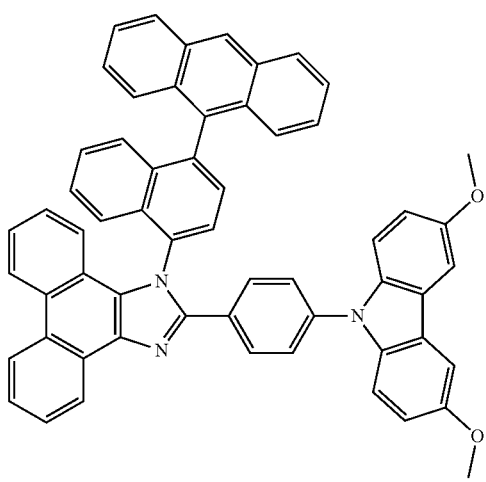
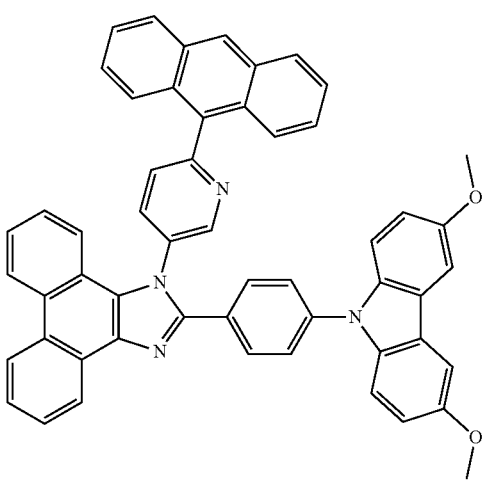
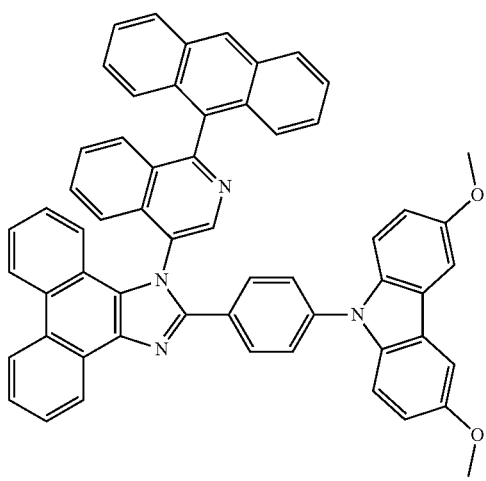
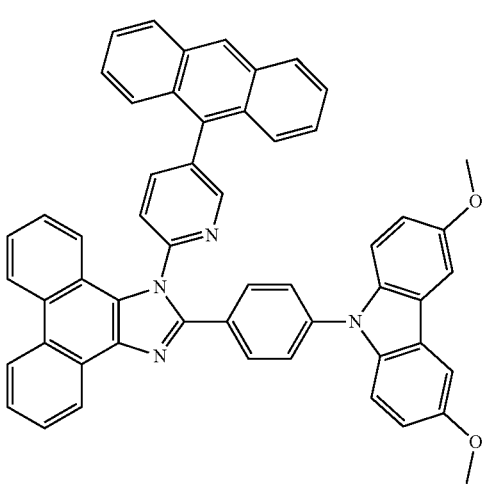

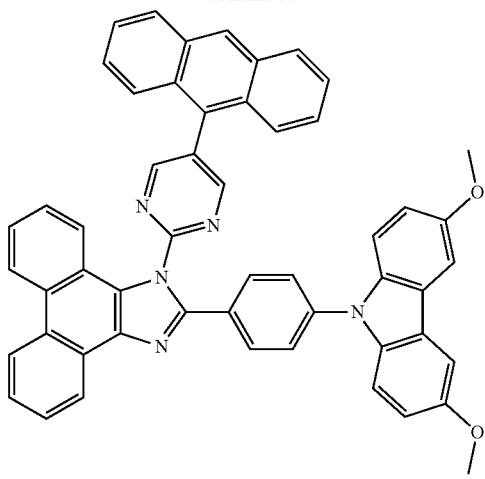
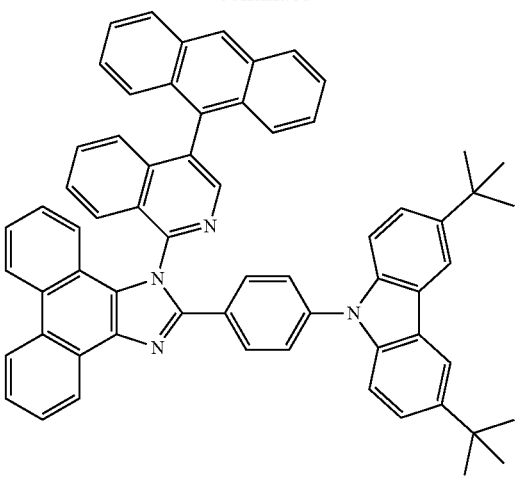
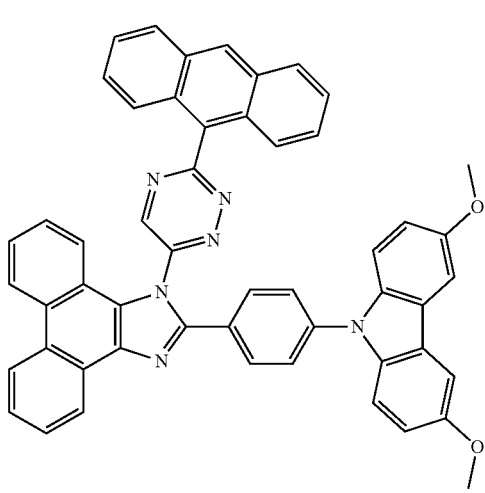
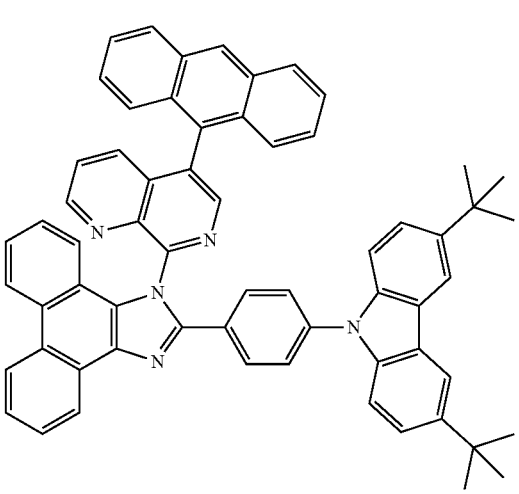
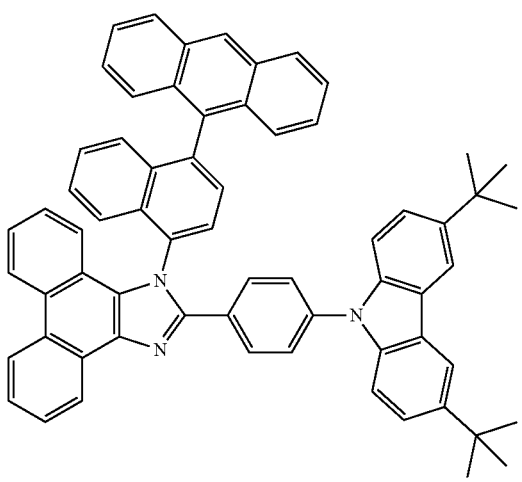
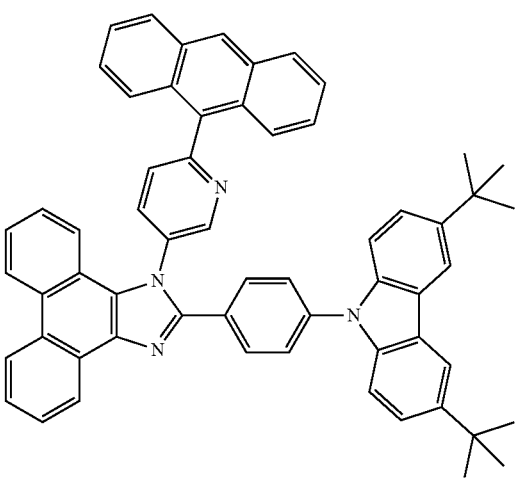

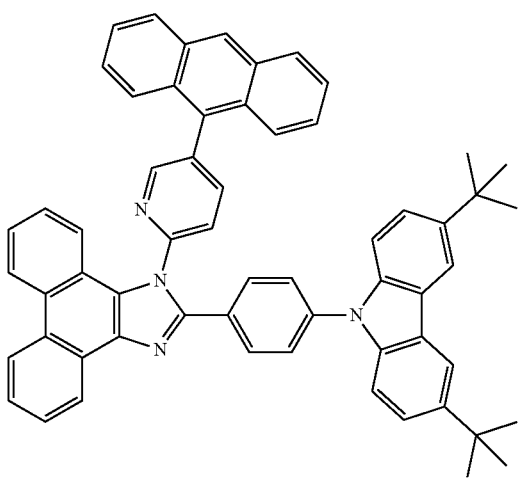
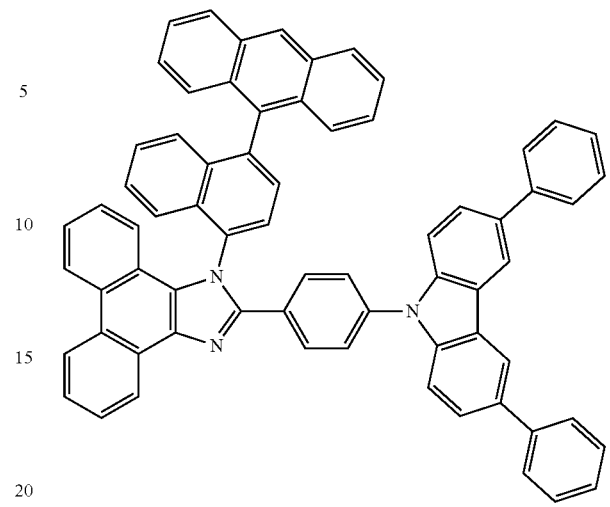
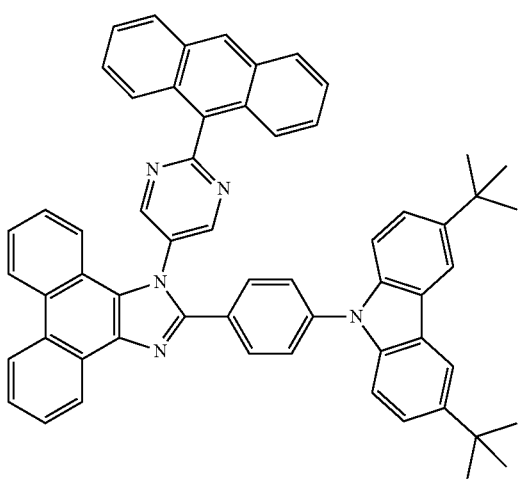
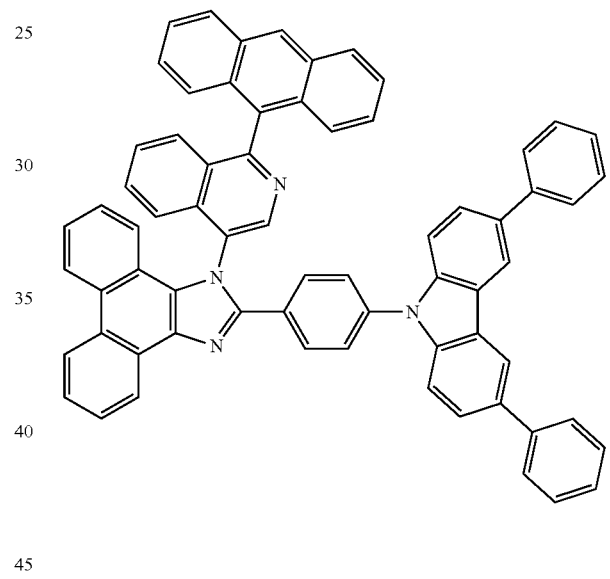
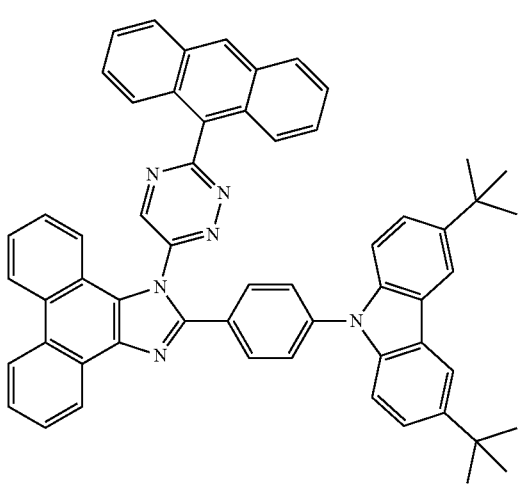
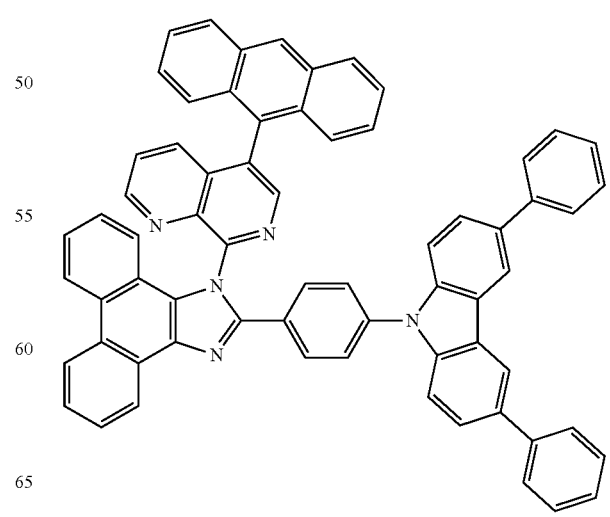

15
-continued
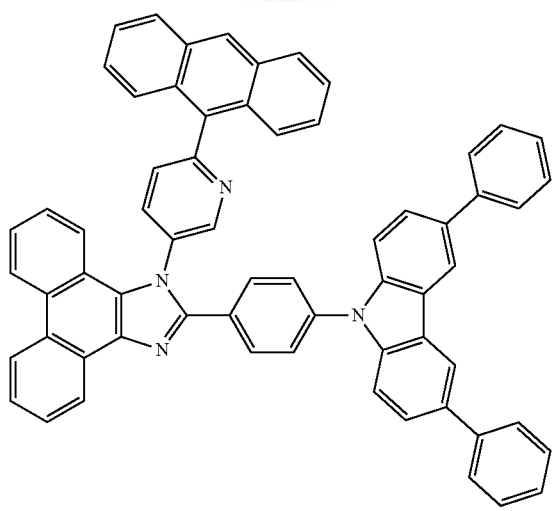
16
-continued
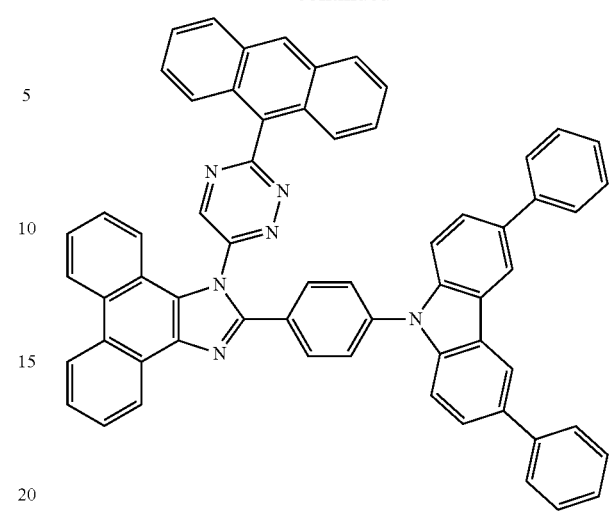
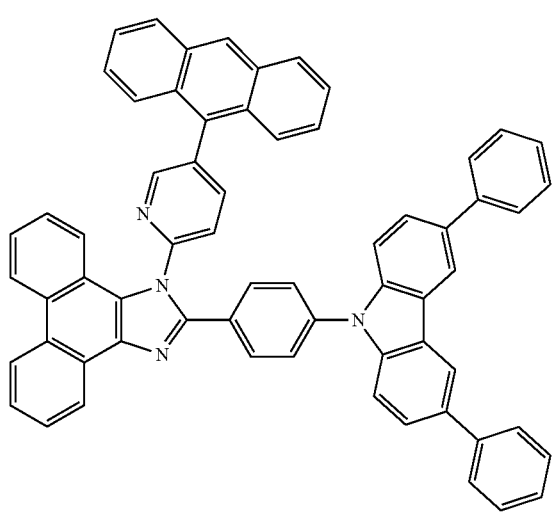
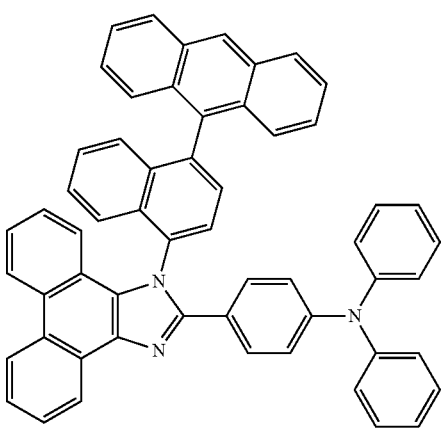
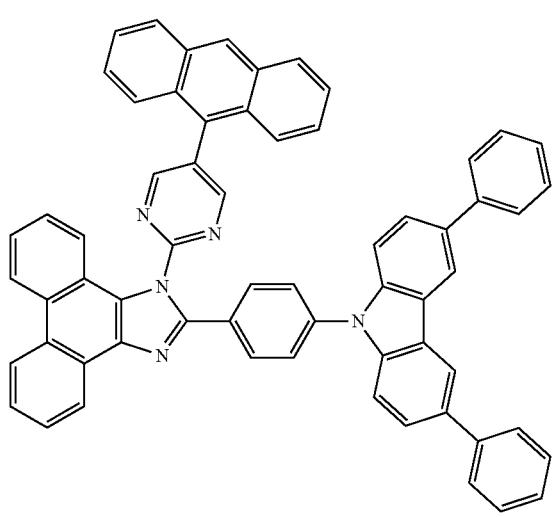
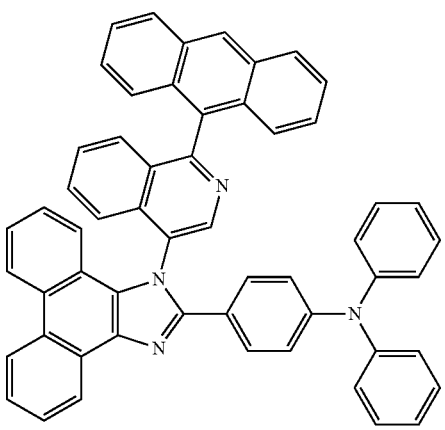

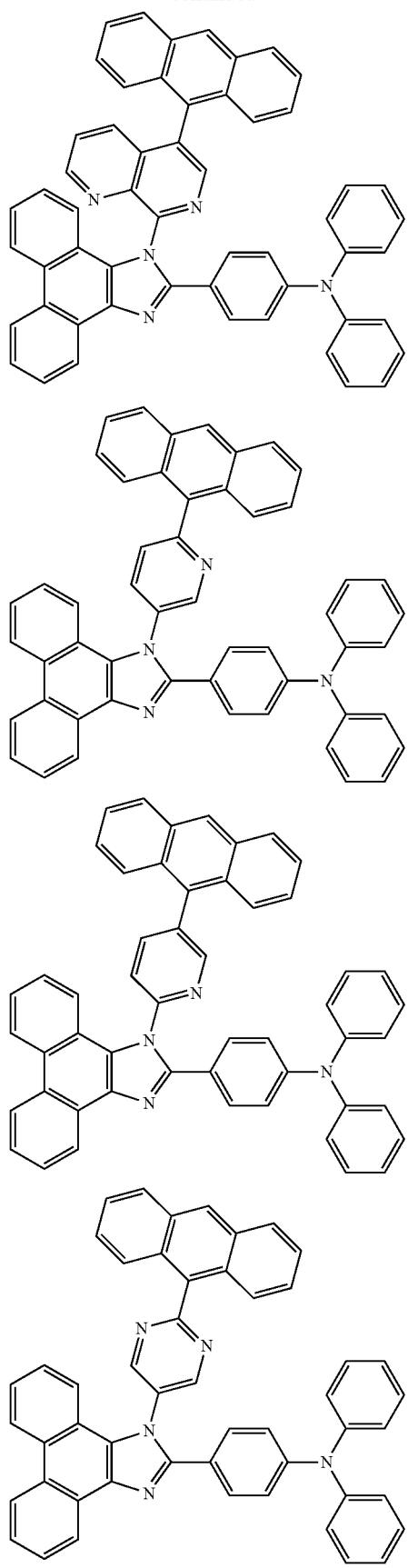
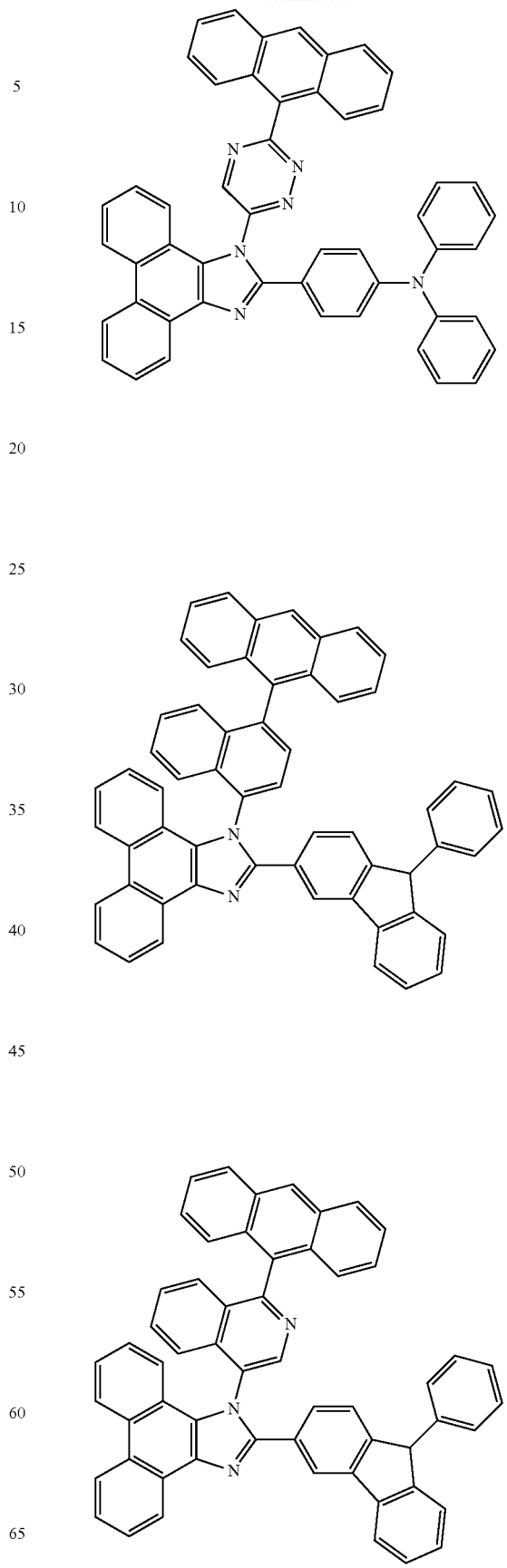

-continued
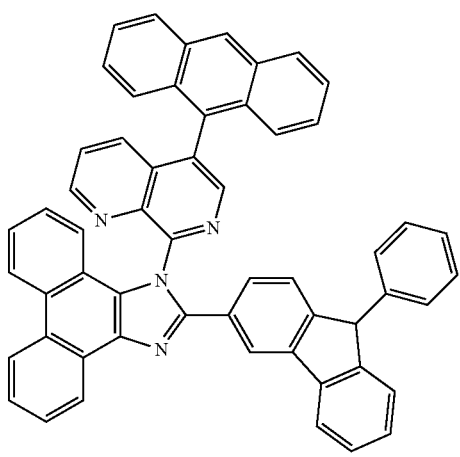
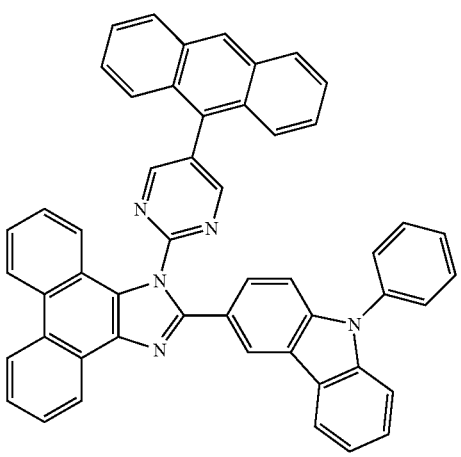
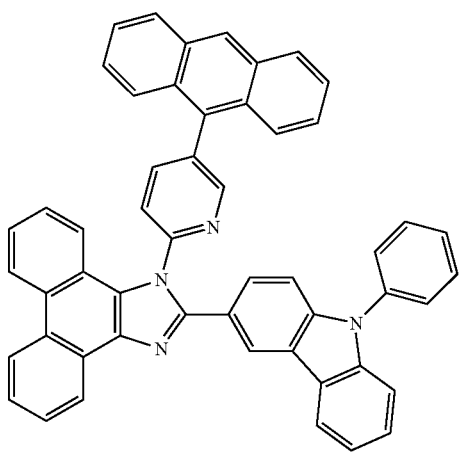
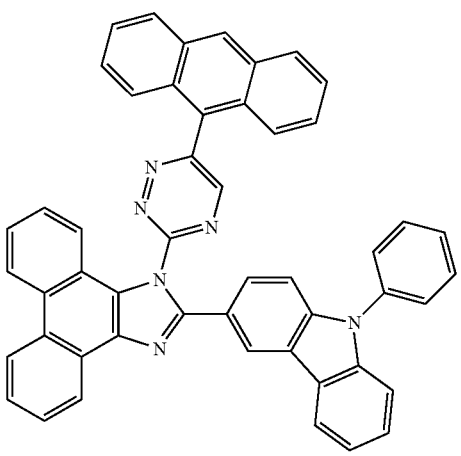
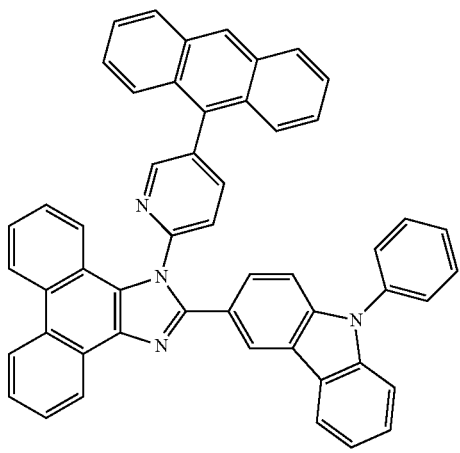
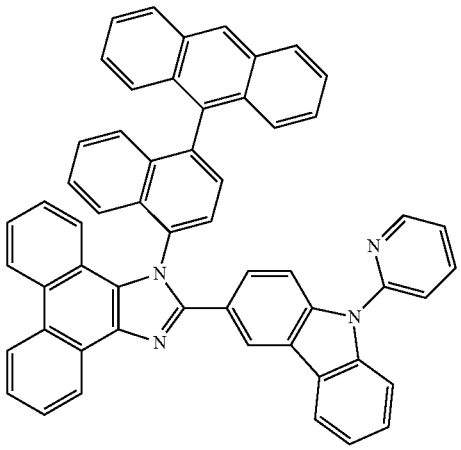

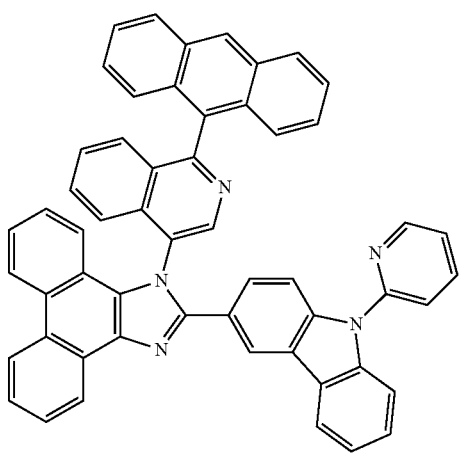
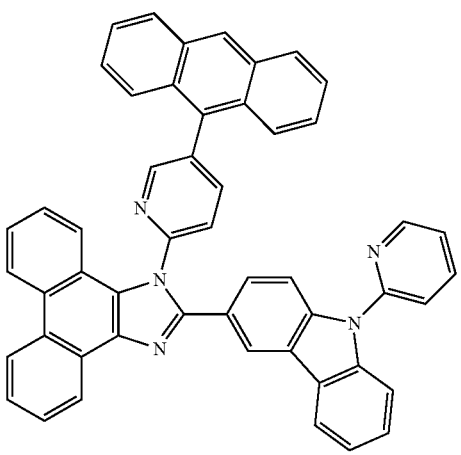
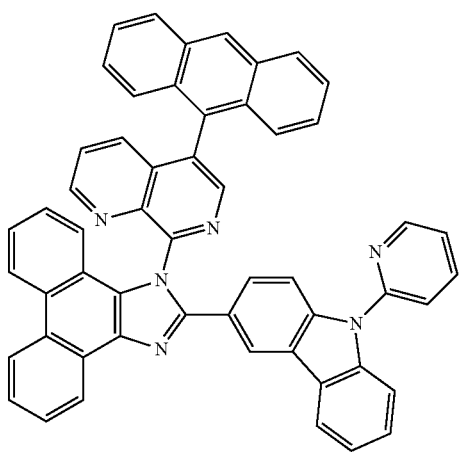
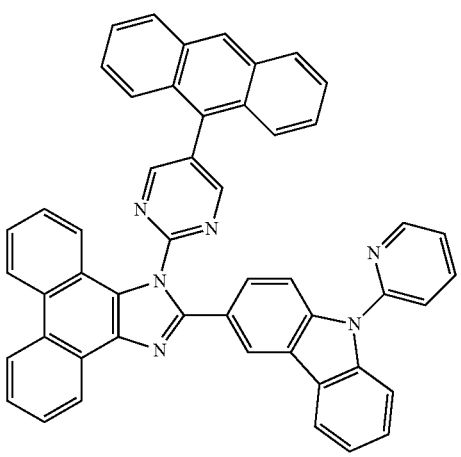
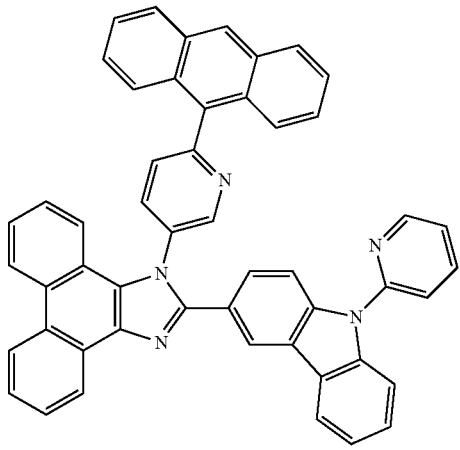
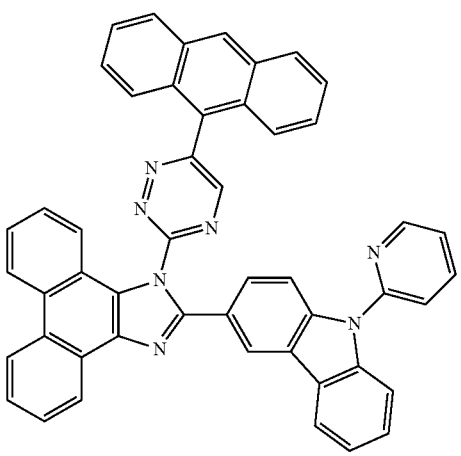

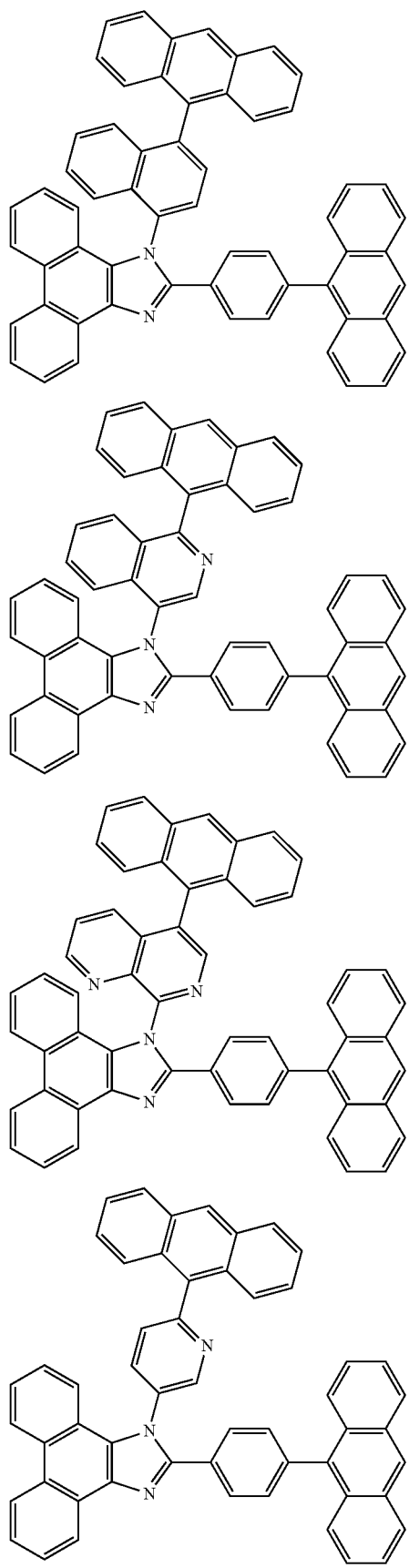
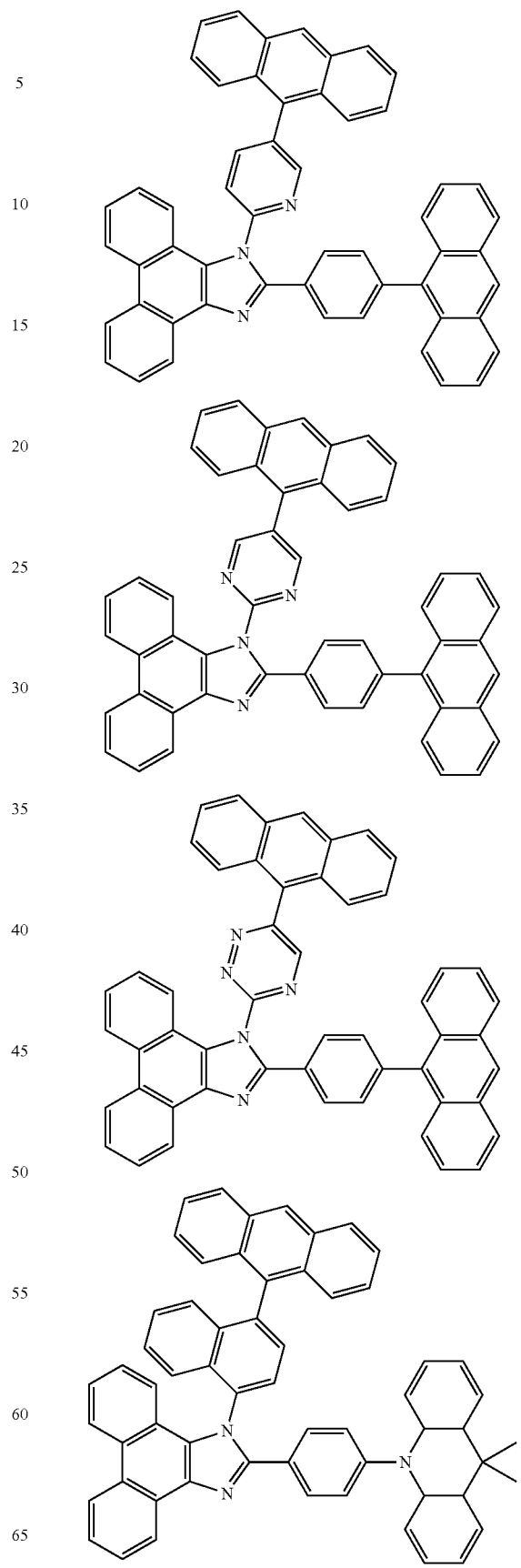

25
-continued
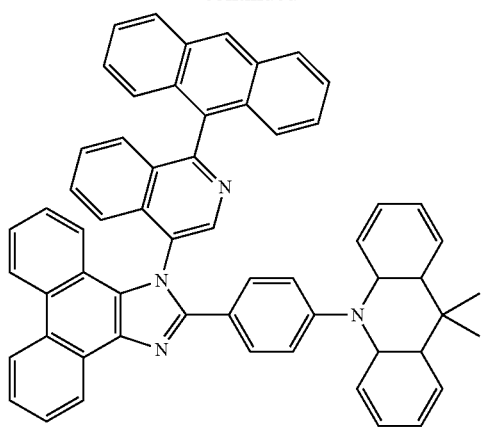
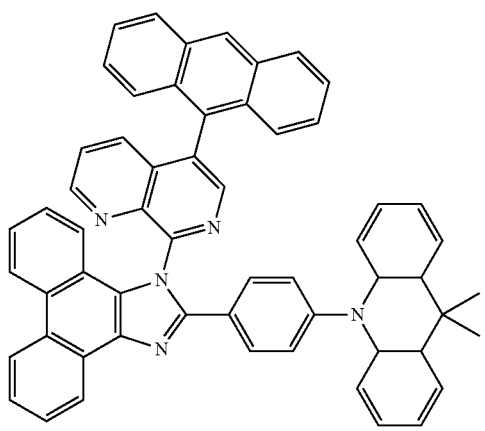
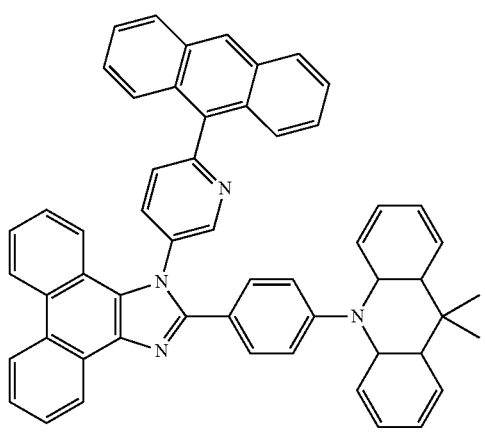
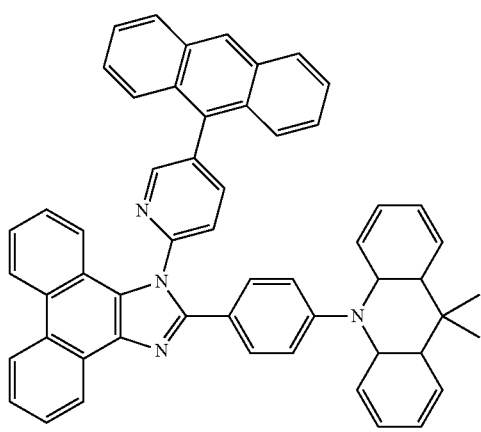
26
-continued
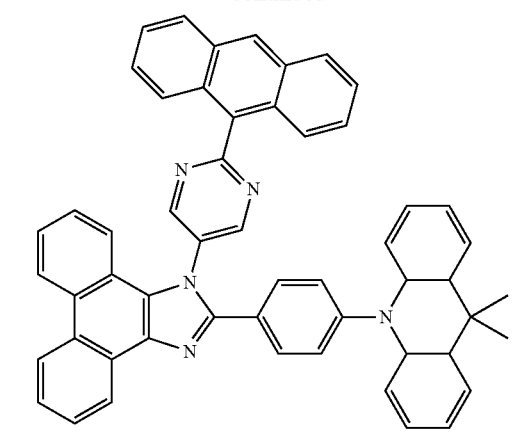
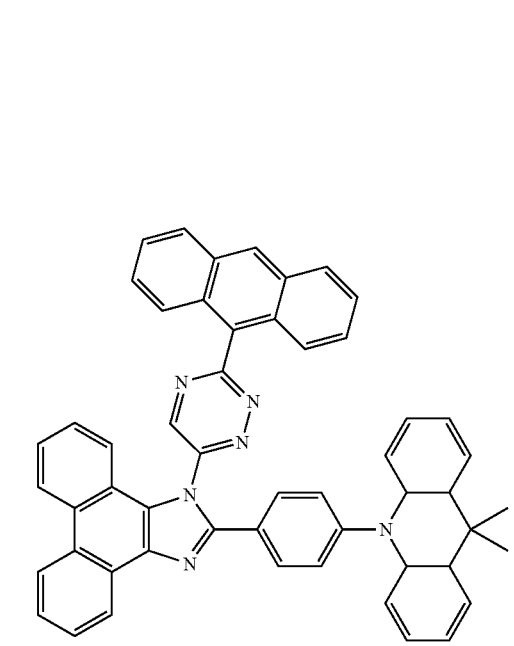

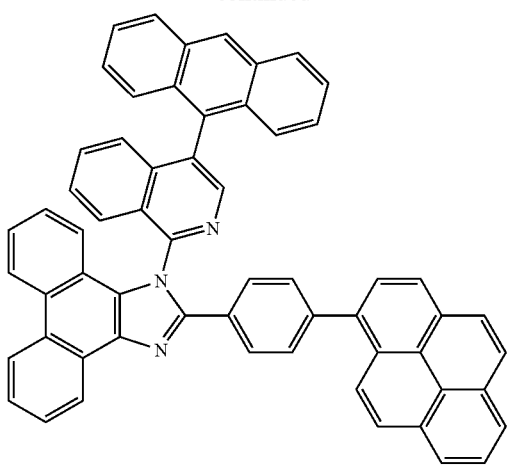

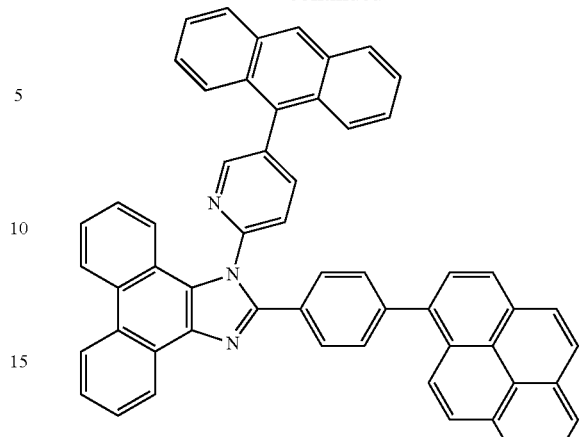

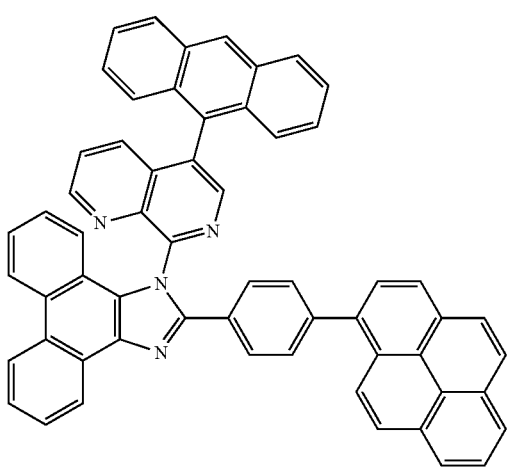

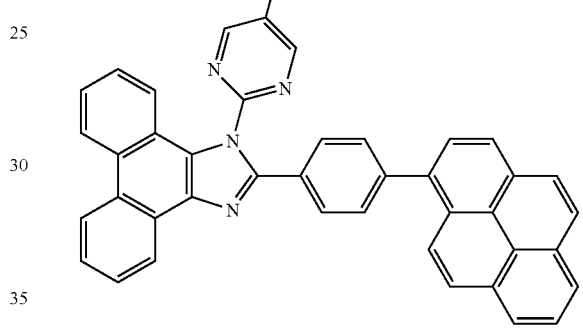

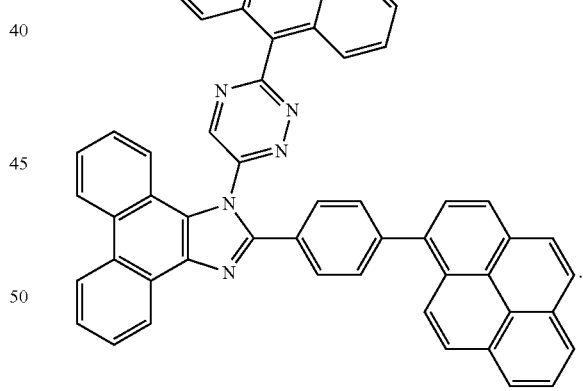

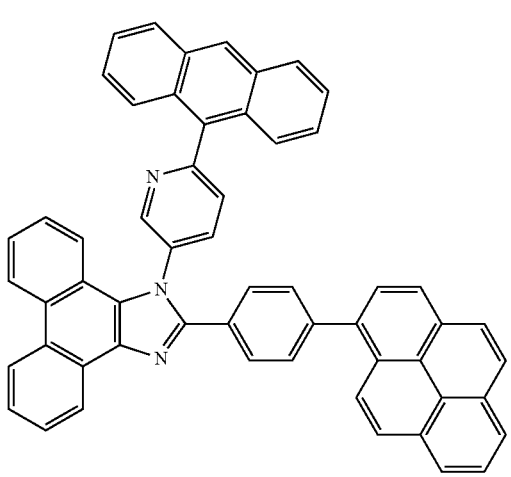 [SMILES: c1ccc2c(-c3ncc(-n4c(-c5ccc(-c6ccc7ccc8cccc9ccc6c7c89)cc5)nc5c6ccccc6c6ccccc6c54)nn3)c3ccccc3cc2c1]

The invention provides an organic light-emitting diode including a cathode, an anode, and a light-emitting layer. The light-emitting layer is disposed between the cathode and the anode, wherein the light-emitting layer contains the above phenanthroimidazole compound.

In an embodiment of the invention, the above organic light-emitting diode is, for instance, a blue light-emitting diode.

In an embodiment of the invention, the above light-emitting layer includes a host light-emitting material and a guest light-emitting material.

In an embodiment of the invention, the above host light-emitting material includes the phenanthroimidazole compound.

In an embodiment of the invention, the above organic light-emitting diode can further include at least one auxiliary layer, and the auxiliary layer is selected from the group consisting of a hole injection layer, a hole transport layer, a hole blocking layer, an electron injection layer, an electron transport layer, and an electron blocking layer.

Based on the above, the phenanthroimidazole compound of the present embodiment has the characteristics of blue light emission, high quantum efficiency, and good thermal stability. Moreover, the phenanthroimidazole compound of the present embodiment has electron-withdrawing groups (phenanthroimidazole group and anthryl group) and an electron-releasing group (the group connected to a carbon atom in an imidazole group). Therefore, the phenanthroimidazole compound of the present embodiment has bipolar characteristics to balance electron and hole transfers so as to lower the driving voltage of the resulting device. Moreover, the light-emitting layer of the organic light-emitting diode of the present embodiment includes a phenanthroimidazole compound, and therefore has high external quantum efficiency and low driving voltage.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
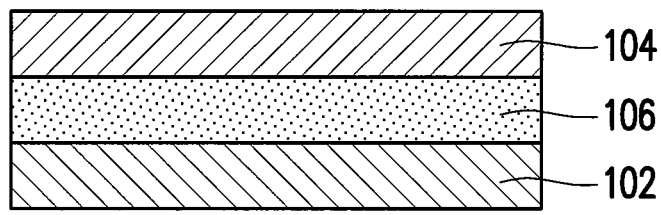
FIG. 1 is a cross-sectional schematic diagram of an organic light-emitting diode according to an embodiment of the invention.

In the following, embodiments of the invention are described in detail. However, the embodiments are exemplary, and the disclosure is not limited thereto.

In the present specification,  indicates a portion connected to another substituent.

In the present specification, unless otherwise specified, the term "substituted" refers to substitution by the following groups: halogen, an aryl group, a hydroxyl group, an alkenyl group, a $C_1$ to $C_{20}$ alkyl group, an alkynyl group, a cyano group, a trifluoromethyl group, an alkylamino group, an amine group, a $C_1$ to $C_{20}$ alkoxy group, a heteroaryl group, an aryl group having a halogen substituent, an aralkyl group having a halogen substituent, an aryl group having a haloalkyl substituent, an aralkyl group having a haloalkyl substituent, a $C_1$ to $C_{20}$ alkyl group having an aryl substituent, a cycloalkyl group, an amine group having a $C_1$ to $C_{20}$ alkyl substituent, an amine group having a haloalkyl substituent, an amine group having an aryl substituent, an amine group having a heteroaryl substituent, a phosphinyloxy group having an aryl substituent, a phosphinyloxy group having a $C_1$ to $C_{20}$ alkyl substituent, a phosphinyloxy group having a haloalkyl substituent, a phosphinyloxy group having a halogen substituent, a phosphinyloxy group having a heteroaryl substituent, a nitro group, a carbonyl group, an arylcarbonyl group, a heteroarylcarbonyl group, or a $C_1$ to $C_{20}$ alkyl group having a halogen substituent.

In the present specification, the term "aryl group" refers to a substituent including a ring having a conjugate p orbital, and the aryl group can be a monocyclic, polycyclic, or fused ring polycyclic functional group.

Specifically, examples of the aryl group include a phenyl group, a phenylene group, a naphthyl group, a naphthylene group, a pyrenyl group, an anthryl group, and a phenanthryl group, but are not limited thereto.

In the present specification, the term "nitrogen-containing heteroaryl group" refers to an aryl group including at least one N atom in a functional group.

Specifically, examples of the nitrogen-containing heteroaryl group include pyridine, pyrimidine, pyridazine, imidazole, pyrazole, diazine, triazine, tetrazine, isoquinoline, quinoline, quinazoline, quinoxaline, naphthyridine, acridine, phenanthridine, and similar groups, but are not limited thereto.

The aromatic compound according to an embodiment of the invention is represented by the following chemical formula 1:

[Chemical formula 1]

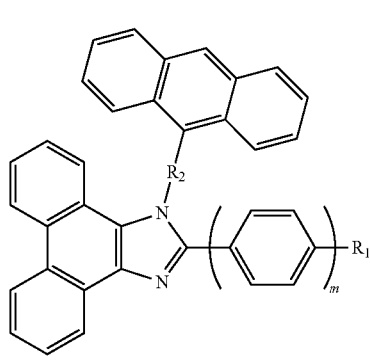

in chemical formula 1, m is an integer of 0 or 1;

when m is 0, $R_1$ is a substituted or unsubstituted carbazolyl group;

when m is 1, $R_1$ is a substituted or unsubstituted carbazolyl group, a substituted or unsubstituted amine group, a substituted or unsubstituted anthryl group, a substituted or unsubstituted pyrenyl group, or a substituted or unsubstituted

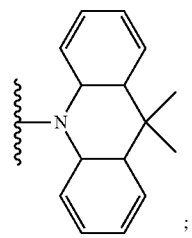 [SMILES: *N1C2C=CC=CC2C(C)(C)C2C=CC=CC21]

and

R$_2$ is a substituted or unsubstituted arylene group or a substituted or unsubstituted nitrogen-containing heteroarylene group.

In an embodiment of the invention, when m is 0, R$_1$ is, for instance, a carbazole group substituted by an aryl group or a heteroaryl group.

In an embodiment of the invention, R$_1$ is, for instance, any one selected from the following structures:

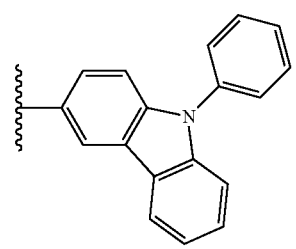

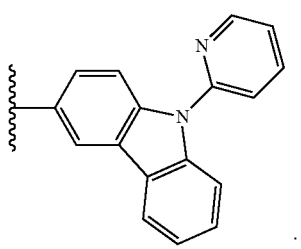

In an embodiment of the invention, when m is 1, R$_1$ is, for instance, a carbazole group, a carbazole group substituted by an alkyl group, an aryl group, or an alkoxy group, or an amine group substituted by an aryl group, anthryl group, pyrenyl group, or

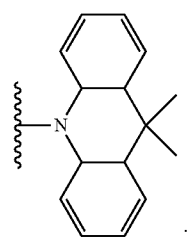 [SMILES: *N1C2C=CC=CC2C(C)(C)C2C=CC=CC21]

In an embodiment of the invention, when m is 1, R$_1$ is, for instance, any one selected from the following structures:

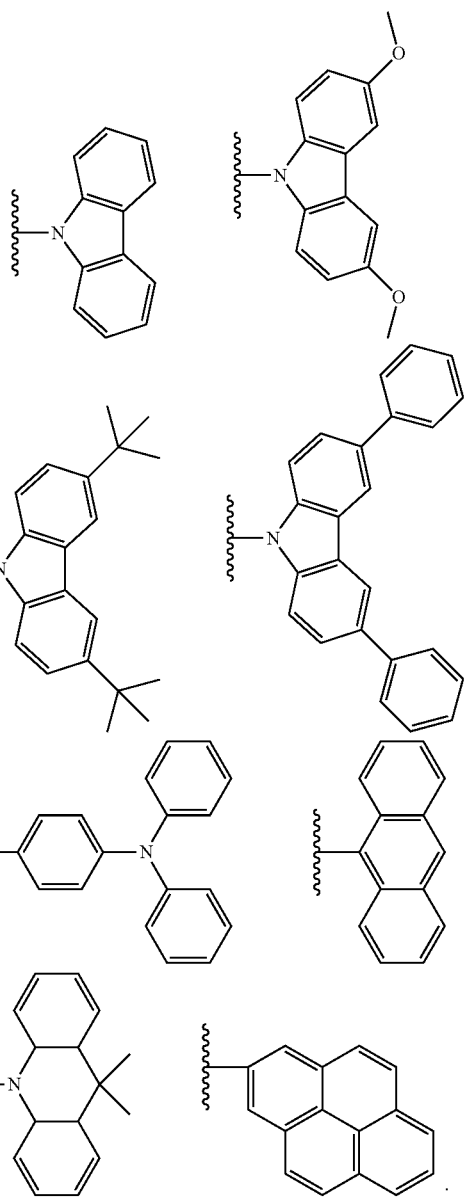

In an embodiment of the invention, R$_2$ is, for instance, any one selected from the following structures:

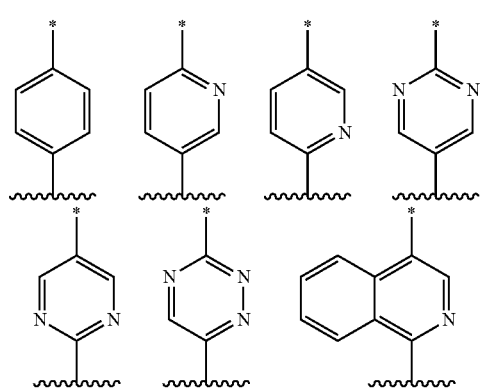

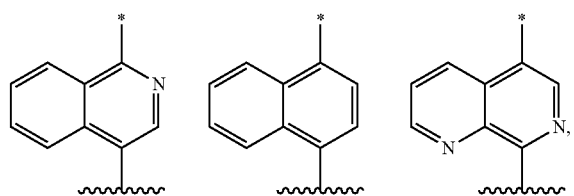
wherein * represents a bonding location with an anthryl group.
In an embodiment of the invention, $R_2$ is, for instance, a phenylene group or a naphthylene group.
In an embodiment of the invention, the phenanthroimidazole compound represented by chemical formula 1 is any one selected from the following structures:
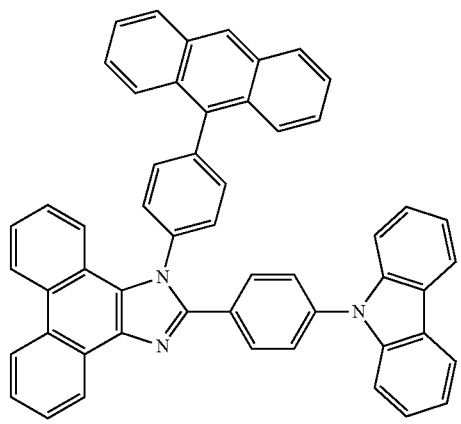
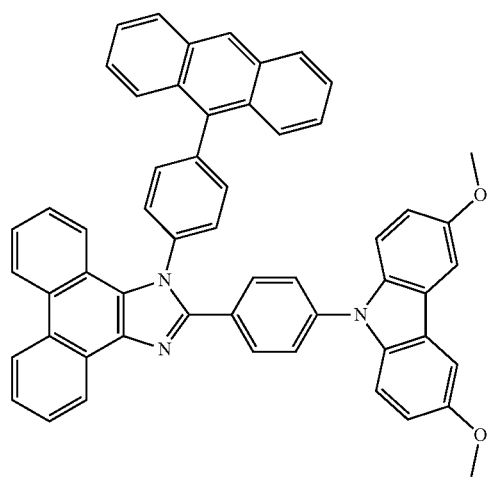
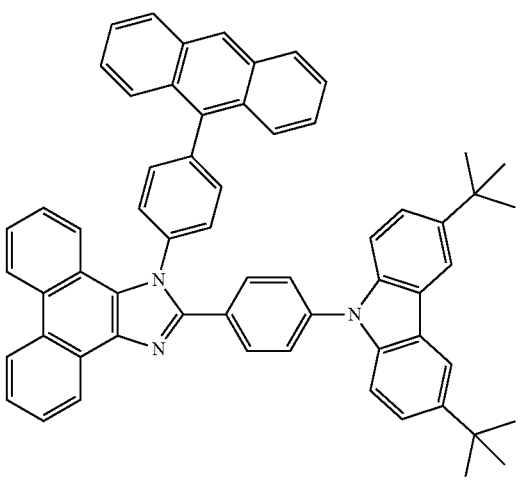
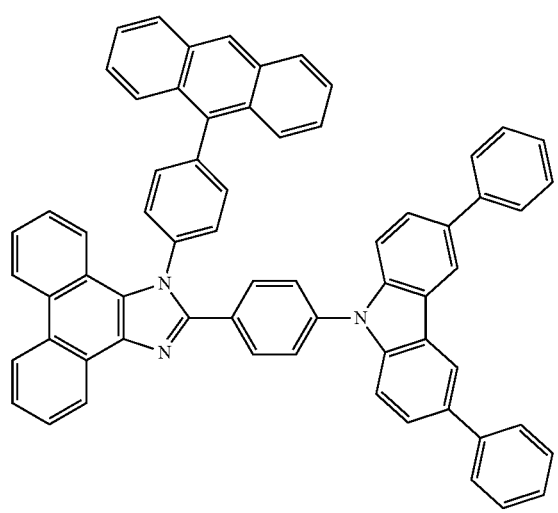
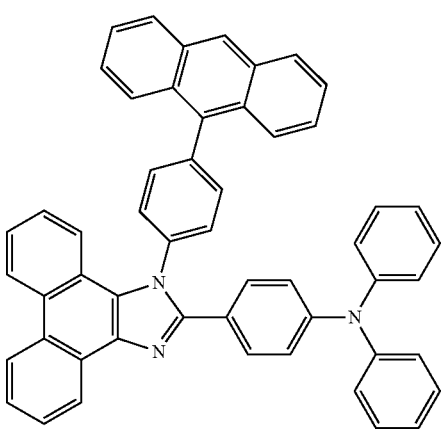

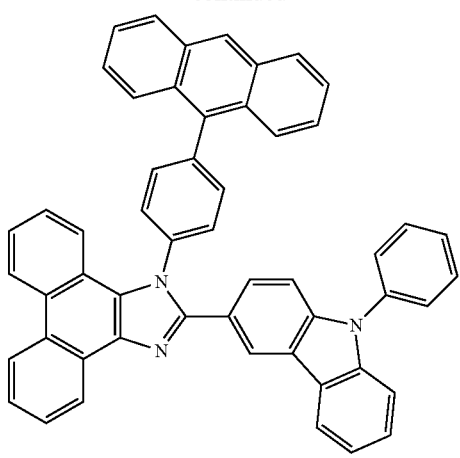
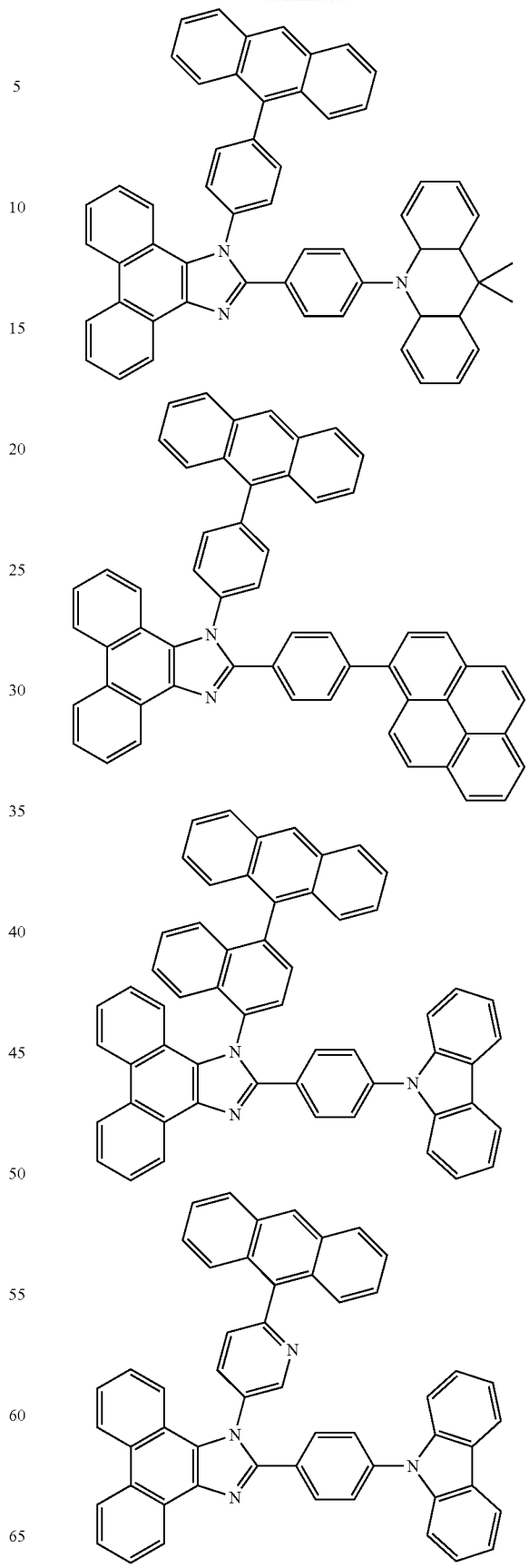

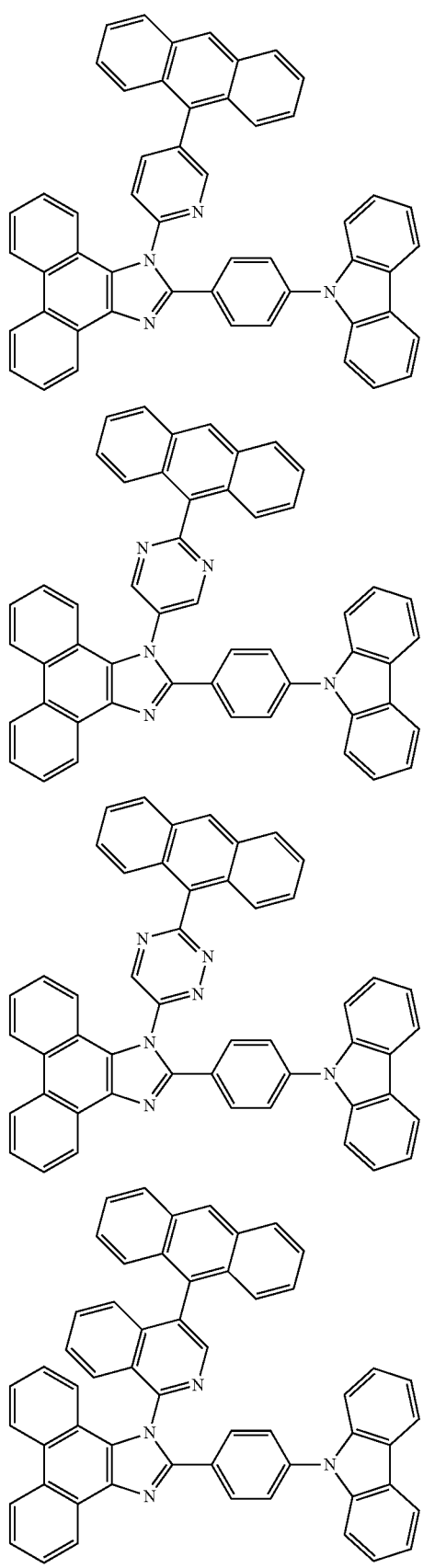
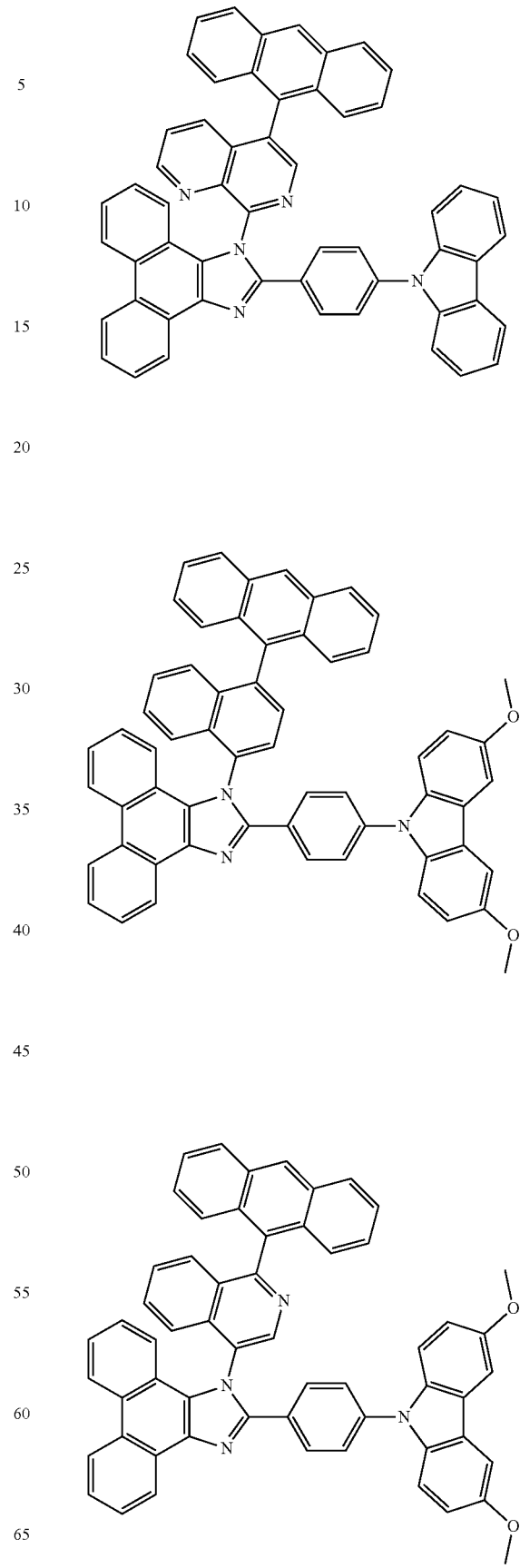

39
-continued
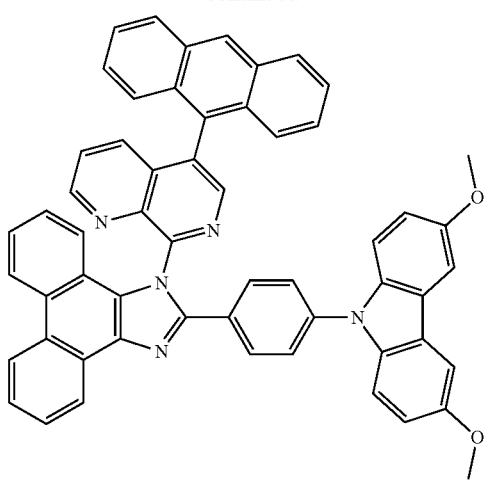
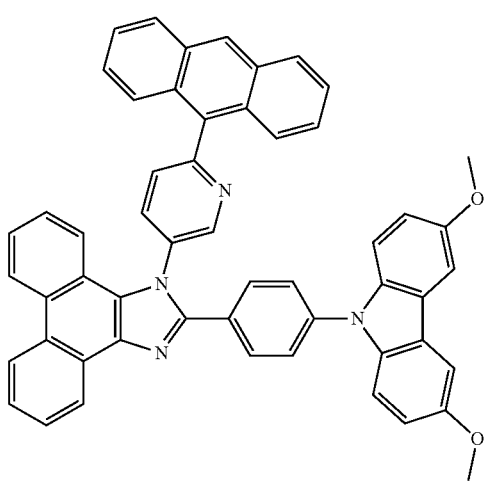
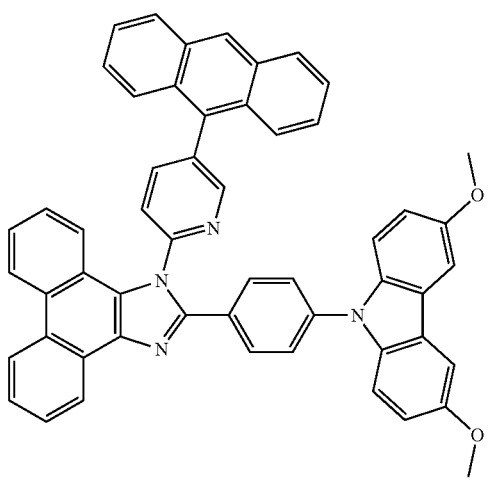
40
-continued
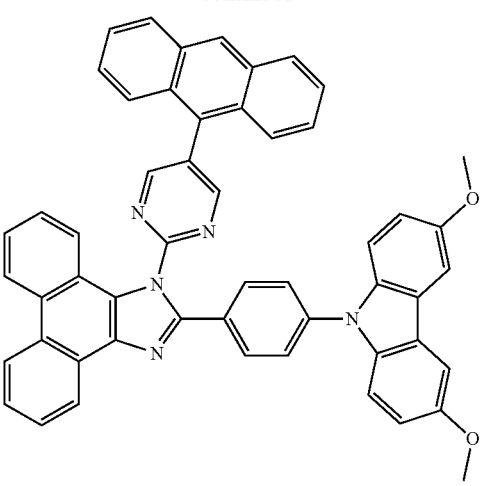
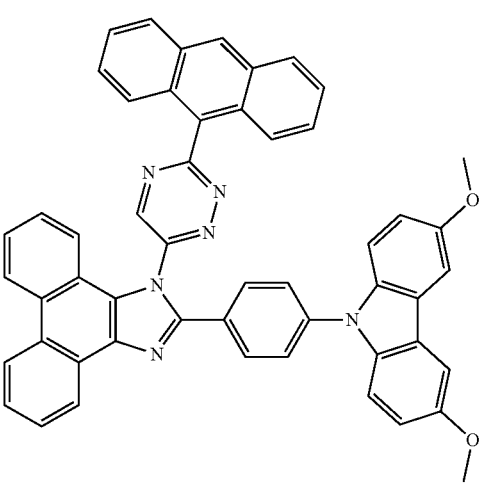
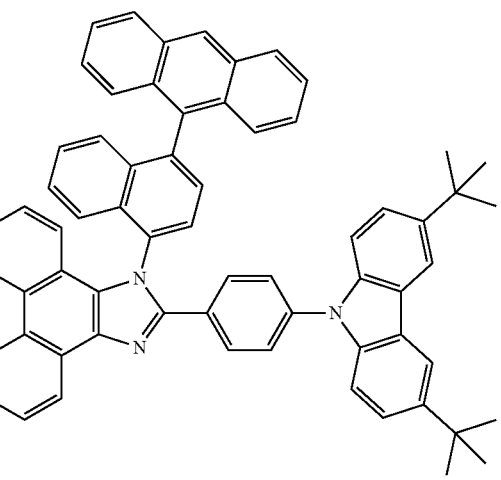

41
-continued
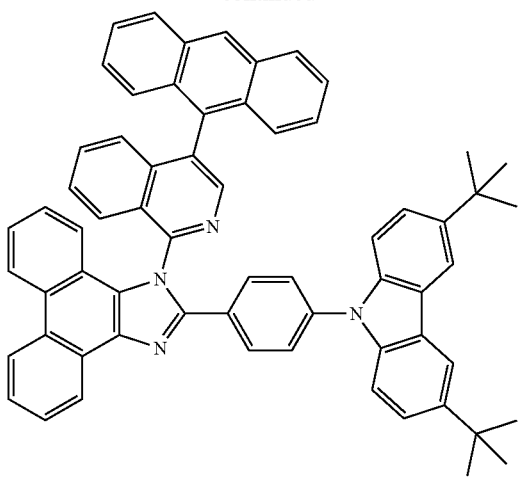
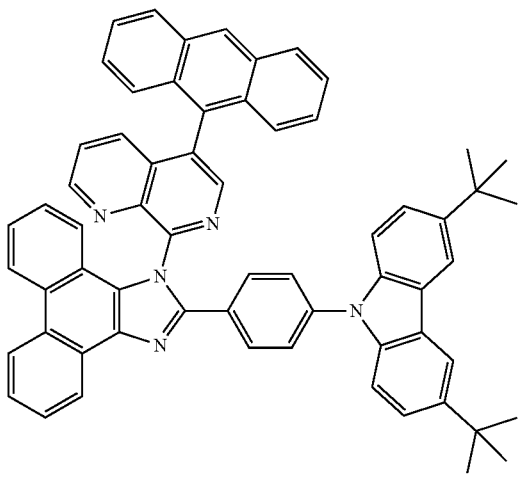
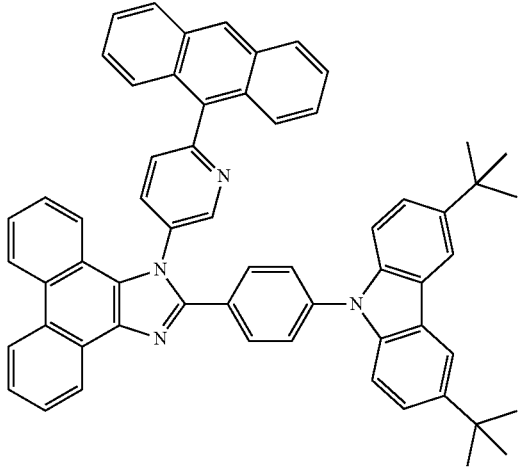
42
-continued
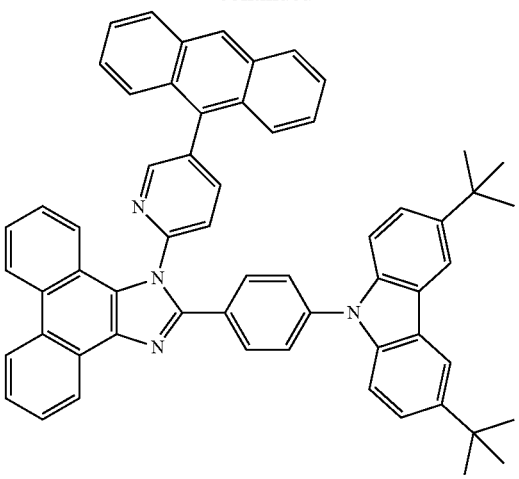
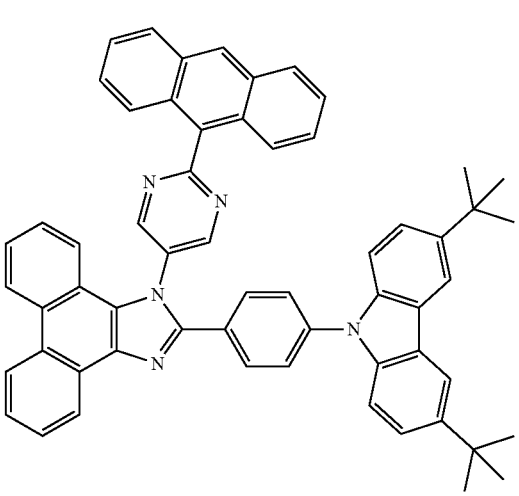
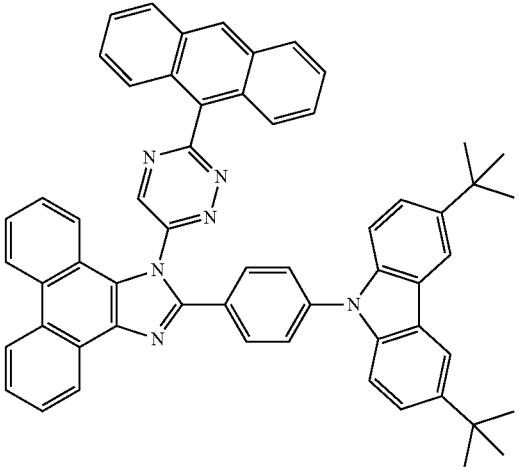

43
-continued
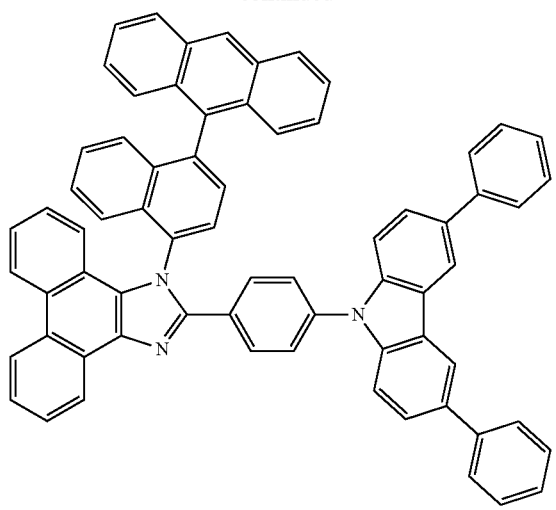
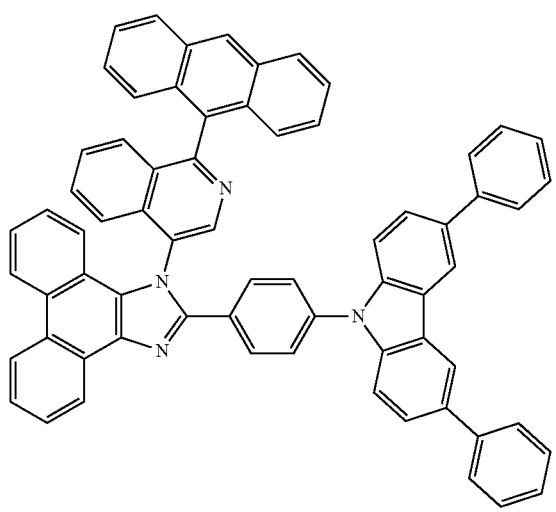
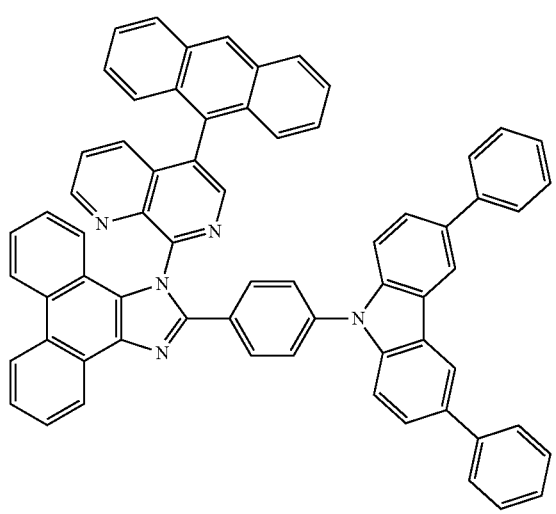
44
-continued
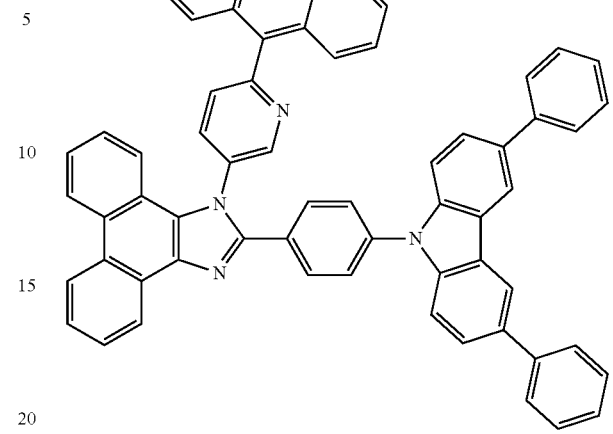
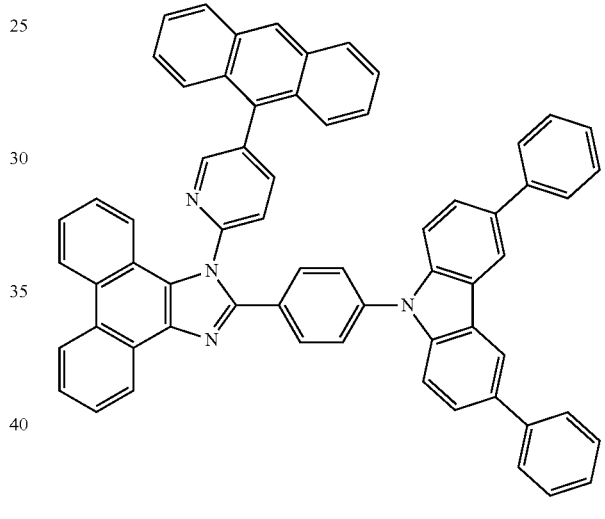
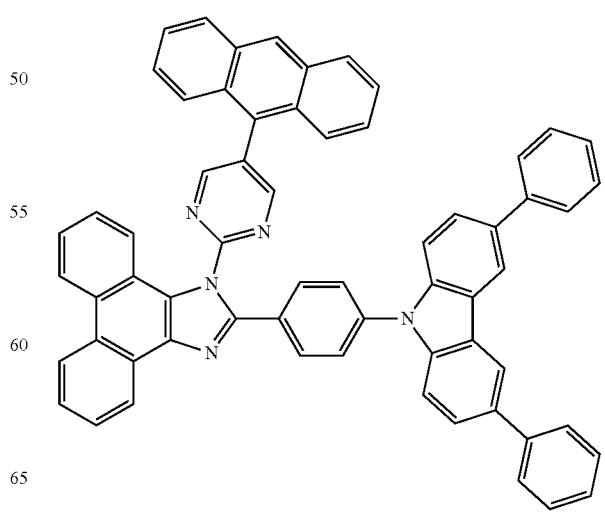

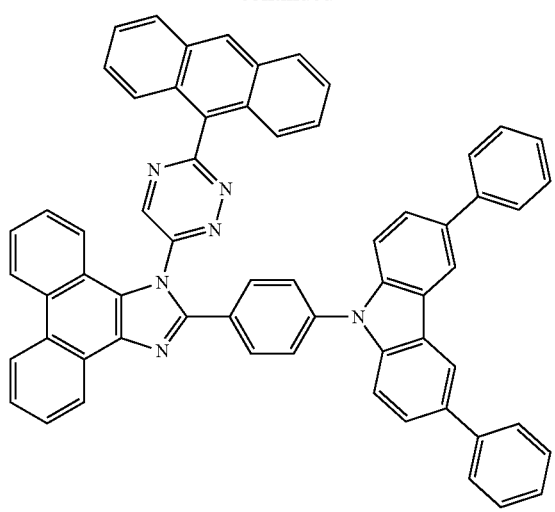
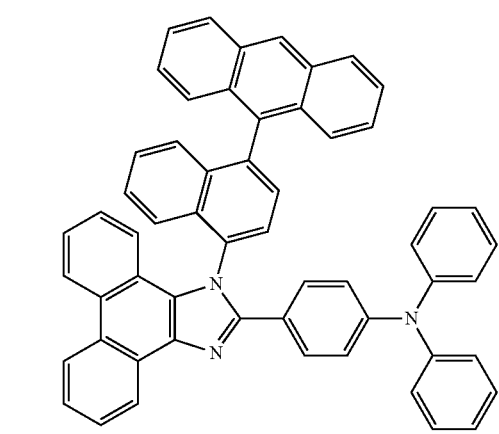
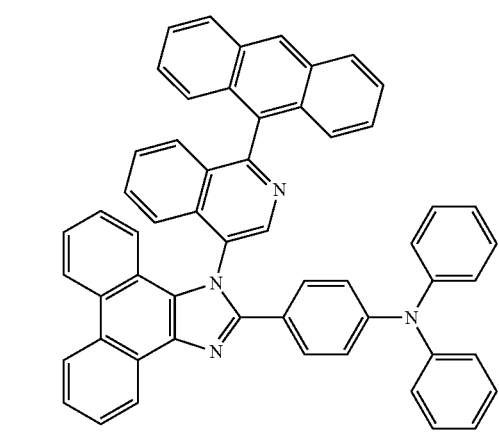
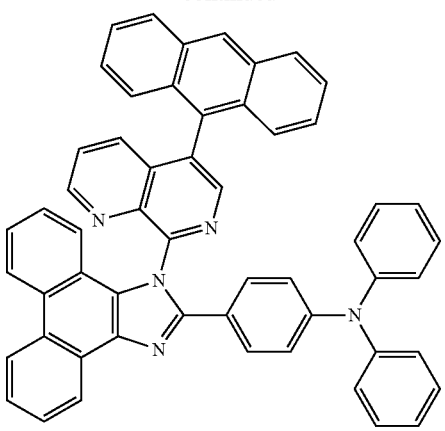
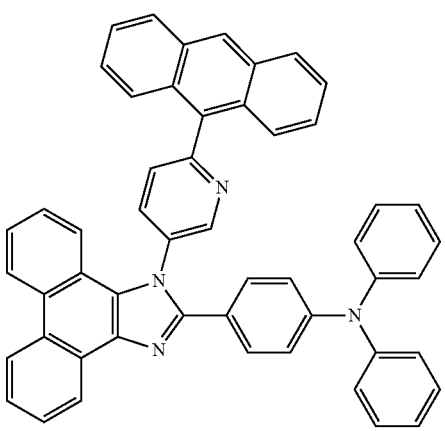
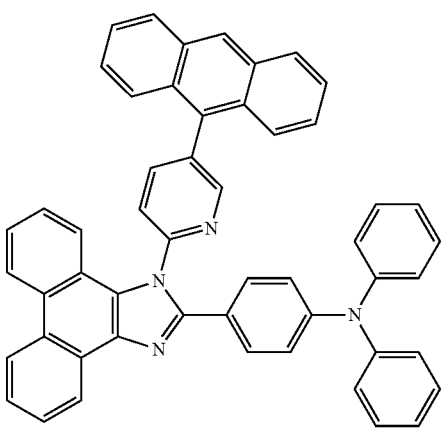
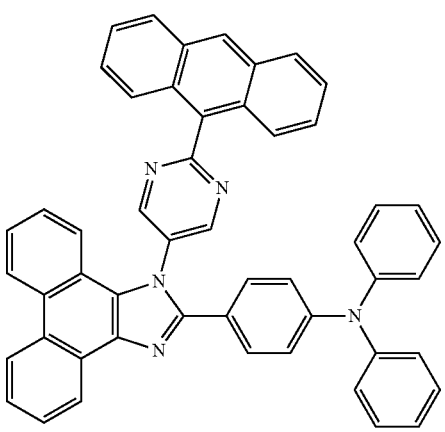

47
-continued
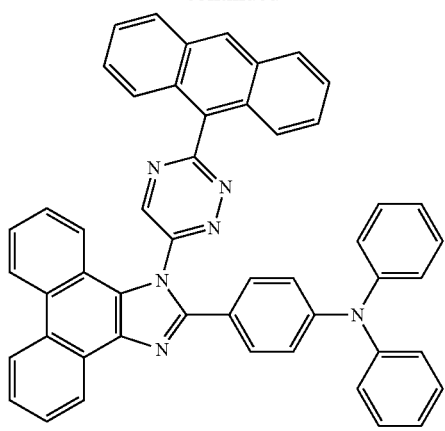
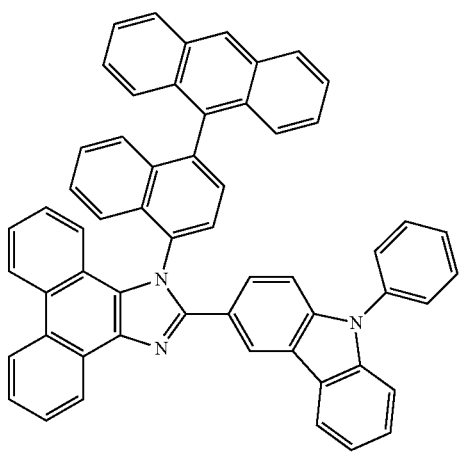
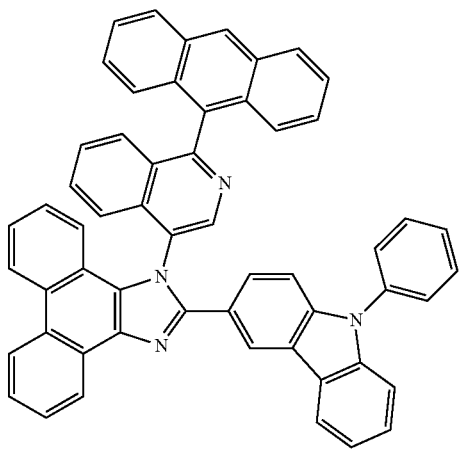
48
-continued
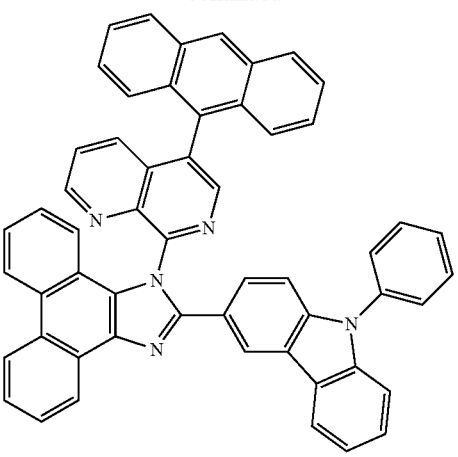
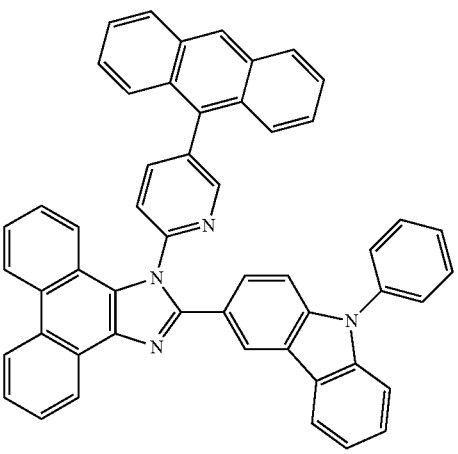
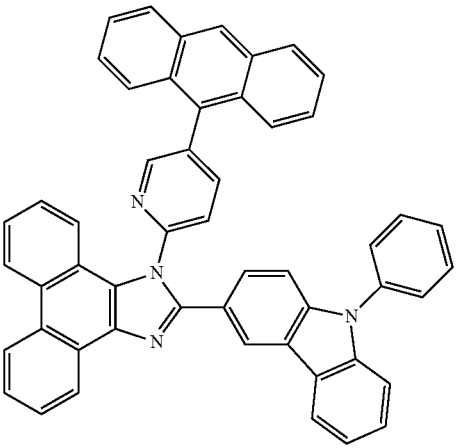

49
-continued
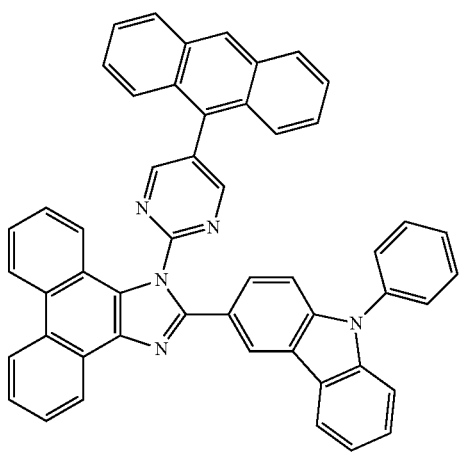
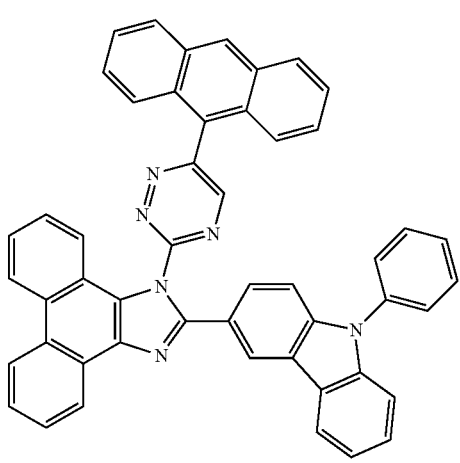
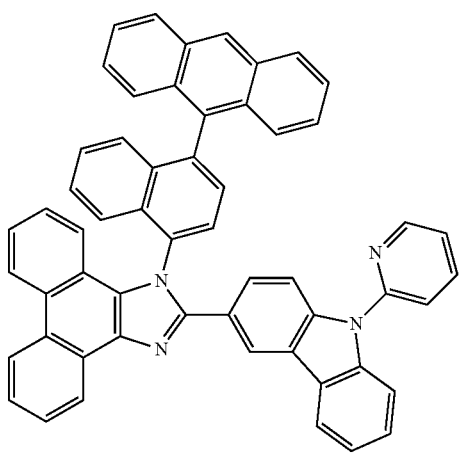
50
-continued
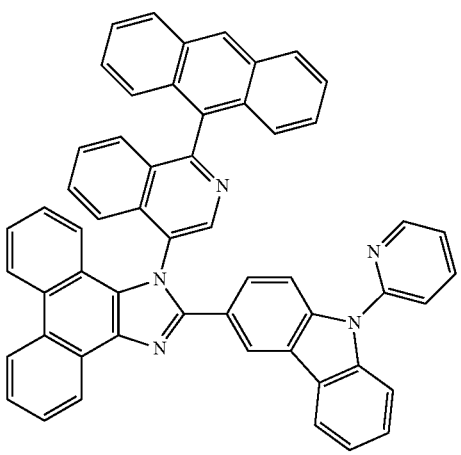
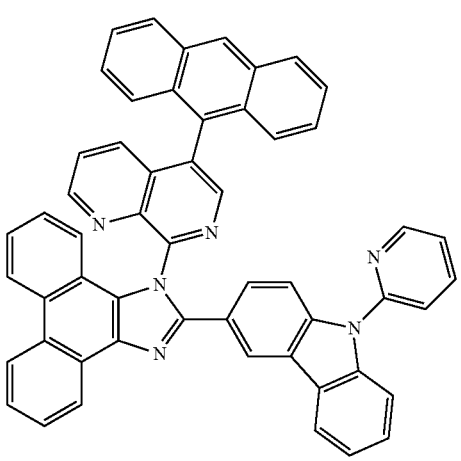
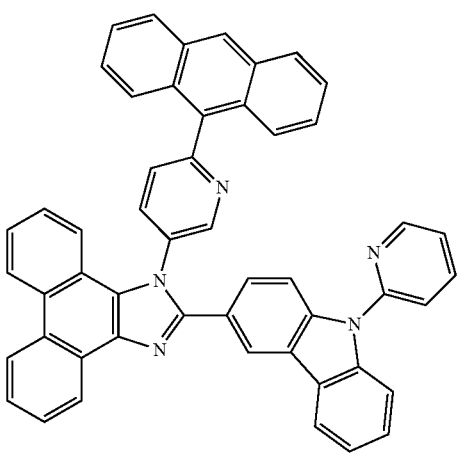

51
-continued
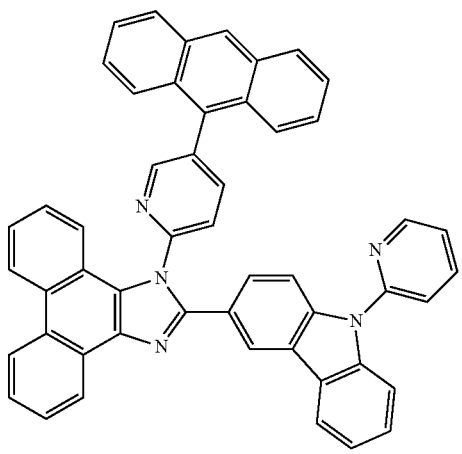
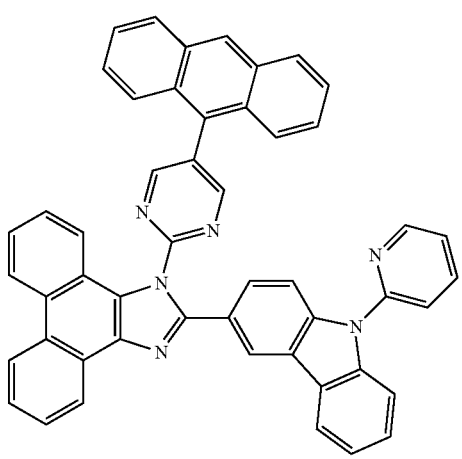
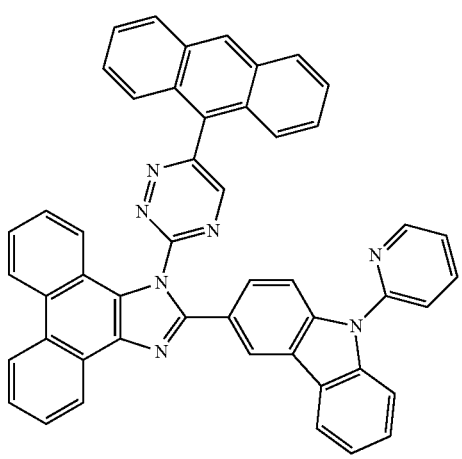
52
-continued
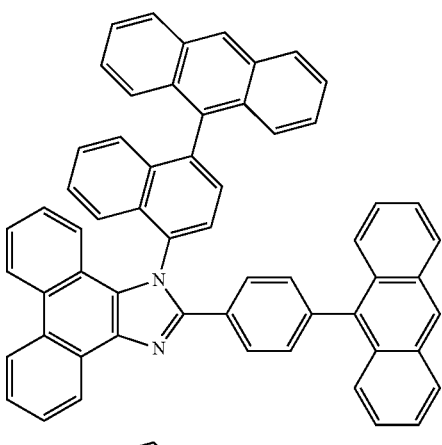
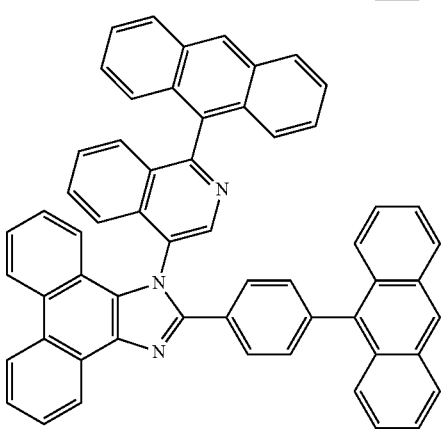
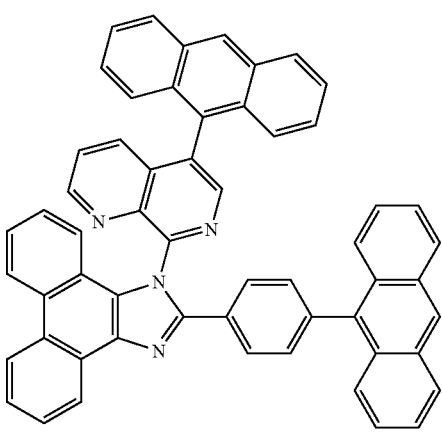

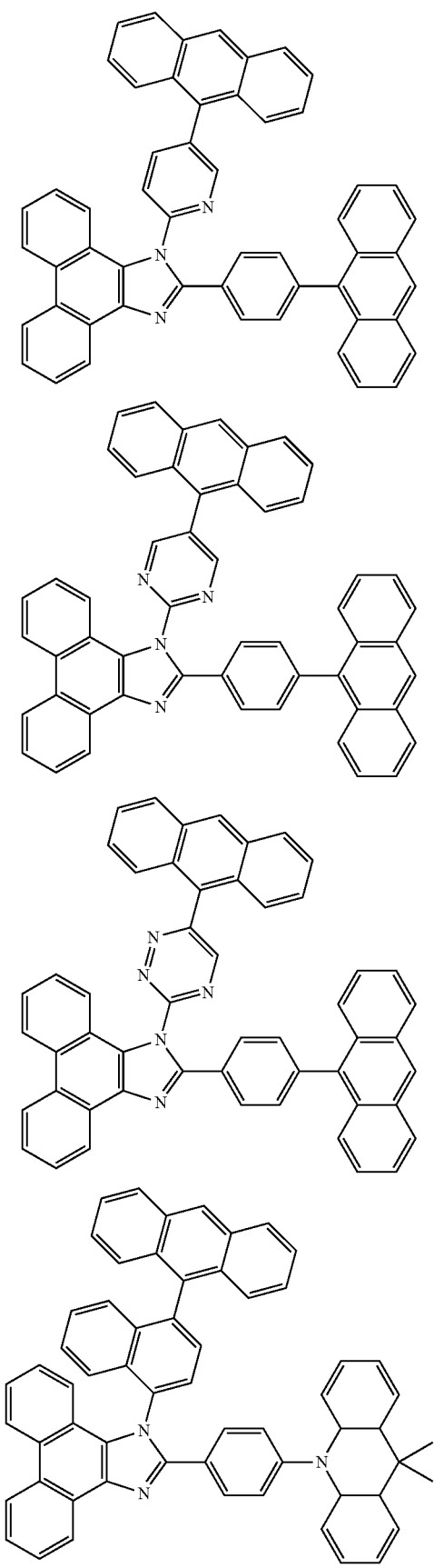
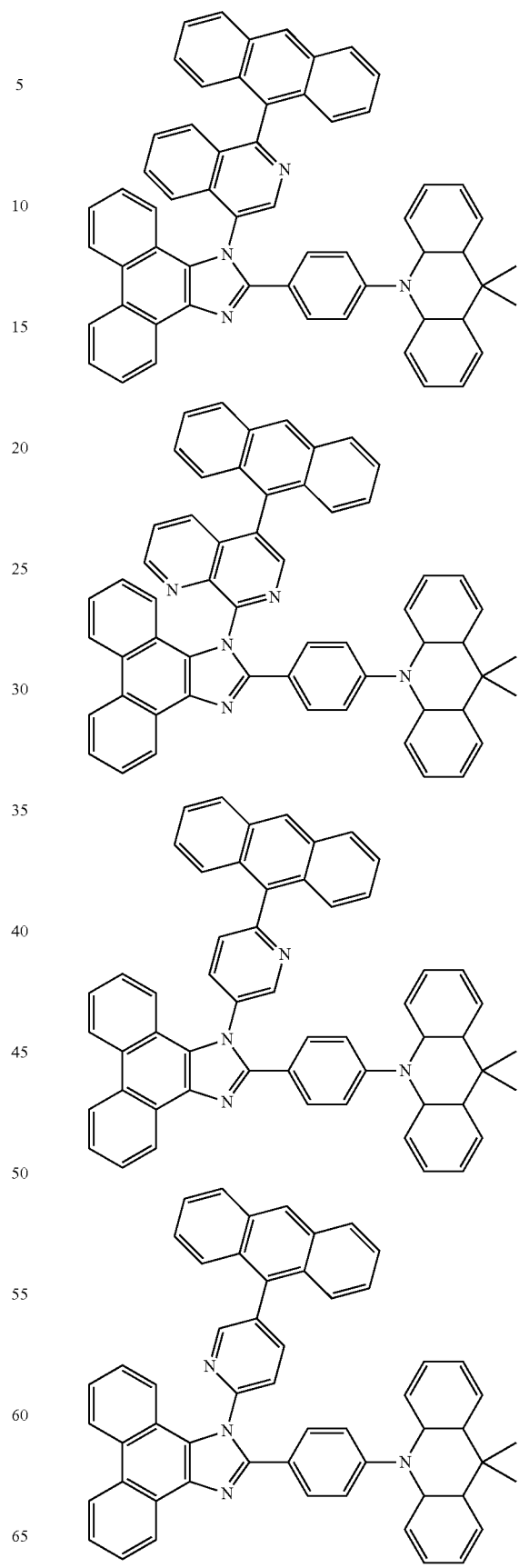

55
-continued
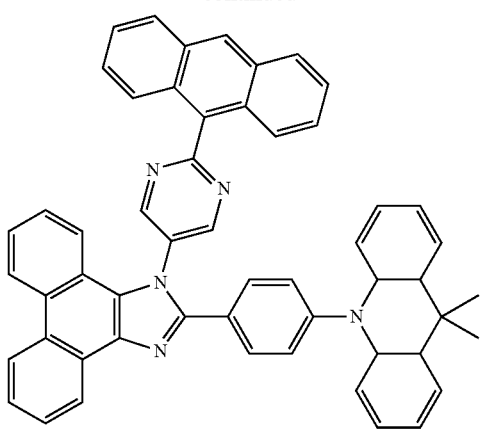
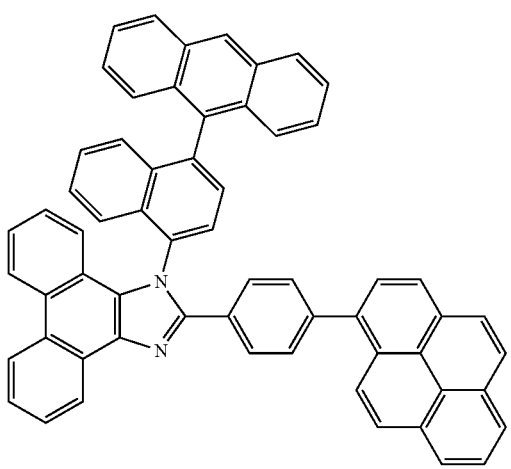
56
-continued
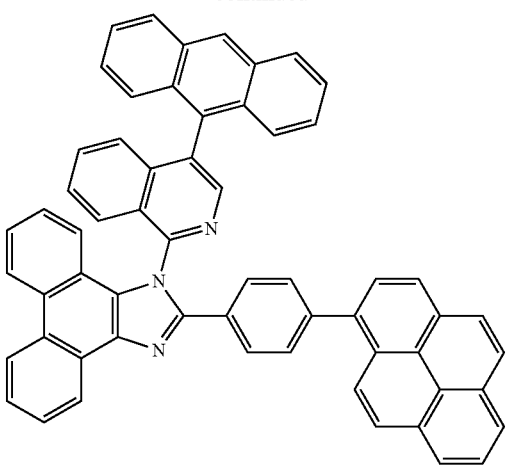
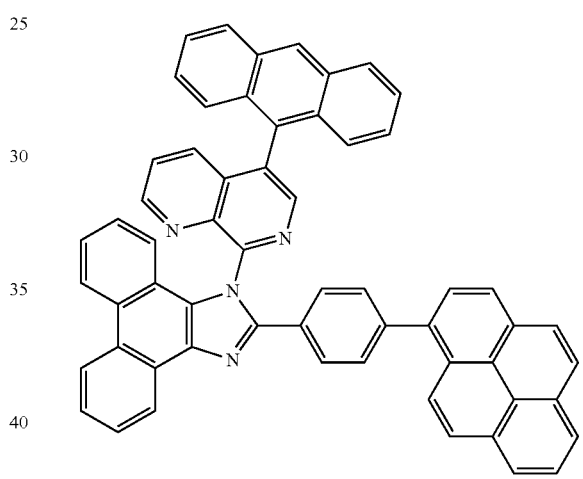
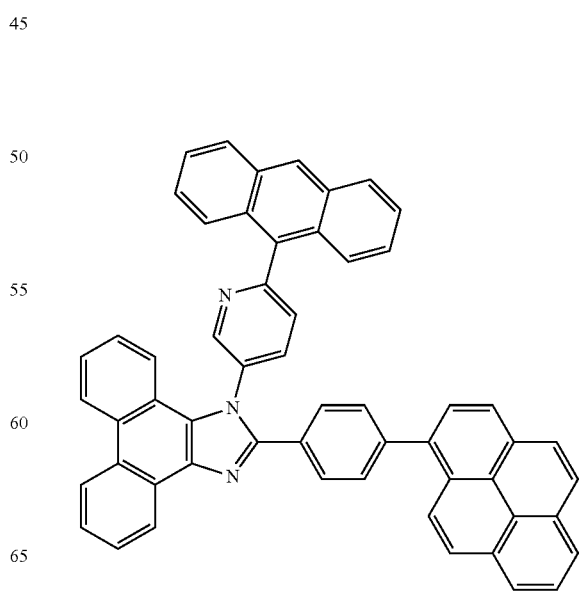

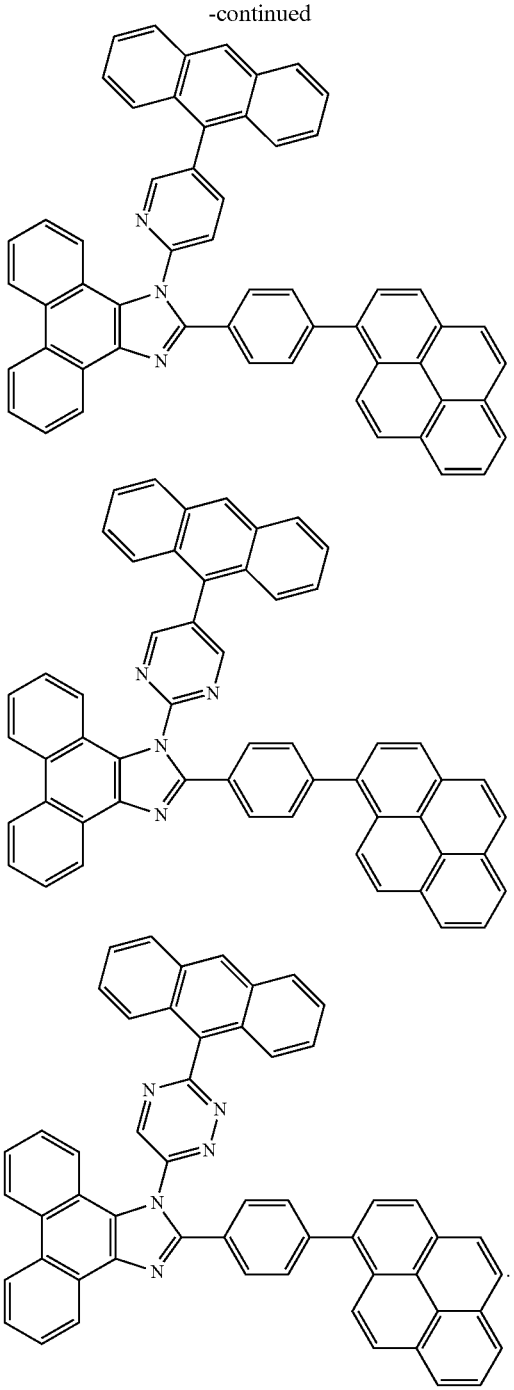

The phenanthroimidazole compound having the above structure has a phenanthroimidazole group and an anthryl group, and therefore the stacking capability between planar functional groups can be increased. Moreover, since a benzene ring is introduced in the phenanthroimidazole compound of the present embodiment, conjugates can be broken off and the energy gap of the phenanthroimidazole compound can be increased, and therefore the phenanthroimidazole compound of the present embodiment is suitable as a host light-emitting material. Moreover, the phenanthroimidazole compound of the present embodiment has electron-withdrawing groups (phenanthroimidazole group and anthryl group) and an electron-releasing group (the group connected to a carbon atom in an imidazole group). Therefore, the phenanthroimidazole compound of the present embodiment has bipolar characteristics to balance electron and hole transfers.

In the following, the organic light-emitting diode of an embodiment of the invention is described with reference to figures.

FIG. 1 is a cross-sectional schematic diagram of an organic light-emitting diode according to an embodiment of the invention.

Referring to FIG. 1, an organic light-emitting diode 10 of the present embodiment includes an anode 102, a cathode 104, and a light-emitting layer 106. The light-emitting layer 106 is disposed between the anode 102 and the cathode 104. The anode 102 can be obtained from a conductor having high work function to facilitate the injection of holes in the light-emitting layer 106. The material of the anode 102 is, for instance, metal, metal oxide, a conducting polymer, or a combination thereof. Specifically, the metal is, for instance, nickel, platinum, vanadium, chromium, copper, zinc, gold, or an alloy thereof; the metal oxide is, for instance, zinc oxide, indium oxide, indium tin oxide (ITO), or indium zinc oxide (IZO); the combination of the metal and the oxide is, for instance, a combination of ZnO and Al or a combination of $SnO_2$ and Sb; the conductive polymer is, for instance, poly(3-methylthiophene), poly(3,4-(ethylene-1,2-dioxy) thiophene (PEDT), polypyrrole, or polyaniline, but the invention is not limited thereto.

The cathode 104 can be obtained from a conductor having low work function to facilitate the injection of electrons in the light-emitting layer 106. The material of the cathode 104 is, for instance, metal or multilayer structure material. Specifically, the metal is, for instance, magnesium, calcium, sodium, potassium, titanium, indium, yttrium, lithium, gadolinium, aluminum, silver, tin, lead, cesium, barium, or an alloy thereof; the material of the multilayer structure is, for instance, LiF/Al, $LiO_2$/Al, LiF/Ca, LiF/Al, or $BaF_2$/Ca, but the invention is not limited thereto.

In the present embodiment, the light-emitting layer 106 includes the phenanthroimidazole compound of the above embodiments. Specifically, the light-emitting layer 106 includes one phenanthroimidazole compound of the above embodiments, at least two phenanthroimidazole compounds of the above embodiments, or a mixture of at least one of the phenanthroimidazole compounds of the above embodiments and other compounds.

The light-emitting layer 106 generally includes a host light-emitting material and a guest light-emitting material. In the present embodiment, the phenanthroimidazole compound of the above embodiments can be used as a host light-emitting material and mixed with a guest light-emitting material. In an embodiment, the light-emitting layer 106 can include a phenanthroimidazole compound and other host light-emitting materials.

The host light-emitting material other than the phenanthroimidazole compound of the above embodiments includes, for instance, a condensation aromatic cycle derivative, a heterocycle-containing compound, or a similar compound thereof. The condensation aromatic cycle derivative is, for instance, an anthracene derivative, a pyrene derivative, a naphthalene derivative, a pentacene derivative, a phenanthrene derivative, a fluoranthene compound, or a similar compound thereof. The heterocycle-containing compound is, for instance, a carbazole derivative, a dibenzofuran derivative, a ladder-type furan compound, a pyrimidine derivative, or a similar compound thereof.

The guest light-emitting material is, for instance, an arylamine derivative, a styrylamine compound, a boron complex, a fluoranthene compound, a metal complex, or a similar compound thereof. Specifically, the arylamine derivative is, for instance, a fused aromatic ring derivative substituted by an arylamine group, and examples thereof include, for instance, pyrene, anthracene, chrysene, and periflanthene having an arylamine group; specific examples of the styrylamine compound include styrylamine, styryldiamine, styryltriamine, and styryltetramine. Examples of the metal complex include an iridium complex and a platinum complex, but are not limited thereto.

In an embodiment, the organic light-emitting diode 10 further includes at least one auxiliary layer, and the auxiliary layer is selected from the group consisting of a hole injection layer, a hole transport layer, a hole blocking layer, an electron injection layer, an electron transport layer, and an electron blocking layer.

Figure 2:
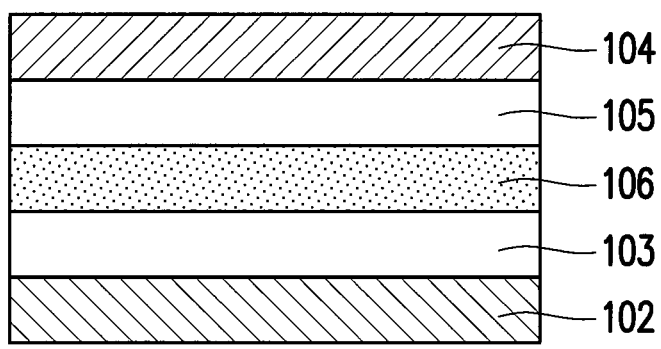
FIG. 2 is a cross-sectional schematic diagram of an organic light-emitting diode according to another embodiment of the invention.

FIG. 2 is a cross-sectional schematic diagram of an organic light-emitting diode according to another embodiment of the invention. In FIG. 2, the same elements as FIG. 1 are represented by the same reference numerals, and descriptions of the same technical content are omitted. An organic light-emitting diode 20 includes an anode 102, a hole transport layer 103, a light-emitting layer 106, an electron transport layer 105, and a cathode 104. In the present embodiment, the light-emitting layer 106 includes the phenanthroimidazole compound of the above embodiments.

In the following, the above embodiments are described in more detail with reference to examples. However, the examples are not to be construed as limiting the scope of the invention in any sense.

Synthesis of Organic Compound

Synthesis Example 1: Synthesis of Compound A

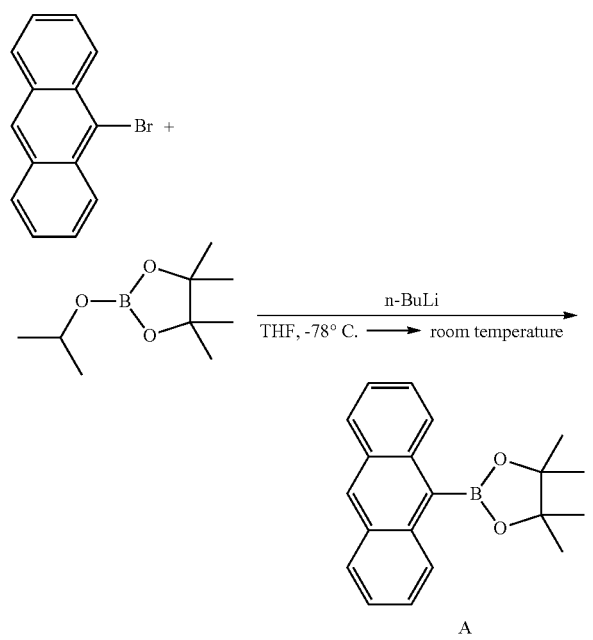

In a double neck bottle, 9-bromoanthracene (5.16 g, 20 mmol) and a stir bar were added, and an adapter was provided and the system was converted to vacuum state. Then, the bottle was baked to remove water vapor and oxygen. The system was converted back to nitrogen, and anhydrous tetrahydrofuran (THF) (200 mL) was added. Then, the reaction was reduced to −78° C. using acetone and liquid nitrogen, and 2.5 M n-butyllithium (9.6 ml, 24 mmol) was slowly added. After reacting for 1 hour at −78° C., 2-isopropoxy-4,4,5,5-tetramethyl-1,3,2-dioxaborolane (4.88 mL, 24 mmol) was added, and the system was returned to room temperature. After reacting overnight, water and dichloromethane were added in an ice bath, and the mixture in the reaction flask was extracted multiple times via dichloromethane to obtain an organic layer. Water was removed using anhydrous magnesium sulfate, and then filtering was performed using celite and the filtrate was drained using a rotary concentrator. Next, purification was performed via column chromatography (eluent: dichloromethane:n-hexane=1:3) to obtain a white compound A (4.62 g, yield: 76%).

Spectral data of compound A: $^1$H NMR (400 MHz, CDCl$_3$): δ 8.46 (s, 1H), 8.42 (d, J=8.0 Hz, 2H), 7.97 (d, J=8.0 Hz, 2H), 7.49-7.40 (m, 4H), 1.56 (s, 12H)

$^{13}$C NMR (100 MHz, CDCl$_3$): δ 135.88, 131.10, 129.47, 128.78, 128.28, 125.77, 124.85, 84.36, 25.15.

Synthesis Example 2: Synthesis of Compound B

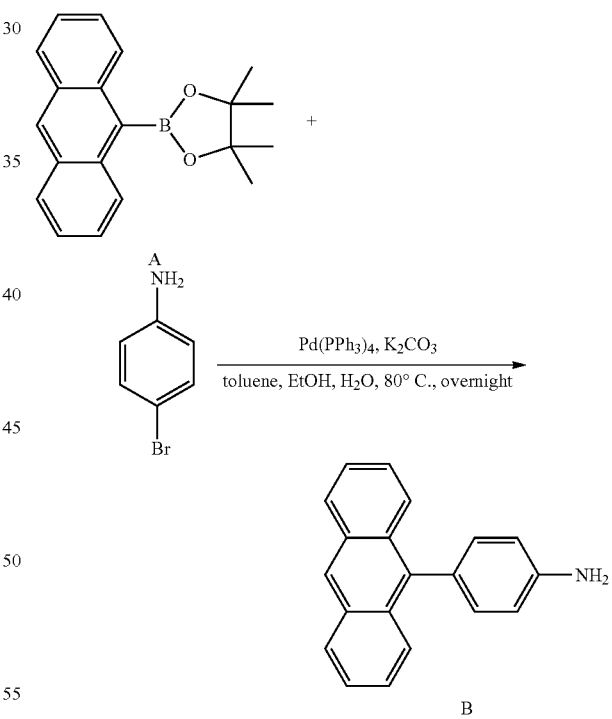

Compound A (1.52 g, 5 mmol), 4-bromoaniline (0.95 g, 5.5 mmol), Pd(PPh$_3$)$_4$ (0.58 g, 0.5 mmol), K$_2$CO$_3$ (2.43 g, 17.6 mmol), and a stir bar were placed in a high-pressure pipe, and the pipe was vacuumed and nitrogen was introduced. Next, toluene (15 mL), ethanol (5 mL), and water (5 mL) were added in a nitrogen atmosphere. After reacting overnight at 80° C., the mixture was cooled to room temperature, and the mixture in the reaction flask was filtered using celite and silica gel and washed with dichloromethane and water and extracted multiple times using dichloromethane to obtain an organic layer. Water was removed using anhydrous magnesium sulfate, and filtering was performed using celite and the filtrate was drained using a rotary concentrator. Next, purification was performed via column chromatography (eluent: dichloromethane:n-hexane=1:1) to obtain a yellow brown compound B (1.04 g, yield: 77%).

Spectral data of compound B: $^1$H NMR (400 MHz, CDCl$_3$): δ 8.44 (s, 1H), 8.01 (d, J=8.4 Hz, 2H), 7.76 (d, J=8.8 Hz, 2H), 7.45-7.41 (m, 2H), 7.35-7.30 (m, 2H), 7.20 (d, J=8.4 Hz, 2H), 6.88 (d, J=8.4 Hz, 2H), 3.82 (s, 2H)

$^{13}$C NMR (100 MHz, CDCl$_3$): δ 145.61, 137.35, 132.07, 131.39, 130.55, 128.42, 128.22, 127.03, 126.04, 125.01, 124.95, 114.89.

Synthesis Example 3: Synthesis of Compound PIACzph

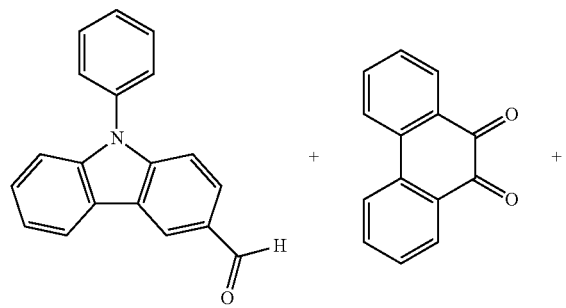

In a round-bottomed flask, compound B (0.65 g, 2.4 mmol), compound F (0.54 g, 2 mmol), phenanthrene-9,10-dione (0.50 g, 2.4 mmol), ammonium acetate (1.54 g, 20 mmol), and a stir bar were added, and then acetic acid was added (80 mL). After reacting two days in nitrogen atmosphere and 140° C., the mixture was cooled to room temperature and added in water to precipitate a crude product. Filtering was performed using a ceramic funnel, and excess acetic acid was washed away with water, and then impurities were washed away with methanol. Lastly, the filter medium was purified via sublimation at a temperature of 350° C. and a pressure of 7×10$^{-6}$ torr to obtain a yellow brown glassy compound PIACzph (0.83 g, yield: 58%).

Spectral data of compound PIACzph: $^1$H NMR (400 MHz, CDCl$_3$): δ 8.97 (d, J=8.0 Hz, 1H), 8.85 (d, J=8.4 Hz, 1H), 8.76 (d, J=8.0 Hz, 1H), 8.54 (s, 1H), 8.46 (s, 1H), 8.09 (d, J=7.6 Hz, 2H), 8.05 (d, J=8.4 Hz, 1H), 7.95 (d, J=8.4 Hz, 1H), 7.85-7.76 (m, 4H), 7.70-7.58 (m, 9H), 7.55-7.39 (m, 9H), 7.31-7.28 (m, 1H), 6.95 (t, J=7.6 Hz, 1H)

$^{13}$C NMR (175 MHz, CDCl$_3$): δ 152.01, 141.36, 140.97, 140.41, 138.59, 137.57, 137.31, 135.10, 133.06, 131.28, 131.26, 129.98, 129.88, 129.57, 129.26, 128.65, 128.46, 128.25, 128.07, 127.99, 127.73, 127.33, 127.30, 127.08, 126.35, 126.23, 126.07, 125.97, 125.90, 125.56, 125.26, 125.20, 124.79, 124.29, 123.31, 123.19, 123.16, 123.14, 122.84, 122.25, 121.60, 120.92, 120.52, 120.40, 110.06, 109.71

HRMS(FAB$^+$): [M$^+$] calcd. for C$_{53}$H$_{34}$N$_3$, 712.2674. found, 712.2753.

Anal. calcd. For C$_{53}$H$_{33}$N$_3$: C, 89.42; H, 4.67; N, 5.90. found: C, 89.37; H, 4.65; N, 5.95.

Synthesis Example 4: Synthesis of Compound PIAAn

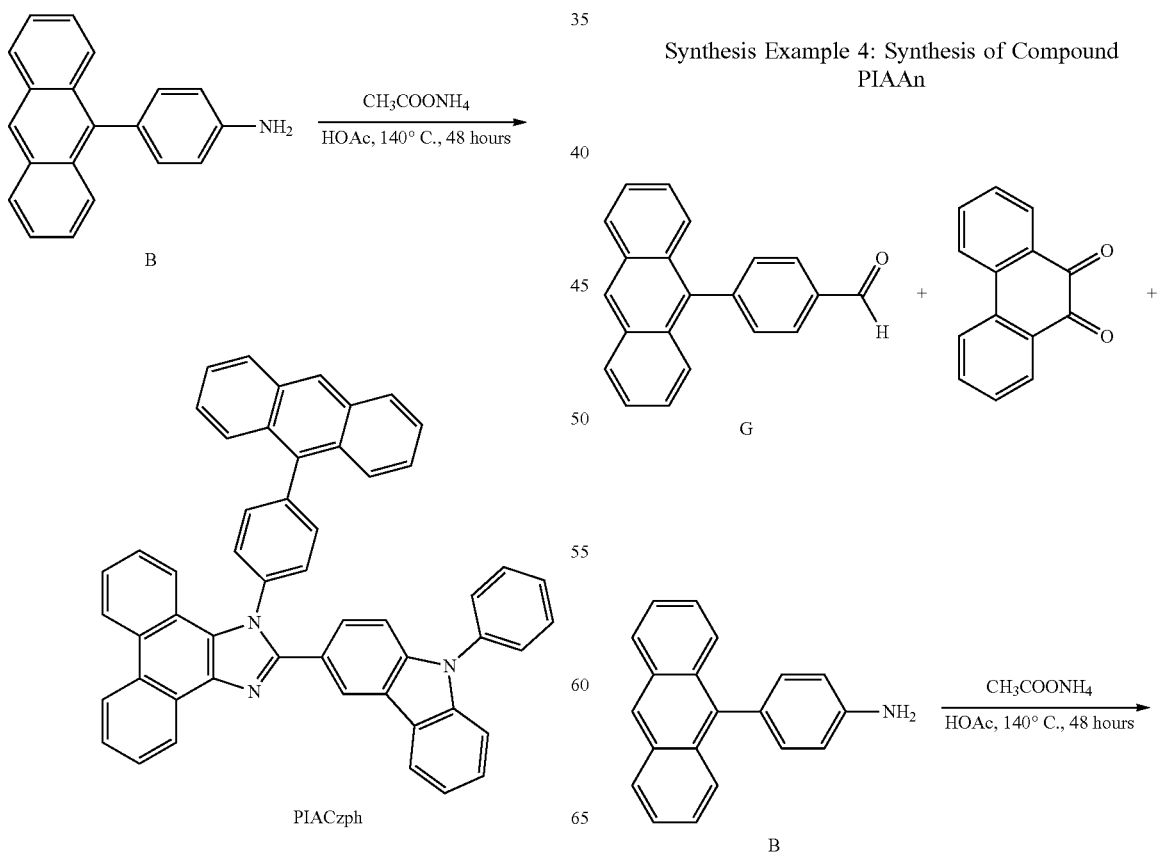

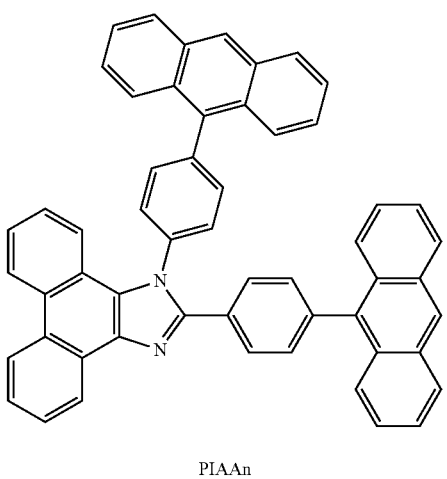

PIAAn

In a round-bottomed flask, compound B (0.65 g, 2.4 mmol), compound G (0.56 g, 2 mmol), phenanthrene-9,10-dione (0.50 g, 2.4 mmol), ammonium acetate (1.54 g, 20 mmol), and a stir bar were added, and then acetic acid was added (80 mL). After reacting two days in nitrogen atmosphere and 140° C., the mixture was cooled to room temperature and added in water to precipitate a crude product. The aqueous layer was extracted using tetrahydrofuran (THF) and dichloromethane and the organic layer was drained using a rotary concentrator. Next, filtering was performed using a ceramic funnel, and excess acetic acid was washed away with water, and then most impurities were washed away with methanol. Lastly, the filter medium was purified via sublimation at a temperature of 380° C. and a pressure of $7\times10^{-6}$ torr to obtain a yellow glassy compound PIAAn (0.87 g, yield: 60%).

Spectral data of compound PIAAn: $^1$H NMR (400 MHz, $d_8$-THF): δ 8.95-8.92 (m, 2H), 8.85 (d, J=8.0 Hz, 1H), 8.63 (s, 1H), 8.59 (s, 1H), 8.16-8.04 (m, 8H), 7.95 (d, J=8.0 Hz, 1H), 7.81 (d, J=8.0 Hz, 2H), 7.78-7.66 (m, 6H), 7.63-7.48 (m, 6H), 7.45 (t, J=7.4 Hz, 2H), 7.35-7.30 (m, 3H), 7.13 (t, J=7.8 Hz, 1H)

$^{13}$C NMR (175 MHz, $d_8$-THF): δ 150.25, 140.71, 139.43, 138.82, 137.76, 136.05, 135.17, 133.19, 131.52, 131.48, 130.92, 130.47, 130.06, 130.01, 129.89, 129.69, 129.38, 129.16, 128.46, 128.36, 128.27, 128.23, 127.69, 127.08, 126.90, 126.68, 126.25, 126.05, 125.88, 125.77, 125.67, 125.41, 125.28, 125.01, 124.90, 124.70, 124.17, 123.26, 123.06, 122.54, 120.83

HRMS(FAB$^+$): [M$^+$] calcd. for $C_{55}H_{35}N_2$, 723.2722. found, 723.2800.

Anal. calcd. For $C_{55}H_{34}N_2$: C, 91.38; H, 4.74; N, 3.88. found: C, 91.25; H, 4.47; N, 4.14.

Synthesis Example 5: Synthesis of Compound PIACz

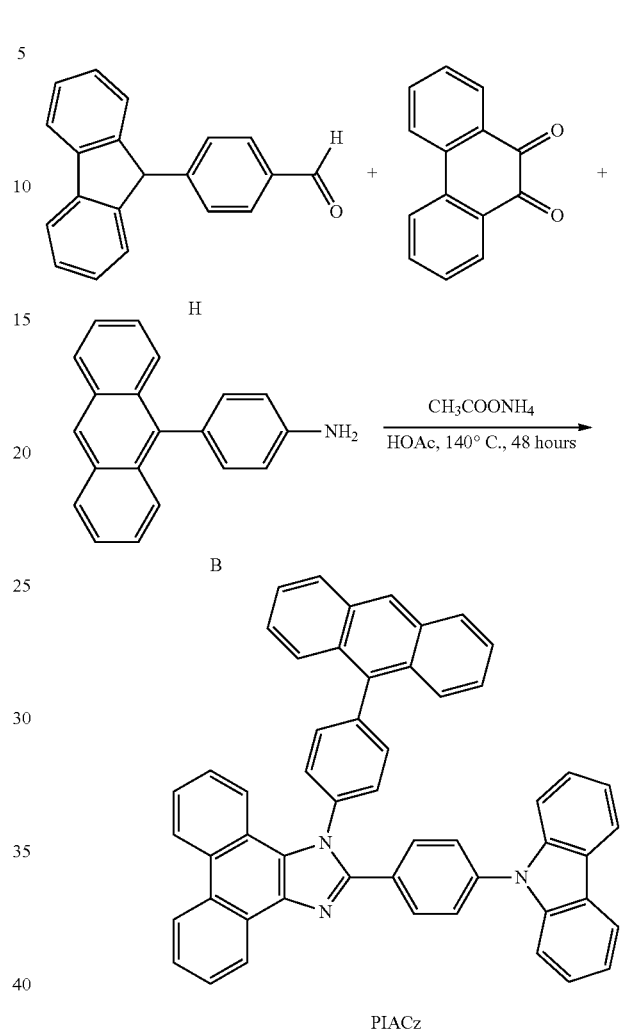

PIACz

In a round-bottomed flask, compound B (0.65 g, 2.4 mmol), compound H (0.54 g, 2 mmol), phenanthrene-9,10-dione (0.50 g, 2.4 mmol), ammonium acetate (1.54 g, 20 mmol), and a stir bar were added, and then acetic acid was added (80 mL). After reacting two days in nitrogen atmosphere and 140° C., the mixture was cooled to room temperature and added in water to precipitate a crude product. Next, filtering was performed using a ceramic funnel, and excess acetic acid was washed away with water, and then most impurities were washed away with methanol. Lastly, the filter medium was purified via sublimation at a temperature of 380° C. and a pressure of $7\times10^{-6}$ torr to obtain a brown glassy compound PIACz (0.93 g, yield: 65%).

Spectral data of compound PIACz: $^1$H NMR (400 MHz, $d_8$-THF): δ 8.95-8.90 (m, 2H), 8.85 (d, J=8.0 Hz, 1H), 8.66 (s, 1H), 8.19-8.11 (m, 6H), 8.03 (d, J=8.0 Hz, 2H), 7.94 (d, J=7.6 Hz, 1H), 7.82-7.74 (m, 6H), 7.71-7.36 (m, 12H), 7.27 (t, J=7.4 Hz, 2H)

$^{13}$C NMR (175 MHz, $d_8$-THF): δ 150.85, 141.89, 141.60, 139.76, 139.23, 138.86, 136.25, 134.34, 132.62, 131.81, 131.11, 131.02, 130.79, 130.51, 129.59, 129.52, 129.47, 128.71, 128.26, 128.02, 127.31, 127.18, 127.01, 126.98, 126.91, 126.80, 126.44, 126.15, 126.12, 125.89, 125.29, 124.74, 124.29, 124.19, 123.62, 121.92, 121.10, 110.66, 110.48

HRMS(FAB⁺): [M⁺] calcd. for C₅₃H₃₄N₃, 712.2674. found, 712.2753.

Anal. calcd. For C₅₃H₃₃N₃: C, 89.42; H, 4.67; N, 5.90. found: C, 89.23; H, 4.73; N, 5.95.

Synthesis Example 6: Synthesis of Compound PIADPA

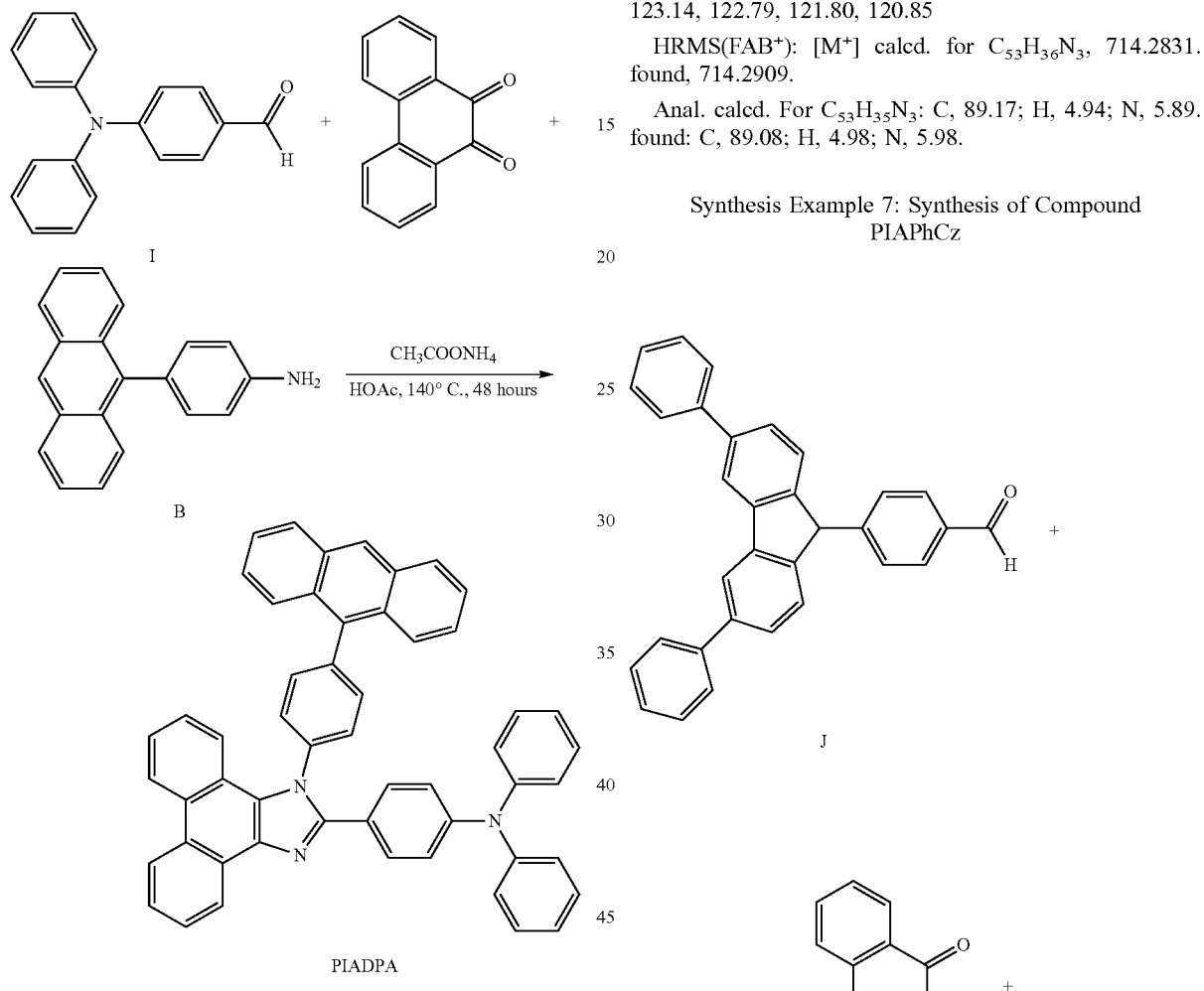

PIADPA

In a round-bottomed flask, compound B (0.65 g, 2.4 mmol), compound I (0.55 g, 2 mmol), phenanthrene-9,10-dione (0.50 g, 2.4 mmol), ammonium acetate (1.54 g, 20 mmol), and a stir bar were added, and then acetic acid was added (80 mL). After reacting two days in nitrogen atmosphere and 140° C., the mixture was cooled to room temperature and added in water to precipitate a crude product. The aqueous layer was extracted using tetrahydrofuran (THF) and dichloromethane and the organic layer was drained using a rotary concentrator. Next, filtering was performed using a ceramic funnel, and excess acetic acid was washed away with water, and then most impurities were washed away with methanol. Lastly, the filter medium was purified via sublimation at a temperature of 370° C. and a pressure of 7×10⁻⁶ torr to obtain a dark brown glassy compound PIADPA (1.00 g, yield: 70%).

Spectral data of compound PIADPA: ¹H NMR (400 MHz, CDCl₃): δ 8.90 (d, J=7.6 Hz, 1H), 8.82 (d, J=8.0 Hz, 1H), 8.74 (d, J=8.4 Hz, 1H), 8.56 (s, 1H), 8.12-8.07 (m, 2H), 7.86-7.84 (m, 1H), 7.77-7.73 (m, 3H), 7.68-7.65 (m, 3H), 7.61-7.50 (m, 8H), 7.47-7.43 (m, 2H), 7.29-7.25 (m, 4H), 7.15-7.12 (m, 4H), 7.09-7.05 (m, 4H)

¹³C NMR (175 MHz, CDCl₃): δ 151.14, 148.58, 147.21, 140.47, 138.39, 137.52, 135.09, 133.06, 131.32, 130.31, 130.03, 129.87, 129.44, 129.26, 128.67, 128.54, 128.25, 128.02, 127.32, 127.25, 126.24, 126.10, 125.99, 125.87, 125.57, 125.30, 125.23, 125.14, 124.82, 124.27, 123.60, 123.14, 122.79, 121.80, 120.85

HRMS(FAB⁺): [M⁺] calcd. for C₅₃H₃₆N₃, 714.2831. found, 714.2909.

Anal. calcd. For C₅₃H₃₅N₃: C, 89.17; H, 4.94; N, 5.89. found: C, 89.08; H, 4.98; N, 5.98.

Synthesis Example 7: Synthesis of Compound PIAPhCz

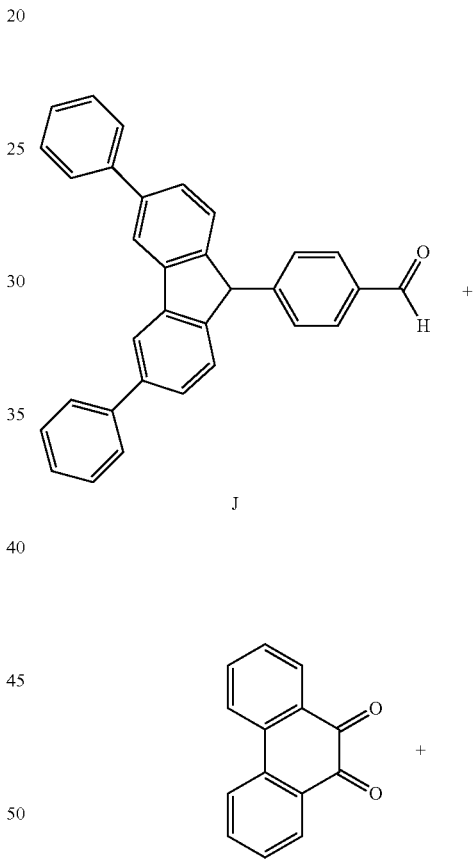

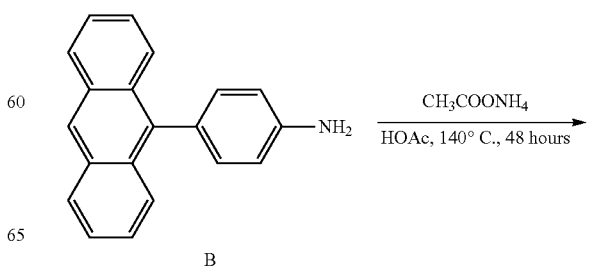

67
-continued

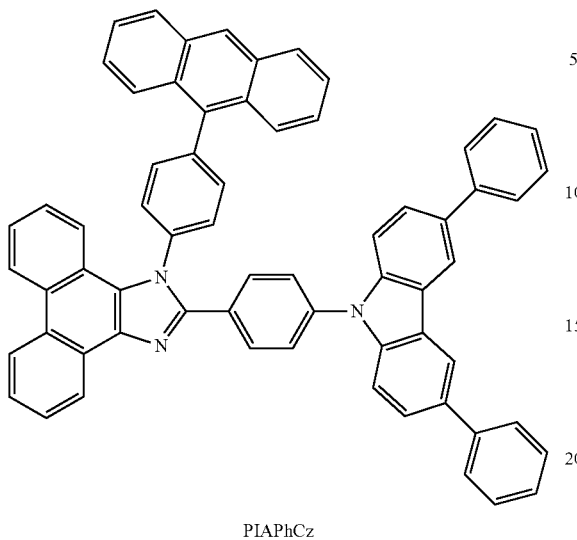

PIAPhCz

In a round-bottomed flask, compound B (0.65 g, 2.4 mmol), compound J (0.85 g, 2 mmol), phenanthrene-9,10-dione (0.50 g, 2.4 mmol), ammonium acetate (1.54 g, 20 mmol), and a stir bar were added, and then acetic acid was added (80 mL). After reacting two days in nitrogen atmosphere and 140° C., the mixture was cooled to room temperature and added in water to precipitate a crude product. Next, filtering was performed using a ceramic funnel, and excess acetic acid was washed away with water, and then most impurities were washed away with methanol. Lastly, the filter medium was purified via sublimation at a temperature of 415° C. and a pressure of $7 \times 10^{-6}$ torr to obtain a yellow glassy compound PIAPhCz (0.69 g, yield: 40%).

Spectral data of compound PIAPhCz: $^1$H NMR (400 MHz, $d_8$-THF): δ 8.95-8.91 (m, 2H), 8.85 (d, J=8.0 Hz, 1H), 8.66 (s, 1H), 8.58 (s, 1H), 8.20 (d, J=8.4 Hz, 2H), 8.17-8.07 (m, 4H), 8.04 (d, J=8.0 Hz, 2H), 7.95 (d, J=8.4 Hz, 1H), 7.83-7.66 (m, 12H), 7.63-7.29 (m, 15H)

$^{13}$C NMR (175 MHz, $d_8$-THF): δ 151.55, 150.81, 142.76, 142.65, 141.91, 141.56, 141.53, 140.54, 140.16, 139.76, 139.15, 138.87, 137.08, 136.24, 135.08, 134.89, 134.36, 132.62, 132.60, 132.35, 132.08, 131.87, 131.42, 131.17, 131.12, 131.02, 130.79, 130.52, 130.46, 130.29, 129.59, 129.54, 129.51, 129.48, 129.37, 129.35, 128.73, 128.71, 128.27, 128.03, 127.94, 127.91, 127.80, 127.46, 127.41, 127.32, 127.27, 127.18, 127.09, 126.98, 126.92, 126.80, 126.63, 126.52, 126.46, 126.43, 126.15, 126.13, 125.98, 125.91, 125:87, 125.62, 125.54, 125.30, 124.28, 124.25, 124.20, 124.17, 123.62, 121.92, 121.88, 119.77, 119.70, 111.14, 110.96

HRMS(FAB$^+$): [M$^+$] calcd. for $C_{65}H_{42}N_3$, 864.3300. found, 864.3379.

Anal. calcd. For $C_{65}H_{41}N_3$: C, 90.35; H, 4.78; N, 4.86. found: C, 90.21; H, 4.66; N, 4.90.

68
Synthesis Example 8: Synthesis of Compound PIAtBCz

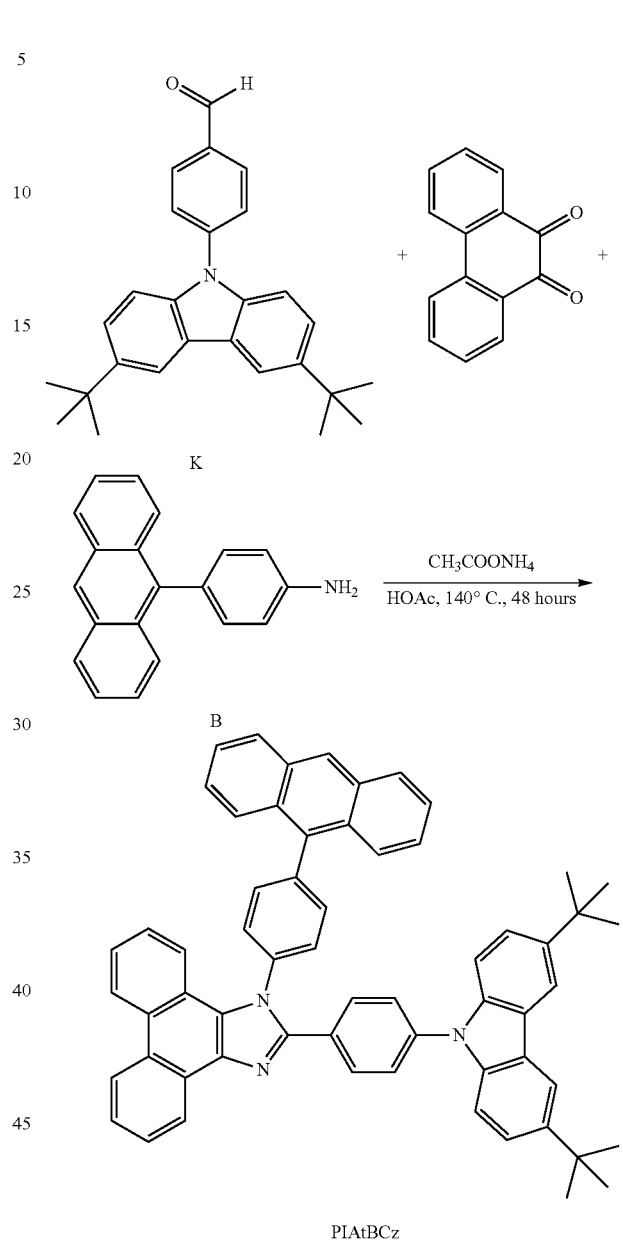

In a round-bottomed flask, compound B (0.65 g, 2.4 mmol), compound K (0.77 g, 2 mmol), phenanthrene-9,10-dione (0.50 g, 2.4 mmol), ammonium acetate (1.54 g, 20 mmol), and a stir bar were added, and then acetic acid was added (80 mL). After reacting two days in nitrogen atmosphere and 140° C., the mixture was cooled to room temperature and added in water to precipitate a crude product. Next, filtering was performed using a ceramic funnel, and excess acetic acid was washed away with water, and then most impurities were washed away with methanol. Lastly, the filter medium was purified via sublimation at a temperature of 370° C. and a pressure of $7 \times 10^{-6}$ torr to obtain a yellow brown glassy compound PIAtBCz (1.40 g, yield: 85%).

Spectral data of compound PIAtBCz: $^1$H NMR (400 MHz, CDCl$_3$): δ 8.94 (d, J=8.0 Hz, 1H), 8.86 (d, J=8.4 Hz, 1H), 8.77 (d, J=8.4 Hz, 1H), 8.59 (s, 1H), 8.13-8.08 (m, 4H), 7.98 (d, J=8.4 Hz, 2H), 7.87-7.60 (m, 12H), 7.57-7.53 (m, 2H), 7.51-7.34 (m, 7H), 1.46 (s, 18H)

$^{13}$C NMR (175 MHz, CDCl$_3$): δ 150.46, 143.22, 140.75, 138.87, 138.12, 137.67, 134.97, 133.24, 131.36, 131.00, 130.05, 129.92, 129.52, 129.44, 128.96, 128.72, 128.39, 128.33, 127.46, 127.25, 126.38, 126.35, 126.19, 126.06, 125.81, 125.68, 125.32, 125.22, 125.16, 124.36, 123.85, 123.58, 123.22, 123.09, 122.80, 120.98, 116.28, 109.23, 34.75, 31.99, 30.92

HRMS(FAB$^+$): [M$^+$] calcd. for C$_{61}$H$_{50}$N$_3$, 824.3926. found, 824.4005.

[Property Evaluation of Compounds]

[Optical Properties]

The optical properties of the phenanthroimidazole compounds of the examples above are provided in Table 1 and Table 2.

TABLE 1

| Compound | Absorption spectrum in solvent (nm)$^a$ | Fluorescence spectrum in solvent (nm)$^b$ | Absorption spectrum in thin film (nm) | Fluorescence spectrum in thin film (nm) | Phosphorescence in solvent (nm)$^c$ | FWHM (nm)$^d$ in solvent |
|---|---|---|---|---|---|---|
| PIAAn | 282, 232, 348, 366, 386 | 429 | 280, 352, 372, 392 | 448 | 693, 766 | 55 |
| PIACzph | 308, 330, 348, 366, 386 | 403, 422 | 310, 346, 372, 392 | 443 | 475, 502 | 49 |
| PIACz | 292, 346, 366, 386 | 403, 421 | 280, 350, 372, 390 | 438 | 510 | 53 |
| PIAPhCz | 294, 348, 366, 386 | 406, 423 | 300, 350, 372, 394 | 448 | 511 | 55 |
| PIADPA | 286, 350, 366, 384 | 406, 424 | 286, 356, 370, 386 | 465 | 521, 547 | 61 |
| PIAtBCz | 298, 348, 366, 386 | 404, 421 | 298, 338, 352, 368 | 439 | 493, 514 | 50 |

$^a$measured in 1 × 10$^{-5}$M toluene solution;
$^b$measured in 1 × 10$^{-5}$M toluene solution;
$^c$PIAAn, PIACzph, PIADPA, and PIAtBCz measured at 77K in 1 × 10$^{-5}$M toluene solution, PIACz and PIAPhCz measured at 77K in 1 × 10$^{-5}$M dichloromethane;
$^d$measured in 1 × 10$^{-5}$M toluene solution.

a: measured in 1×10$^{-5}$ M toluene solution;

b: measured in 1×10$^{-5}$ M toluene solution;

c: PIAAn, PIACzph, PIADPA, and PIAtBCz measured at 77 K in 1×10$^{-5}$ M toluene solution, PIACz and PIAPhCz measured at 77 K in 1×10$^{-5}$ M dichloromethane;

d: measured in 1×10$^{-5}$ M toluene solution.

It can be known from the results of Table 1 that, the fluorescent emission wavelength of the phenanthroimidazole compounds of the above embodiments is distributed between 403 nm and 465 nm. In other words, the phenanthroimidazole compounds of the above embodiments can emit blue light, and are therefore suitable as blue host materials, and can also be used as blue light-emitting materials.

TABLE 2

|  | PIAAn | PIACzph | PIACz | PIAPhCz | PIADPA |
|---|---|---|---|---|---|
| Quantum efficiency (%)$^e$ | 60 | 48 | 64 | 69 | 43 |
| Quantum efficiency (%)$^f$ | 98 | 94 | 88 | 83 | 76 |

$^e$fluorescence quantum efficiency measured in 50 nm thin film, excitation wavelength: 340 nm;
$^f$fluorescence quantum efficiency measured in thin film (50 nm, phenanthroimidazole compound as host material) doped with 5% of compound BCzVBi, excitation wavelength: 340 nm.

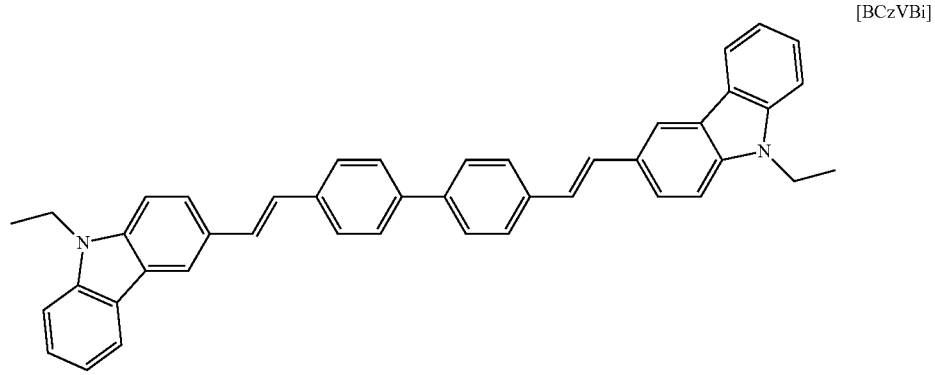 [SMILES: CCn1c2ccccc2c2cc(/C=C/c3ccc(-c4ccc(/C=C/c5ccc6c(c5)c5ccccc5n6CC)cc4)cc3)ccc21]

[BCzVBi]

It can be known from the results of Table 2 that, the phenanthroimidazole compounds of the above examples have high quantum efficiency.

[Thermal Stability Properties]

In the thermal stability test, thermal stability property testing was performed using a thermogravimetric differential thermal analyzer at a heating rate of 10° C./minute.

Table 3 is the result of a thermal stability test of compounds PIACz, PIAtBCz, PIADPA, PIACzph, PIAA, and PIAPhCz.

TABLE 3

| Compound | $T_g$ (° C.) | $T_c$ (° C.) | $T_m$ (° C.) | $T_d$ (° C.) |
|---|---|---|---|---|
| PIACz | 161 | 219 | 335 | 494 |
| PIAtBCz | 193 | 262 | 332 | 506 |
| PIADPA | 140 | 211 | 301 | 462 |
| PIACzph | 164 | N.D. | 331 | 468 |
| PIAAn | N.D. | N.D. | 380 | 466 |
| PIAPhCz | 193 | 279 | 374 | 497 |

$T_g$: glass transition temperature; $T_c$: crystallization temperature; $T_m$: melting temperature; $T_d$: thermal decomposition temperature; N.D.: not detected.

It can be known from the results of Table 3 that, the thermal decomposition temperatures of the phenanthroimidazole compounds of the invention are all higher than 450° C., and the phenanthroimidazole compounds of the invention all have excellent thermal stability.

[Energy Level]

HOMO, LUMO, and energy gap of compounds PIACz, PIAtBCz, PIADPA, PIACzph, PIAAn, and PIAPhCz are provided in Table 4.

TABLE 4

| Compound | PIACz | PIAtBCz | PIADPA | PIACzph | PIAAn | PIAPhCz |
|---|---|---|---|---|---|---|
| HOMO (eV) | 5.82 | 5.72 | 5.47 | 5.42 | 5.82 | 5.65 |
| LUMO (eV) | 2.71 | 2.60 | 2.40 | 2.32 | 2.75 | 2.55 |
| Eg (eV) | 3.11 | 3.12 | 3.07 | 3.10 | 3.07 | 3.10 |

[Dipole Orientation]

Experimental Example 1

Compound PIADPA obtained in synthesis example 6 was used as the host light-emitting material, and 5% of compound BCzVBi was used as the guest light-emitting material (i.e., dopant) to form a thin film.

Experimental Example 2

A thin film was formed using a similar method to experimental example 1, and the difference thereof is only that compound PIAPhCz obtained in synthesis example 7 was used as the host light-emitting material of the light-emitting layer.

Experimental Example 3

A thin film was formed using a similar method to experimental example 1, and the difference thereof is only that compound PIACz obtained in synthesis example 5 was used as the host light-emitting material of the light-emitting layer.

Experimental Example 4

A thin film was formed using a similar method to experimental example 1, and the difference thereof is only that compound PIACzph obtained in synthesis example 3 was used as the host light-emitting material of the light-emitting layer.

Experimental Example 5

A thin film was formed using a similar method to experimental example 1, and the difference thereof is only that compound PIAAn obtained in synthesis example 4 was used as the host light-emitting material of the light-emitting layer.

In the present example, the thin film formed by TcTa:Ir(ppy)$_3$ was used as a standard product, indicating that the guest material is randomly arranged. The variable angle photoluminescence intensity of the thin films of example 1 to example 5 and the standard product was measured, and the horizontal dipole moment ratio was calculated via the Origin86 program.

Figure 3:
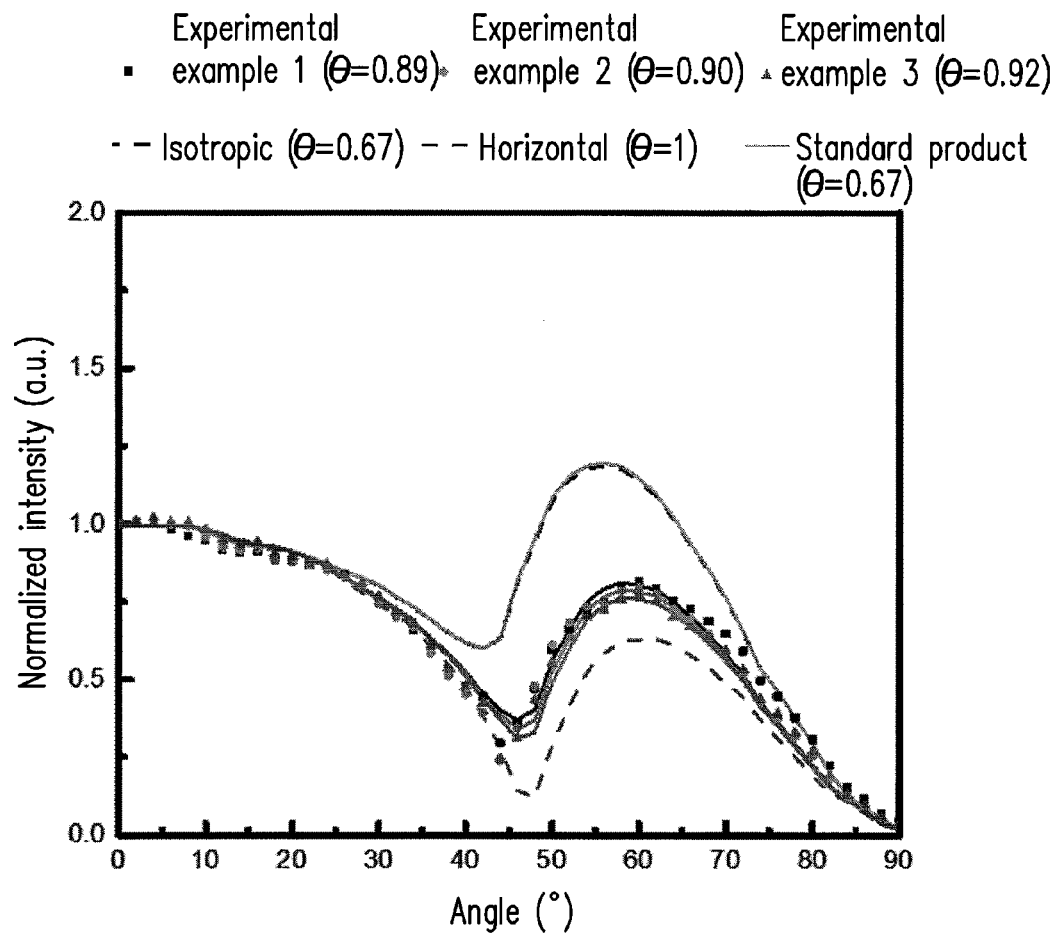
FIG. 3 is the result of variable angle photoluminescence intensity of the thin films of experimental example 1 to experimental example 3 and a standard product.
Figure 4:
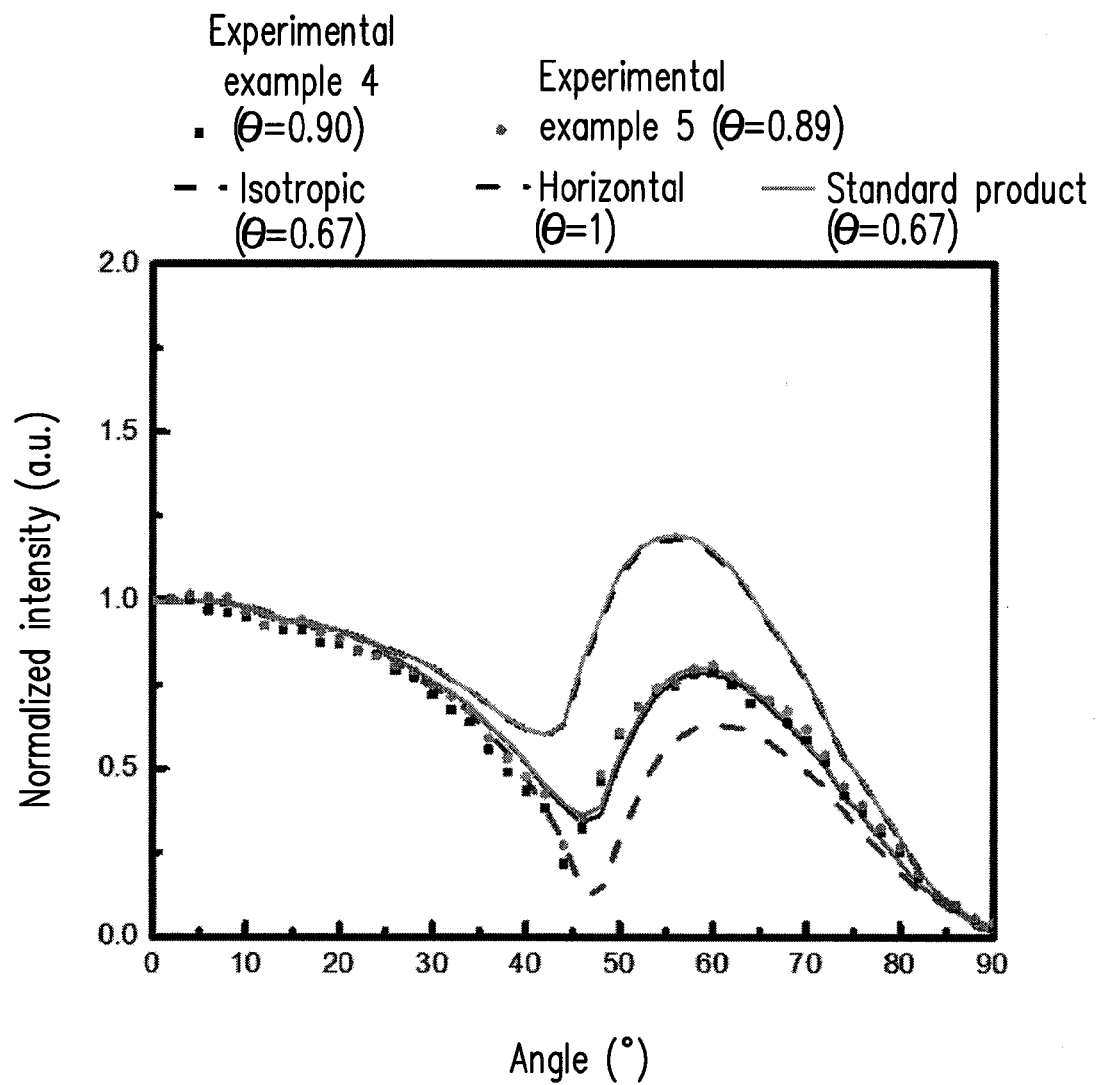
FIG. 4 is the result of variable angle photoluminescence intensity of the thin films of experimental example 4, experimental example 5, and a standard product.

FIG. 3 is the result of variable angle photoluminescence intensity of the thin films of experimental example 1 to experimental example 3 and a standard product. FIG. 4 is the result of variable angle photoluminescence intensity of the thin films of experimental example 4, experimental example 5, and a standard product.

It can be known from the results of FIG. 3 and FIG. 4 that, when the guest material is randomly arranged, the luminous dipole moment is isotropic, and the horizontal transition dipole ratio thereof is θ=0.67. When the arrangement of the guest material is roughly horizontal, the horizontal transition dipole ratio is increased. If the luminous dipole moment is completely horizontal, then the horizontal transition dipole ratio thereof is θ=1. The horizontal transition dipole ratio of the standard product is θ=0.67. The horizontal transition dipole ratio θ of the thin films of experimental example 1 to experimental example 5 is between 0.89 and 0.92. It can be known from the results that, the structural characteristics of the phenanthroimidazole compound of the invention used as the host material make the arrangement of the guest material preferred horizontal, and therefore the horizontal transition dipole ratio of the thin film can be increased to increase the light outcoupling efficiency of the resulting device.

[Manufacture of Organic Light-Emitting Diode]

Experimental Example 6

Compound PIADPA obtained in synthesis example 6 was used as the host light-emitting material, and compound BCzVBi was used as the guest light-emitting material (i.e., dopant) to form an organic light-emitting diode.

Specifically, the manufacturing process of the organic light-emitting diode is as shown below: first, N,N'-di(naphthalen-1-yl)-N,N'-diphenylbiphenyl-4,4'-diamine (NPB) (30 nm) and 4,4',4''-tri(N-carbazolyl)triphenylamine (TCTA) (20 nm) were deposited on an ITO glass substrate used as the anode in order to form a hole transport layer. Then, the host light-emitting material PIADPA (30 nm) doped with 5% of the compound BCzVBi was deposited on the hole transport layer to form a light-emitting layer. Then, 1,3,5-tris[(3-pyridyl)-3-phenyl]benzene (TmPyPb) (30 nm) was deposited on the light-emitting layer to form an electron transport layer. Then, LiF (electron injection layer) (1 nm) and Al were deposited on the electron transport layer to form a cathode. At this point, the manufacture of the organic light-emitting diode of the present experimental example was complete. The organic light-emitting diode has the following structure: ITO/NPB (30 nm)/TCTA (20 nm)/PIADPA: 5% BCzVBi (30 nm)/TmPyPb (30 nm)/LiF (1 nm)/Al.

Experimental Example 7

An organic light-emitting diode was formed using a similar method to experimental example 6, and the difference thereof is only that compound PIAPhCz obtained in synthesis example 7 was used as the host light-emitting material of the light-emitting layer.

Experimental Example 8

An organic light-emitting diode was formed using a similar method to experimental example 6, and the difference thereof is only that compound PIACz obtained in synthesis example 5 was used as the host light-emitting material of the light-emitting layer.

Experimental Example 9

An organic light-emitting diode was formed using a similar method to experimental example 6, and the difference thereof is only that compound PIACzph obtained in synthesis example 3 was used as the host light-emitting material of the light-emitting layer.

Experimental Example 10

An organic light-emitting diode was formed using a similar method to experimental example 6, and the difference thereof is only that compound PIAtBCz obtained in synthesis example 8 was used as the host light-emitting material of the light-emitting layer.

Experimental Example 11

An organic light-emitting diode was formed using a similar method to experimental example 6, and the difference thereof is only that compound PIAAn obtained in synthesis example 4 was used as the host light-emitting material of the light-emitting layer.

Experimental Example 12

The organic light-emitting diode was formed using a similar method to experimental example 11, and the difference thereof is only in that compound BCzVBi was not doped.

Table 5 is the result of the efficacy of the organic light-emitting diodes of experimental example 6 to experimental example 11.

TABLE 5

| | Host light-emitting material | $V_d$ (V) | E.Q.E. (%, V) | $L_{max}$ (cd/$m^2$, V) | C.E. (cd/A, V) | P.E. (lm/W, V) | Maximum radiation wavelength CIE (x, y) (nm) |
|---|---|---|---|---|---|---|---|
| Experimental example 6 | PIADPA | 2.5 | 5.7, 7.0 | 41107, 19.0 | 7.9, 6.5 | 5.1, 4.0 | (0.14, 0.16) 452 |
| Experimental example 7 | PIAPhCz | 2.6 | 6.8, 6.5 | 34716, 19.5 | 8.6, 6.0 | 5.8, 4.0 | (0.14, 0.14) 450 |
| Experimental example 8 | PIACz | 2.6 | 7.1, 6.5 | 42984, 19.0 | 9.4, 6.5 | 6.4, 3.5 | (0.14, 0.15) 452 |
| Experimental example 9 | PIACzph | 2.5 | 7.7, 5.5 | 49455, 19.0 | 9.7, 5.5 | 7.5, 3.5 | (0.14, 0.14) 452 |
| Experimental example 10 | PIAtBCz | 2.9 | 6.1, 6.0 | 29022, 18.0 | 7.3, 6.0 | 4.7, 4.0 | (0.15, 0.13) 450 |
| Experimental example 11 | PIAAn | 2.5 | 10.1, 8.0 | 61204, 20.0 | 12.9, 8.0 | 10.9, 3.0 | (0.15, 0.14) 450 |

$V_d$: driving voltage; E.Q.E.: external quantum efficiency; $L_{max}$: maximum brightness; C.E.: current efficiency; P.E.: power efficiency; CIE: chromaticity coordinates.

It can be known from the results of Table 5 that, the maximum radiation wavelength of the organic light-emitting diodes of experimental example 6 to experimental example 11 is located in the range of 450 nm to 452 nm, and therefore the organic light-emitting diodes of experimental example 6 to experimental example 11 have the characteristics of blue light emission. Moreover, the light-emitting layer of the organic light-emitting diodes of experimental example 6 to experimental example 11 has the phenanthroimidazole compound of the invention and a guest light-emitting material, wherein the structural characteristics of the phenanthroimidazole compound of the invention make the arrangement of the guest light-emitting material preferred horizontal, such that the luminous efficiency of the organic light-emitting diode can be increased. As a result, the organic light-emitting diodes of experimental example 6 to experimental example 11 have low driving voltage and high external quantum efficiency.

Figure 5:
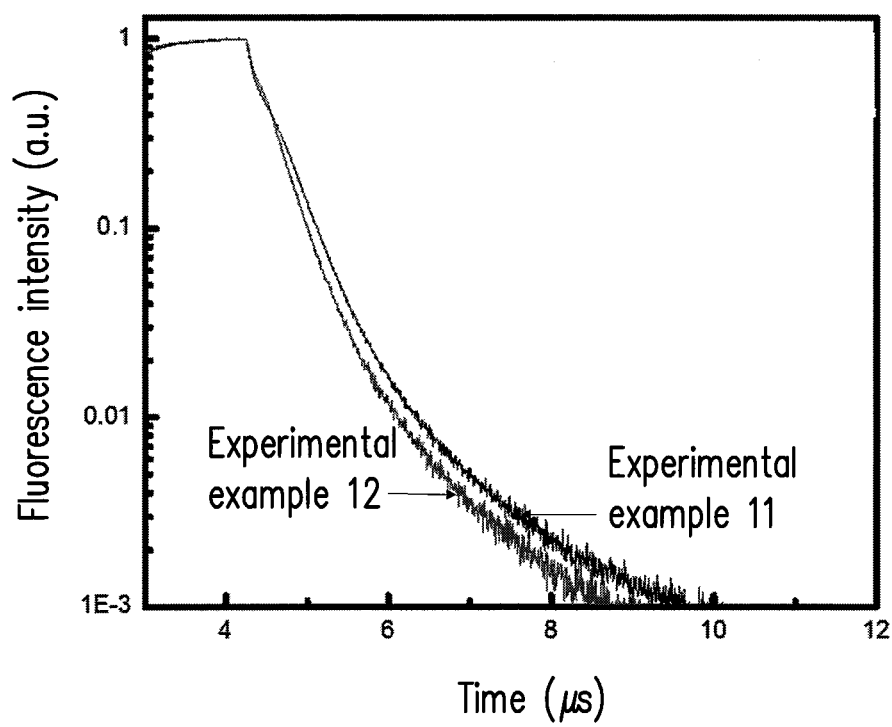
FIG. 5 shows transient electrical excitation fluorescence curves of the organic light-emitting diodes of experimental example 11 and experimental example 12.

FIG. 5 shows transient electrical excitation fluorescence curves of the organic light-emitting diodes of experimental example 11 and experimental example 12.

It can be known from the results of FIG. 5 that, the organic light-emitting diodes of example 11 and example 12 both have the phenomenon of triplet-triplet annihilation (TTA) delayed fluorescence. This is because the good stacking between the planar functional groups of the phenanthroimidazole compound of the invention facilitates the operation of the TTA mechanism, and therefore the luminous efficiency of the organic light-emitting diode can be effectively increased. Moreover, in comparison to the organic light-emitting diode containing only a host light-emitting material of experimental example 12, the phenomenon of delayed fluorescence of the organic light-emitting diode containing a host light-emitting material and a guest light-emitting material (i.e., compound BCzVBi) of experimental example 11 is more significant. This is because the phenanthroimidazole compound of experimental example 11 used as the host material has good energy transfer with the guest material, and therefore fluorescence quantum efficiency can be increased.

Based on the above, the phenanthroimidazole compound of the present embodiment has the characteristics of blue light emission, high quantum efficiency, and good thermal stability. Moreover, the light-emitting layer of the organic light-emitting diode of the present embodiment includes a phenanthroimidazole compound, and therefore has high external quantum efficiency and low driving voltage.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A phenanthroimidazole compound represented by the following chemical formula 1:

[Chemical formula 1]

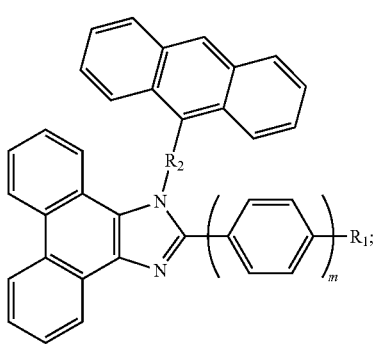

in chemical formula 1,
m is an integer of 0 or 1;
when m is 0, $R_1$ is a substituted or unsubstituted carbazolyl group;
when m is 1, $R_1$ is a substituted or unsubstituted carbazolyl group, a substituted or unsubstituted amine group, a substituted or unsubstituted anthryl group, a substituted or unsubstituted pyrenyl group, or a substituted or unsubstituted

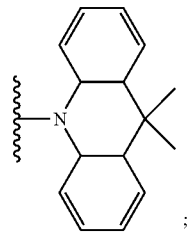 [SMILES: *N1C2C=CC=CC2C(C)(C)C2C=CC=CC21]

and
$R_2$ is a substituted or unsubstituted arylene group or a substituted or unsubstituted nitrogen-containing heteroarylene group.

2. The phenanthroimidazole compound of claim 1, wherein when m is 0, $R_1$ is a carbazole group substituted by an aryl group or a heteroaryl group.

3. The phenanthroimidazole compound of claim 1, wherein when m is 0, $R_1$ is any one selected from the following structures:

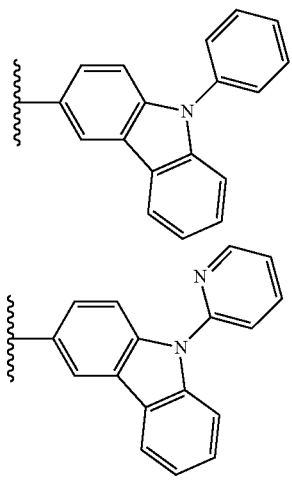

4. The phenanthroimidazole compound of claim 1, wherein when m is 1, $R_1$ is a carbazole group, a carbazole group substituted by an alkyl group, an aryl group, or an alkoxy group, or an amine group substituted by an aryl group, an anthryl group, a pyrenyl group, or

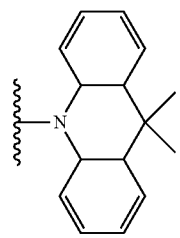

5. The phenanthroimidazole compound of claim 1, wherein when m is 1, $R_1$ is any one selected from the following structures:

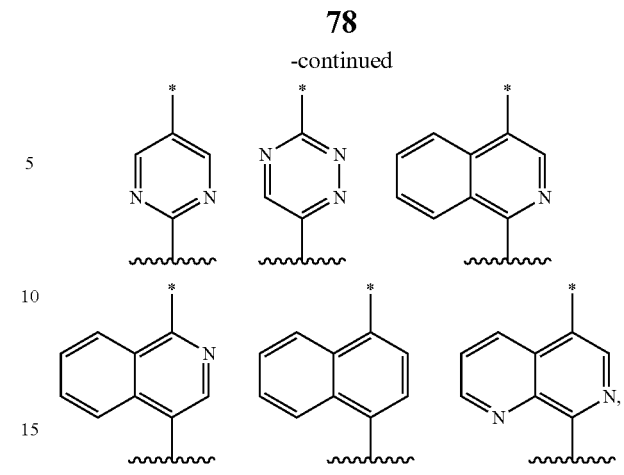
wherein * represents a bonding location with an anthryl group.
7. The phenanthroimidazole compound of claim 1, wherein the phenanthroimidazole compound represented by chemical formula 1 is any one selected from the following structures:
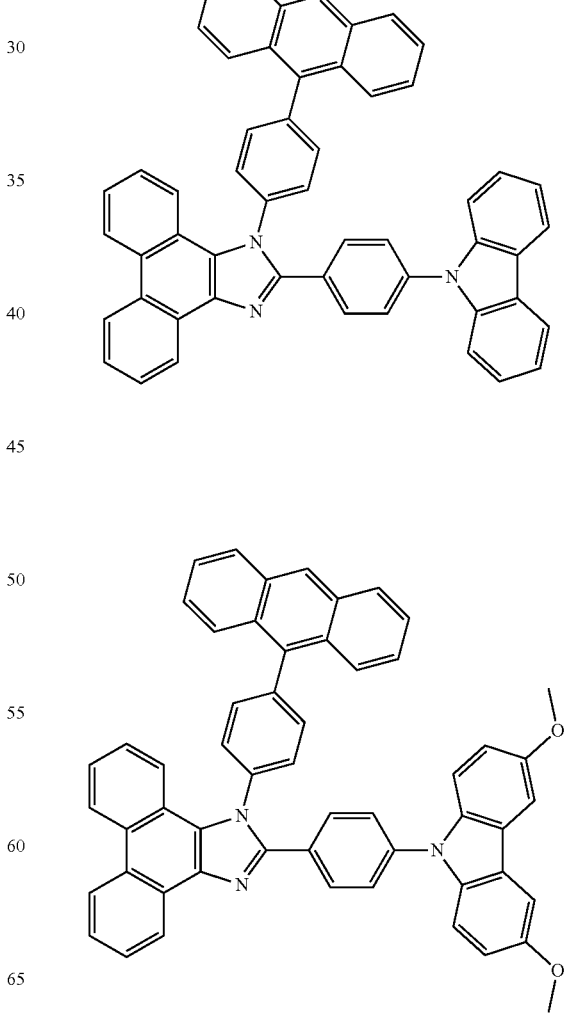
6. The phenanthroimidazole compound of claim 1, wherein $R_2$ is any one selected from the following structures:
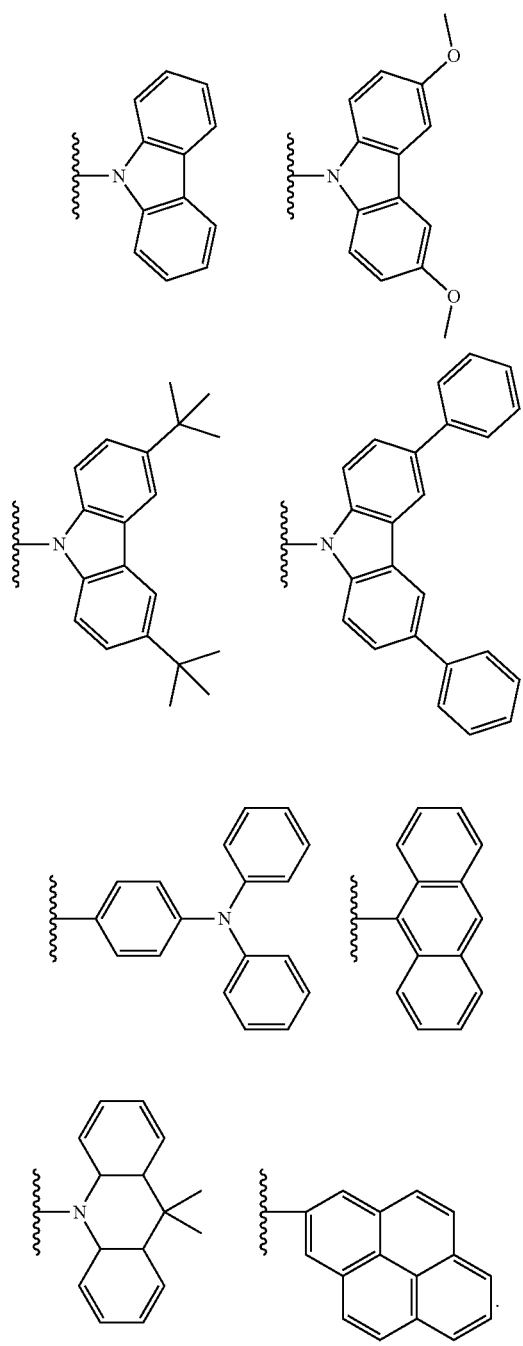
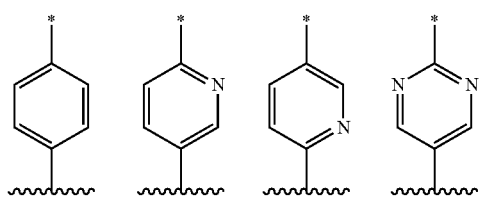

79
-continued
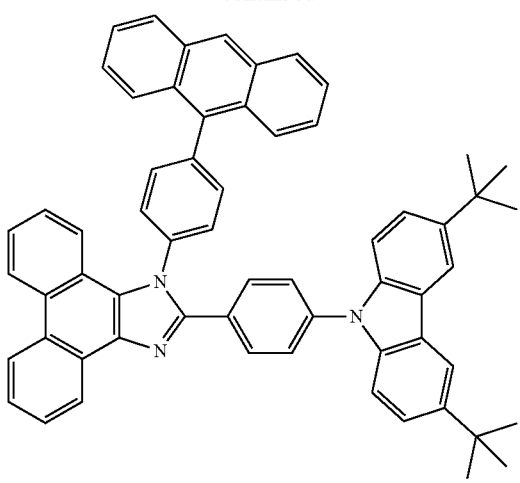
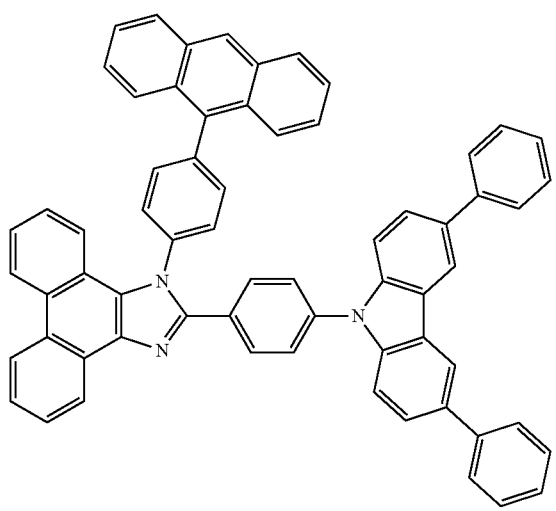
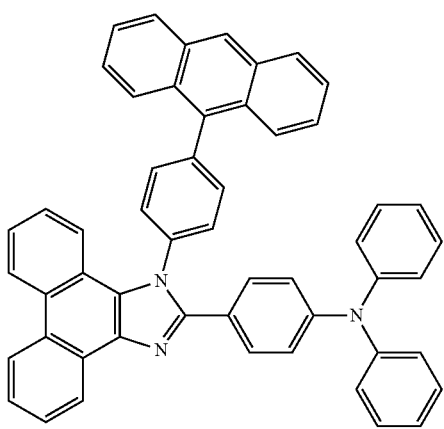
80
-continued
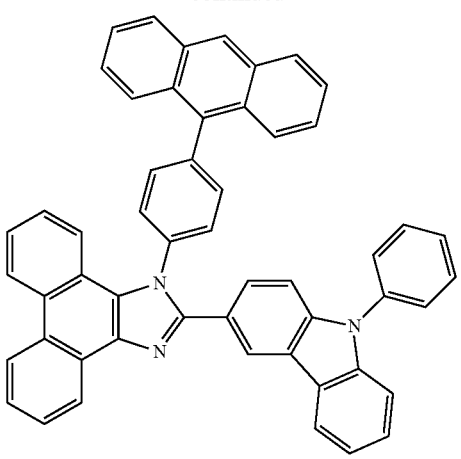
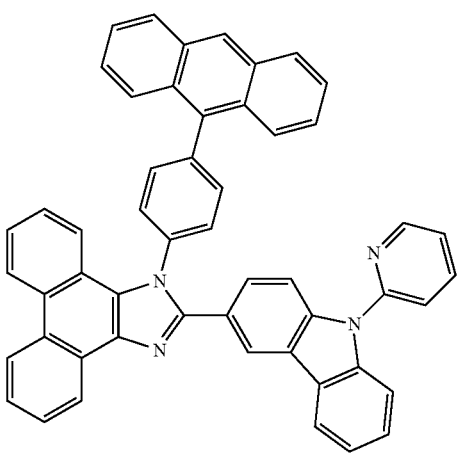
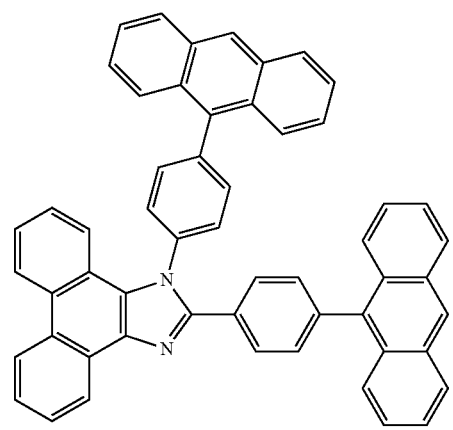

81
-continued
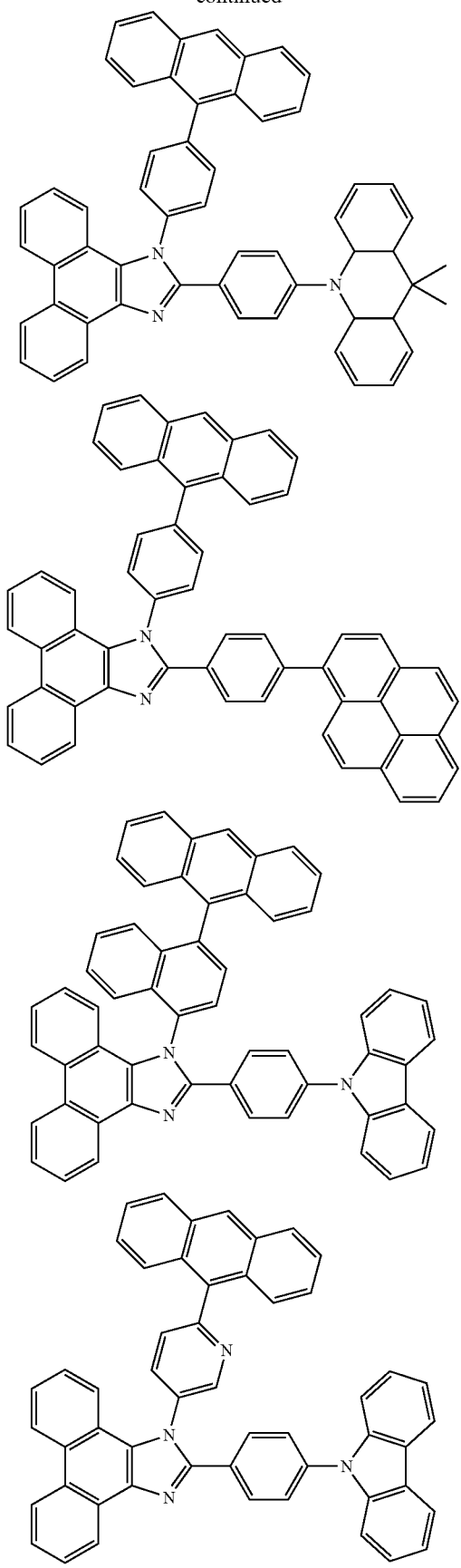
82
-continued
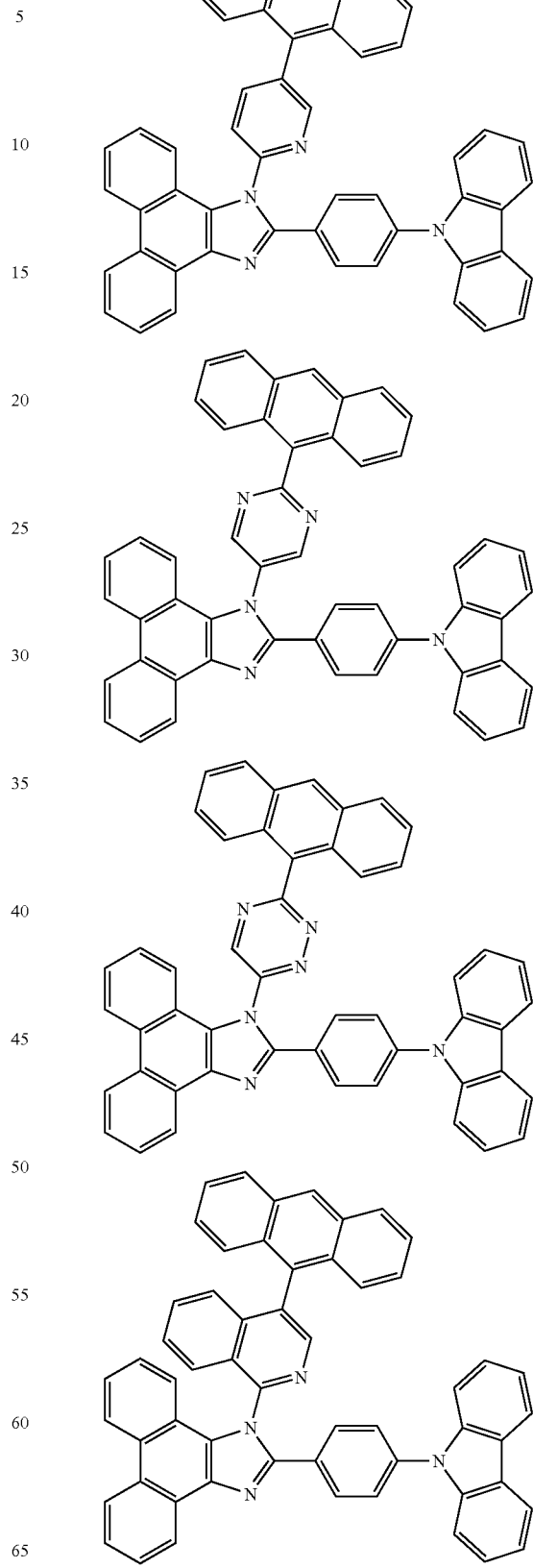

83
-continued
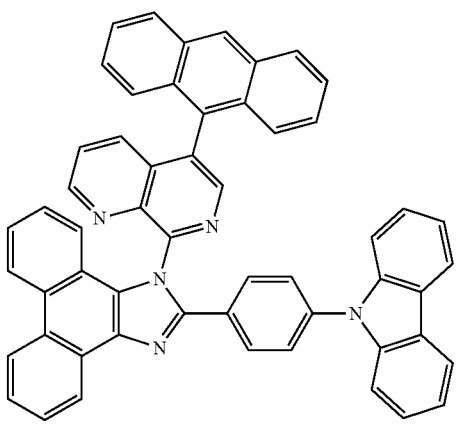
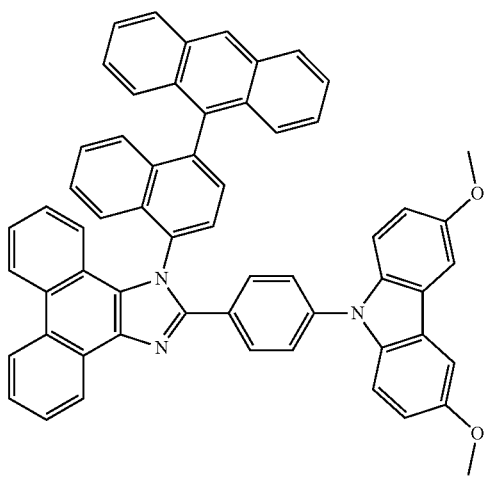
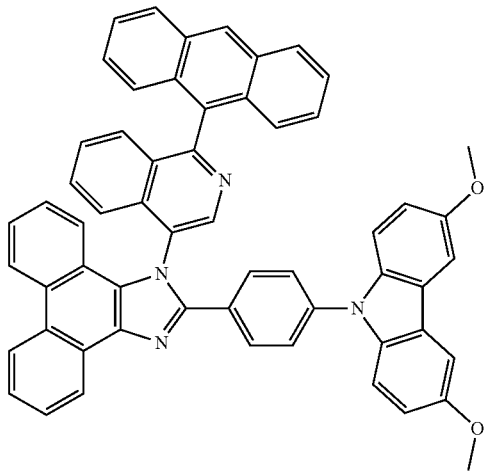
84
-continued
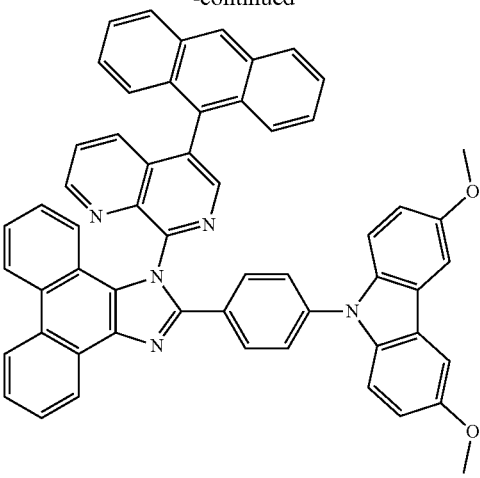
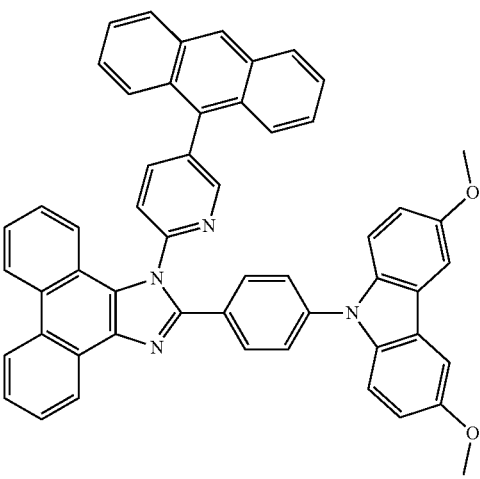

85
-continued
86
-continued
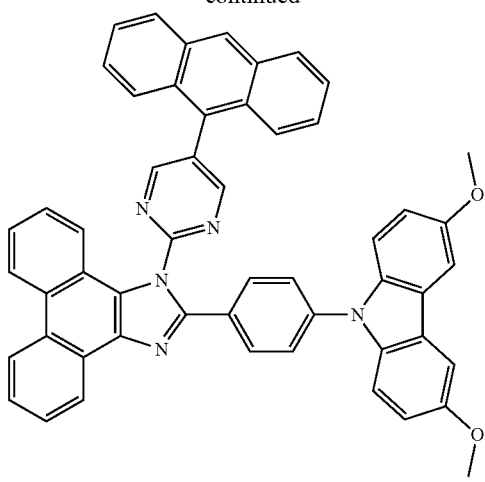
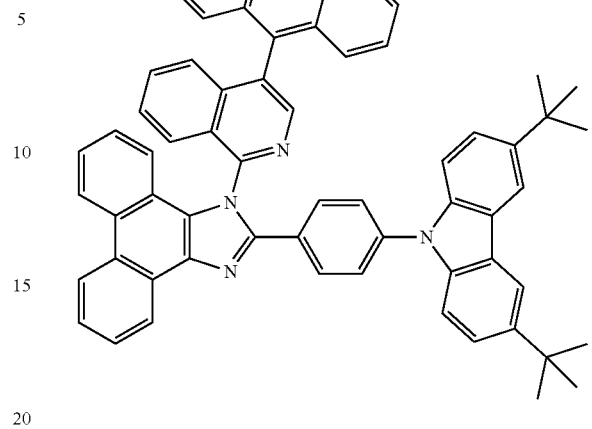
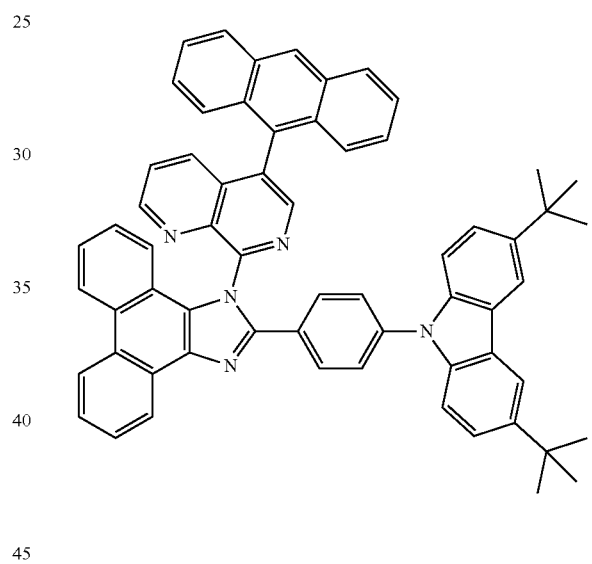
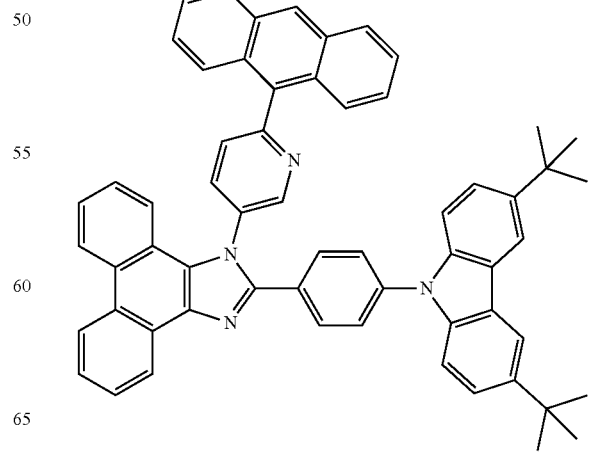

87
-continued
88
-continued
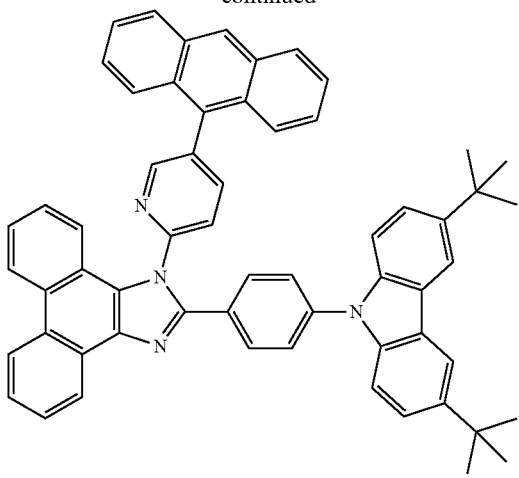
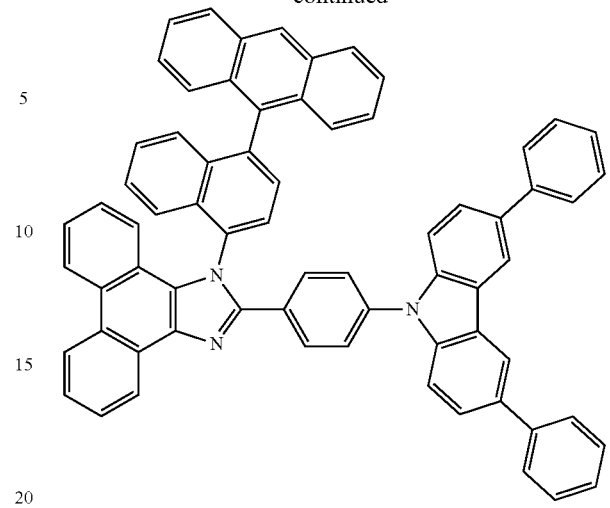
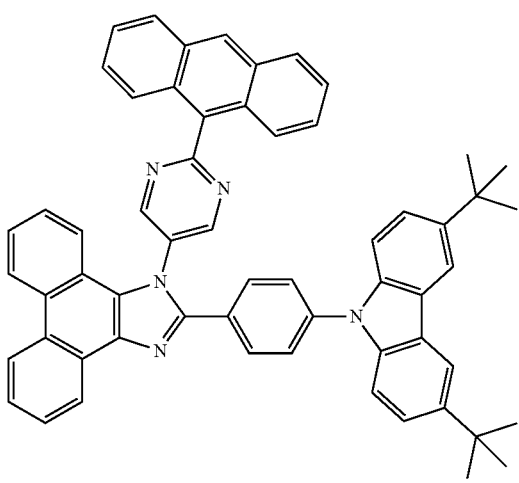
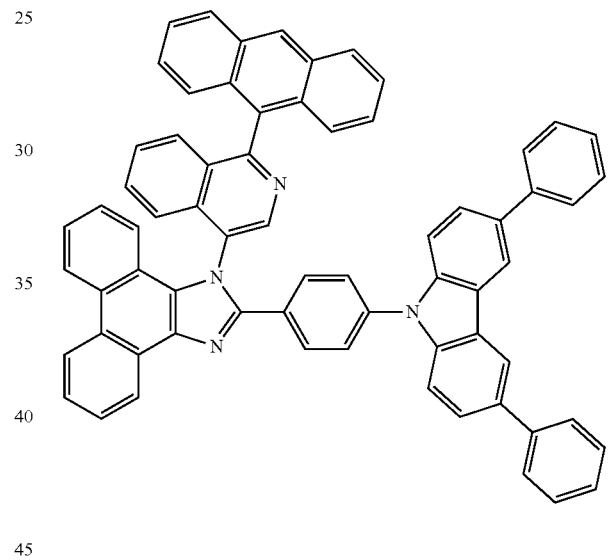
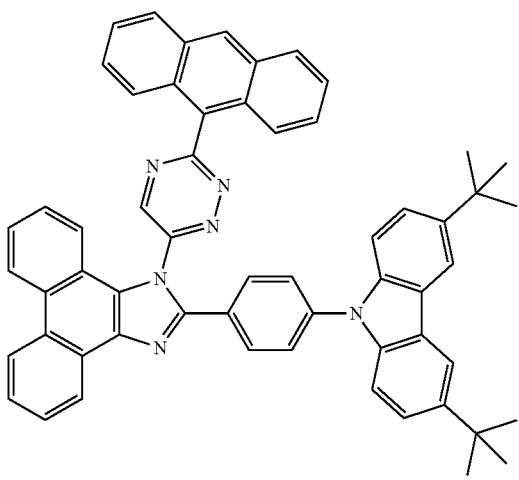
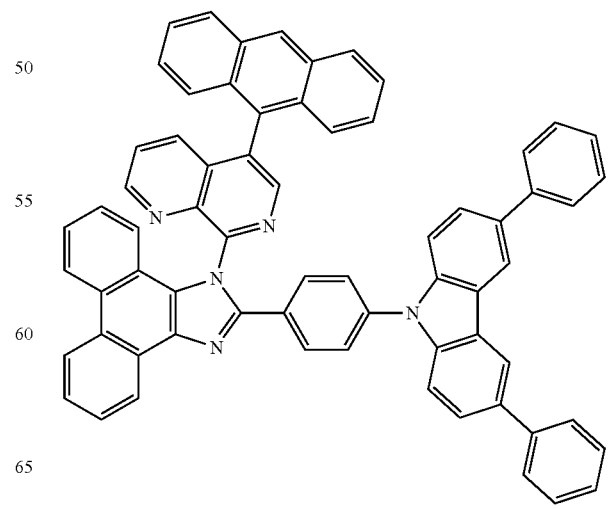

89
-continued
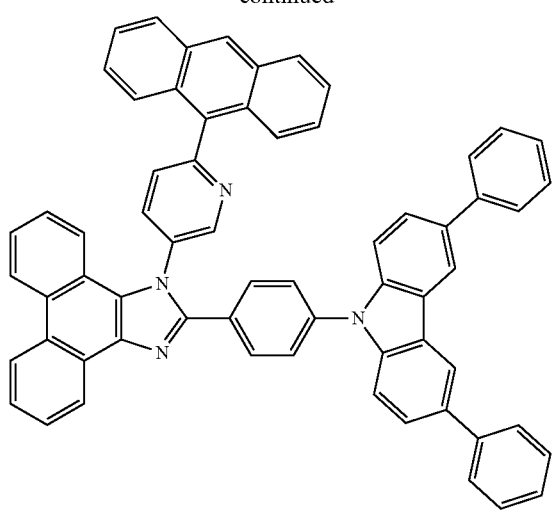
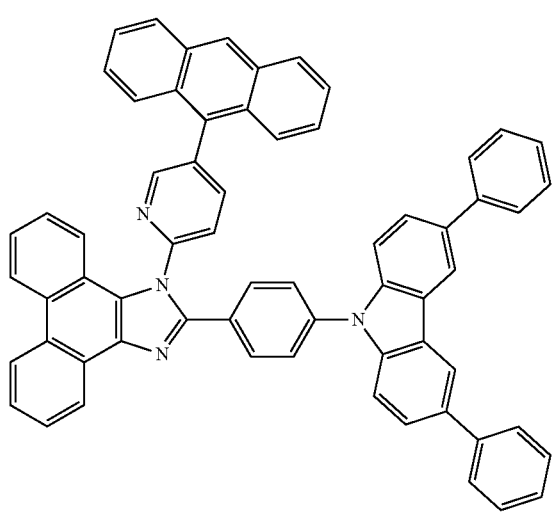
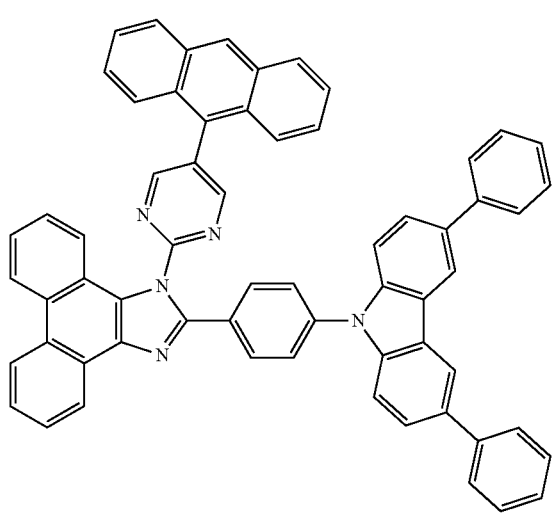
90
-continued
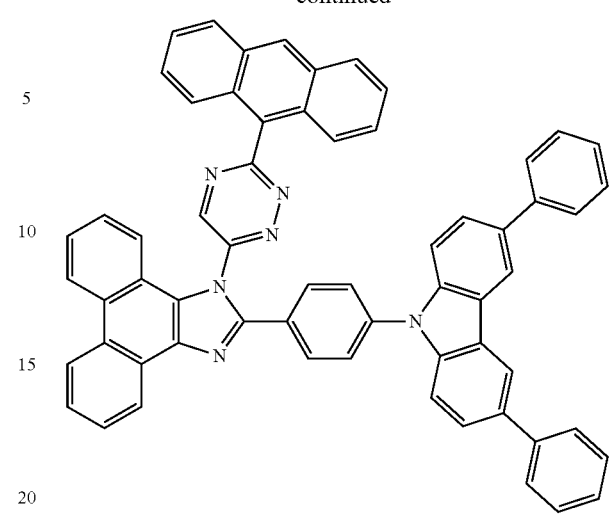
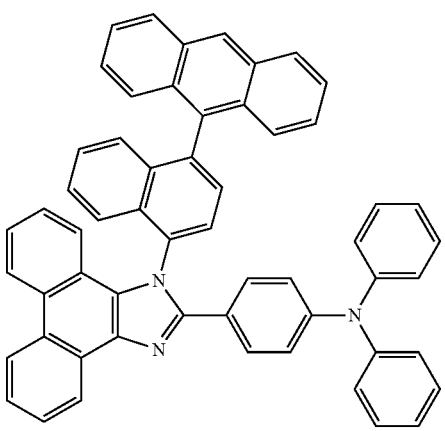
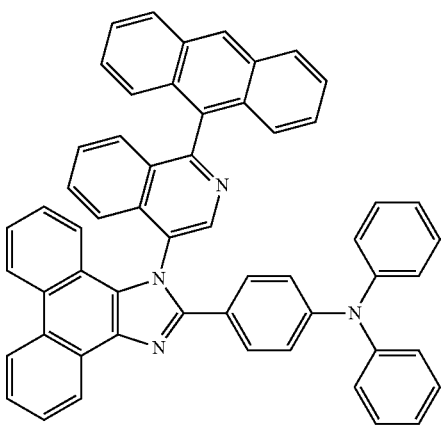

| 91 | 92 |
|---|---|
| -continued | -continued |
| 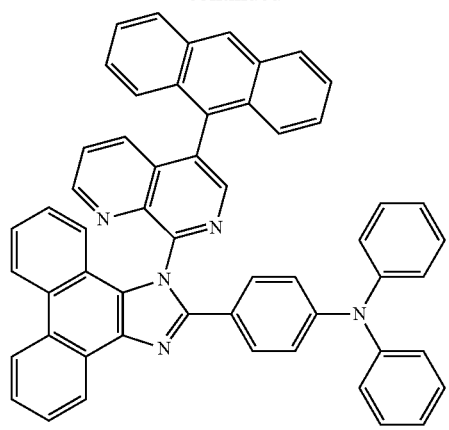 | 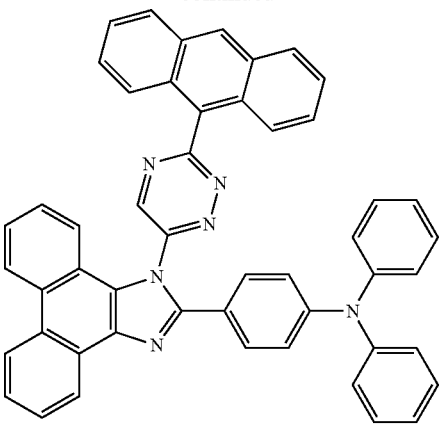 |
| 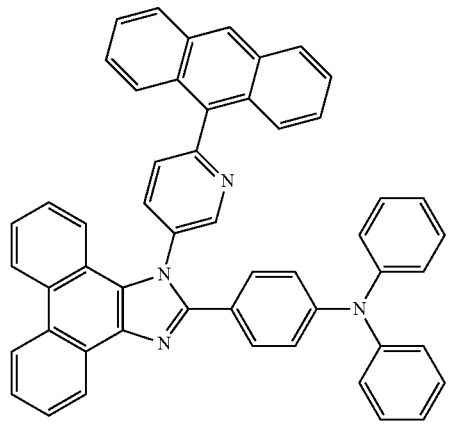 | 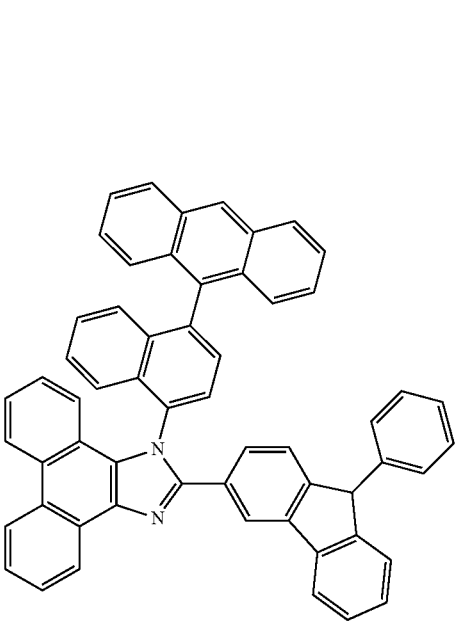 |
| 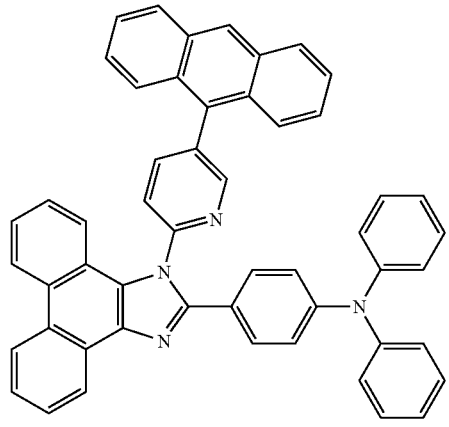 | |
| 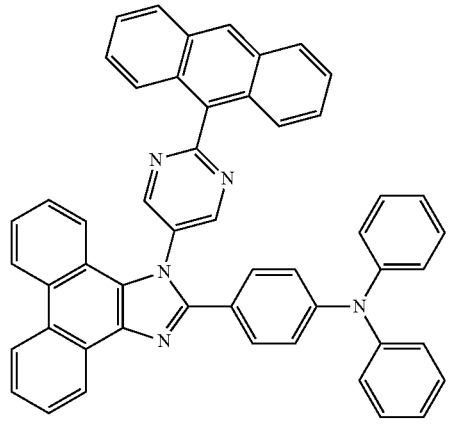 | 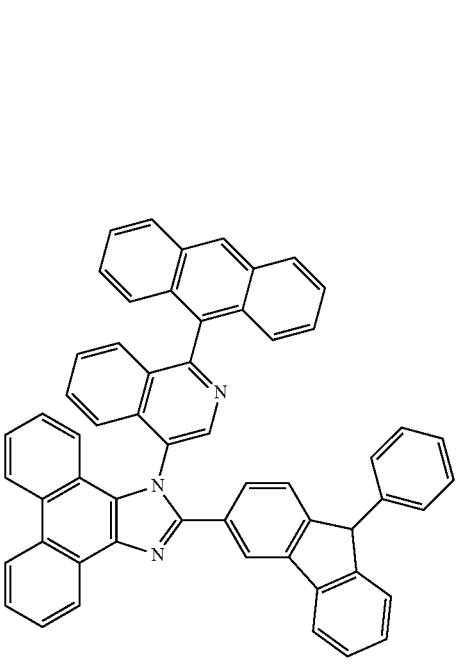 |

93
-continued
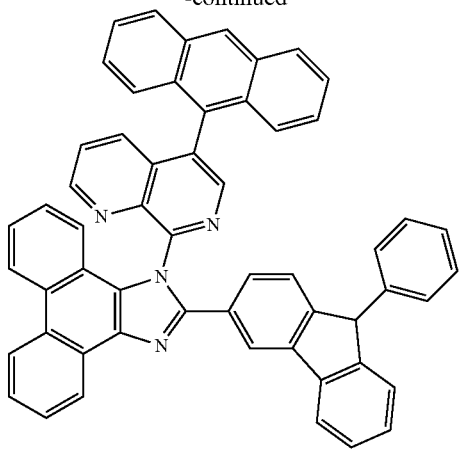
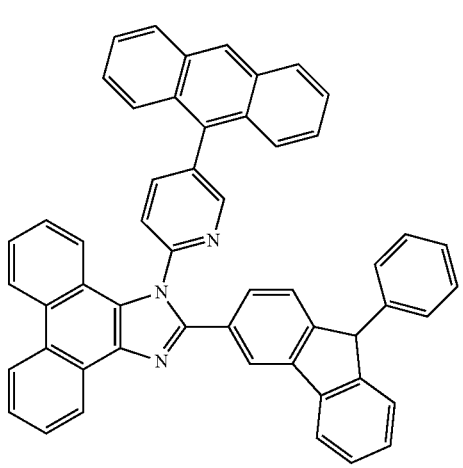
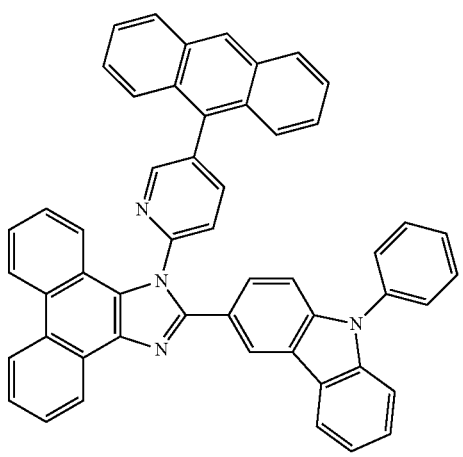
94
-continued
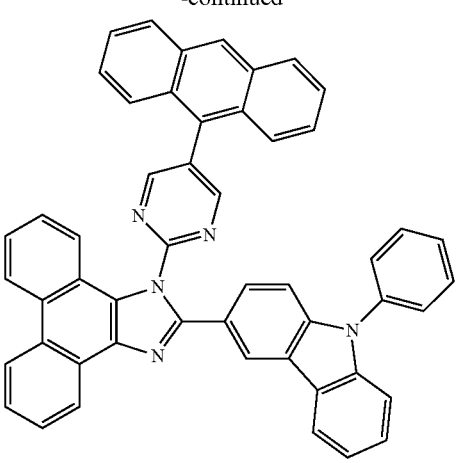
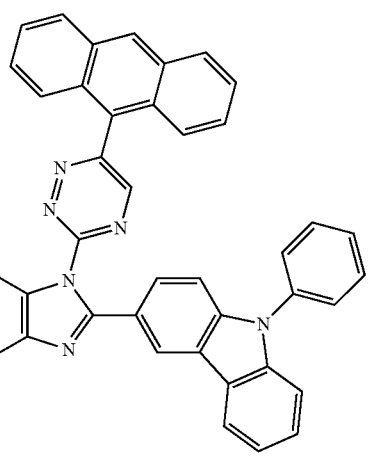
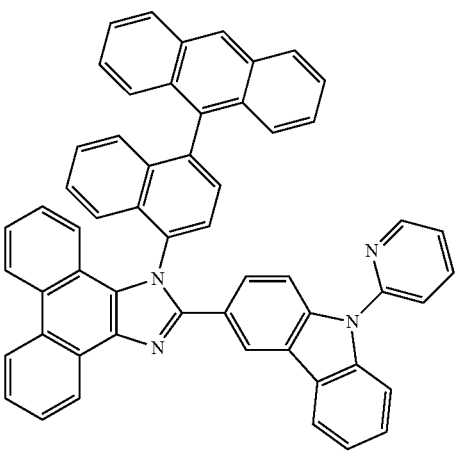

95
-continued
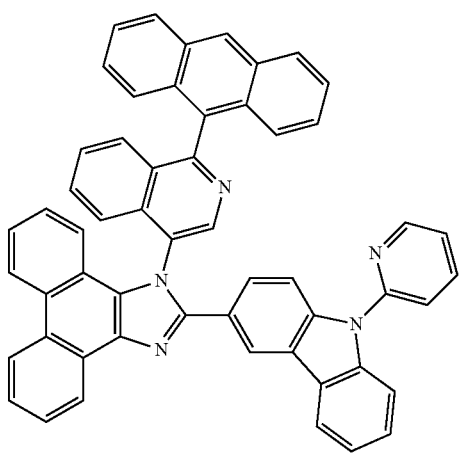
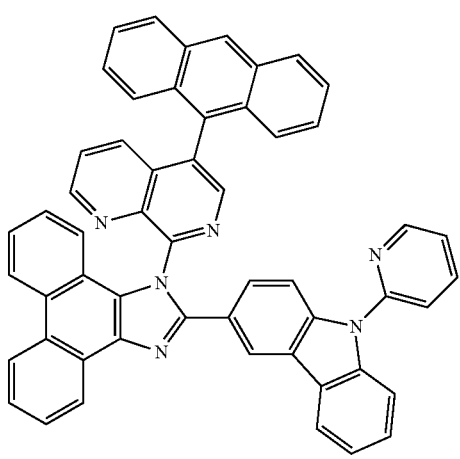
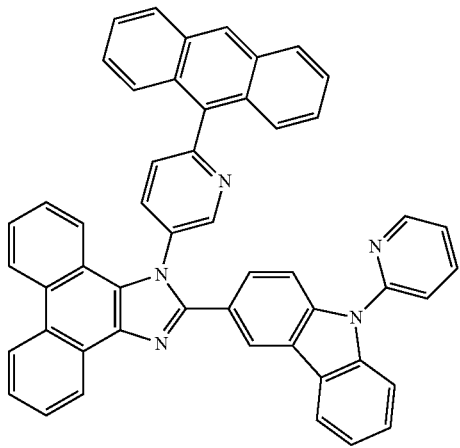
96
-continued
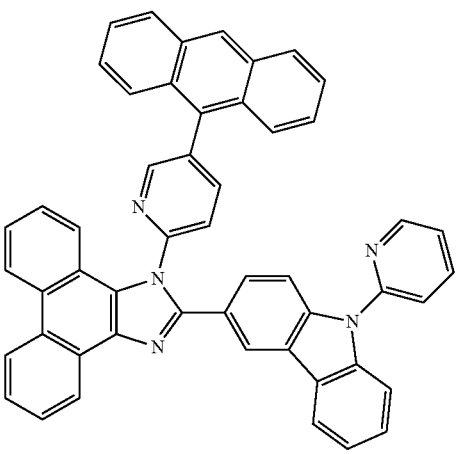
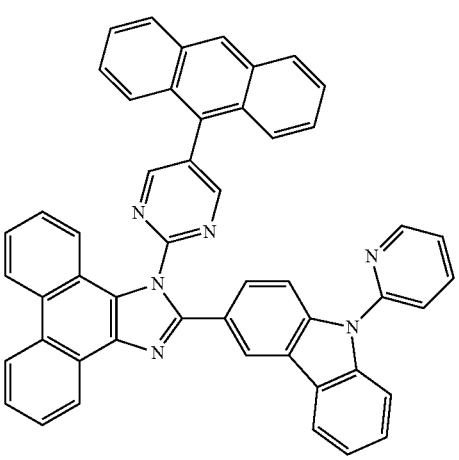
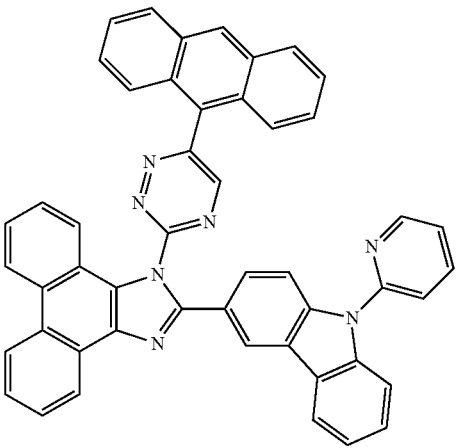

97
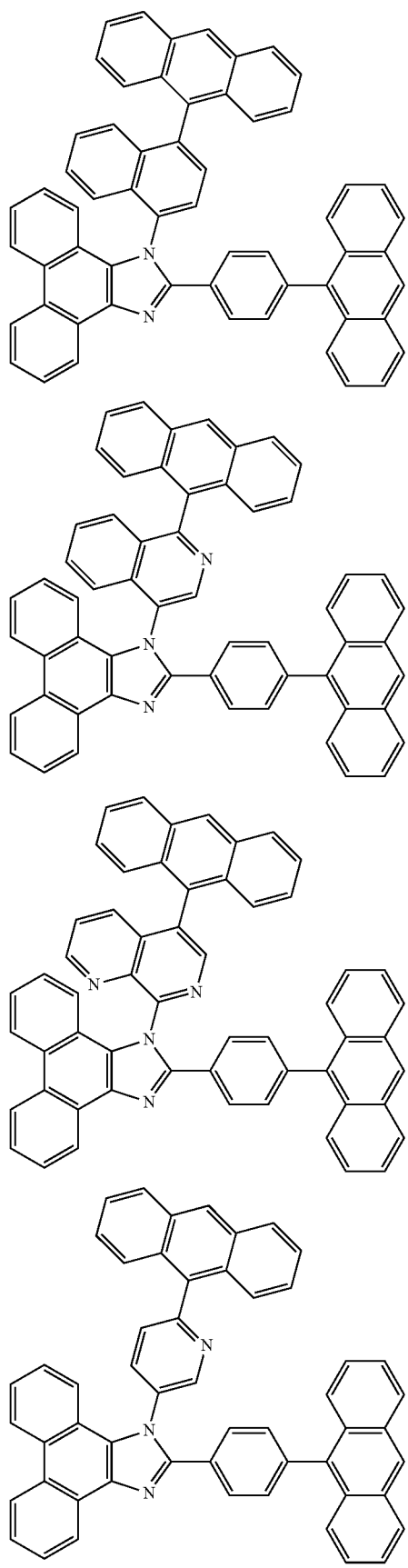
98
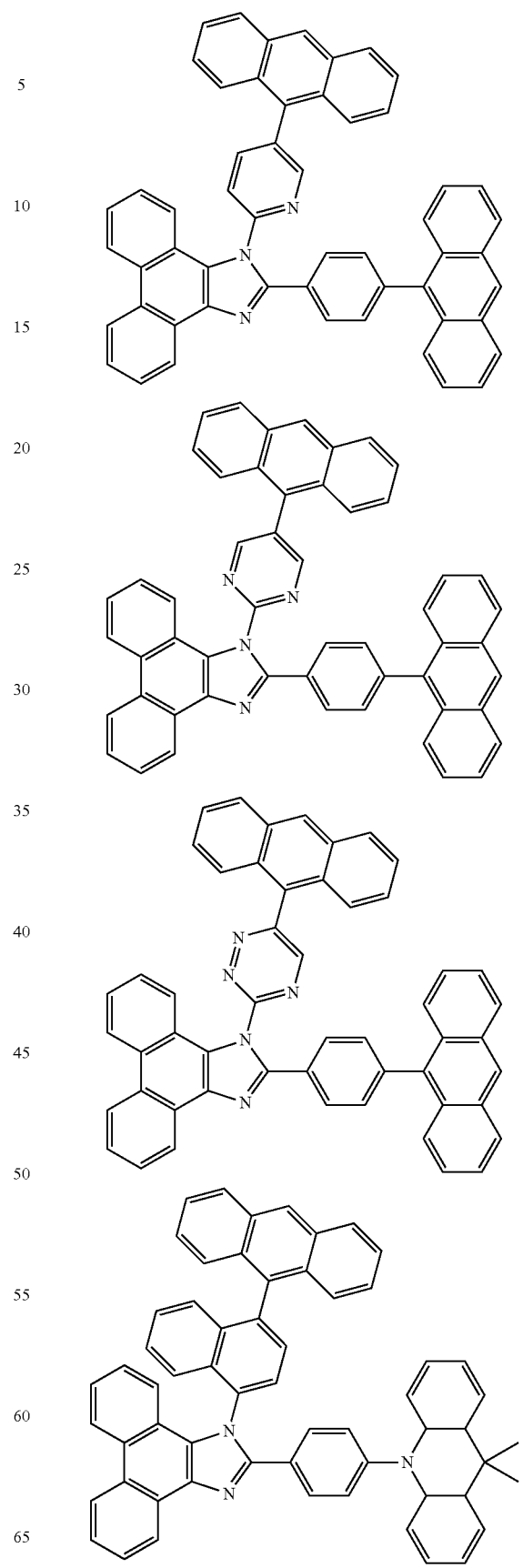

99
-continued
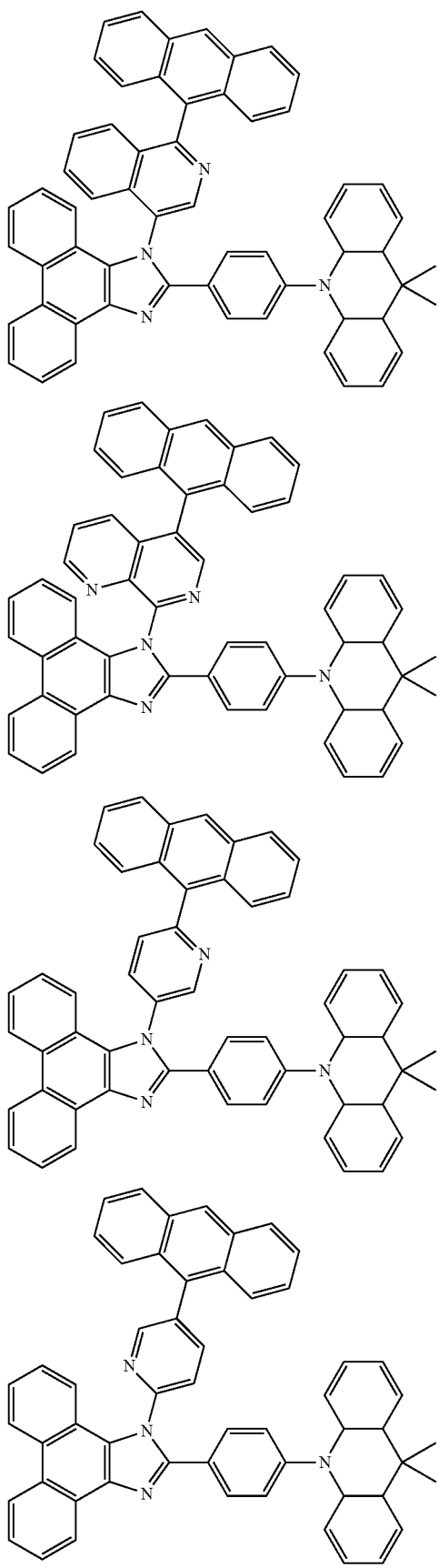
100
-continued
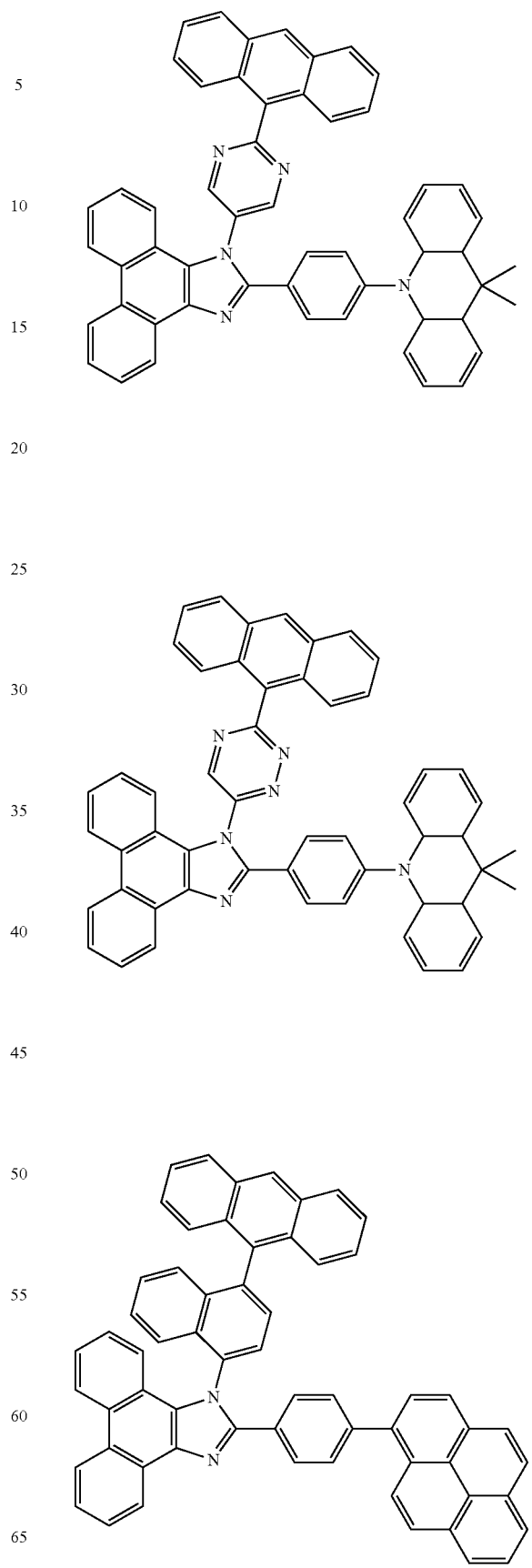

101
-continued

102
-continued

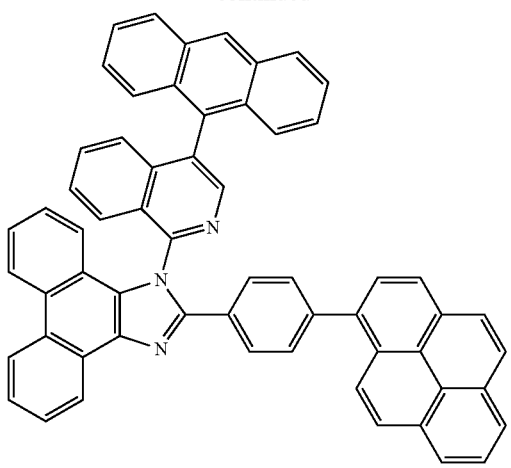

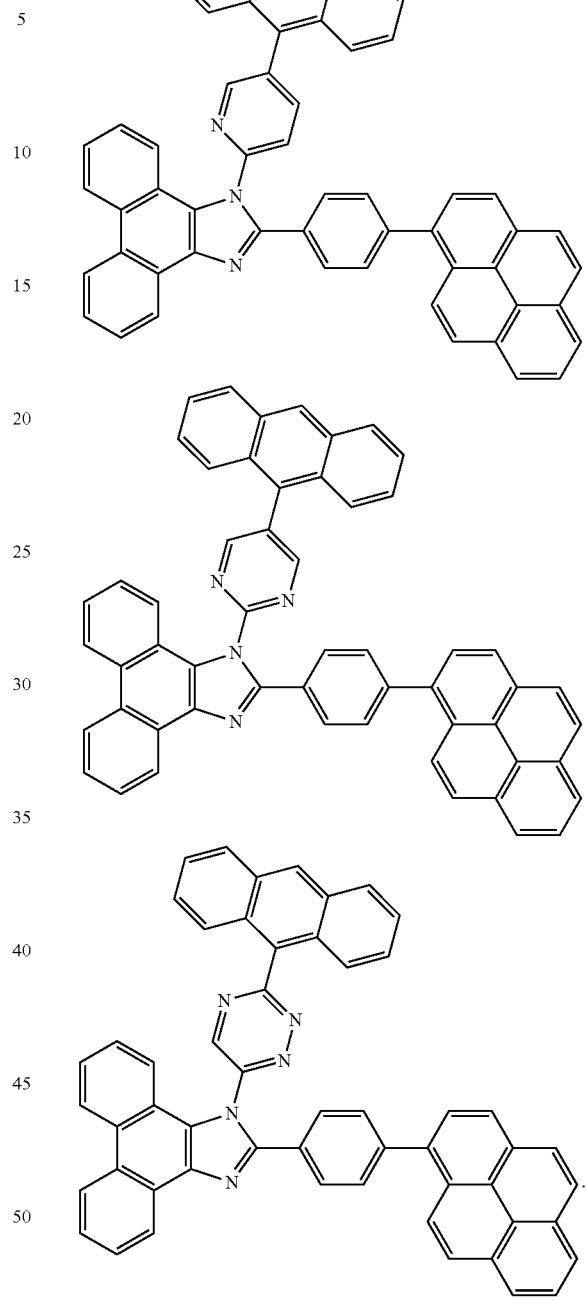

8. An organic light-emitting diode, comprising:
   a cathode;
   an anode; and
   a light-emitting layer disposed between the cathode and the anode, wherein the light-emitting layer contains the phenanthroimidazole compound according to claim 1.

9. The organic light-emitting diode of claim 8, wherein the organic light-emitting diode is a blue light-emitting diode.

10. The organic light-emitting diode of claim 8, wherein the light-emitting layer comprises a host light-emitting material and a guest light-emitting material.

11. The organic light-emitting diode of claim 10, wherein the host light-emitting material comprises the phenanthroimidazole compound.

12. The organic light-emitting diode of claim 8, further comprising at least one auxiliary layer, and the auxiliary layer is selected from the group consisting of a hole injection layer, a hole transport layer, a hole blocking layer, an electron injection layer, an electron transport layer, and an electron blocking layer.

* * * * *